United States Patent [19]

Fujiki

[11] Patent Number: 5,710,301

[45] Date of Patent: Jan. 20, 1998

[54] ORGANOSILICON COMPOUNDS

[76] Inventor: Michiya Fujiki, 1182-1-4-403, Hase, Atsugi, Kanagawa-ken, Japan

[21] Appl. No.: 198,787

[22] Filed: Feb. 18, 1994

[30] Foreign Application Priority Data

| Feb. 23, 1993 | [JP] | Japan | 5-056321 |
| Jul. 26, 1993 | [JP] | Japan | 5-202474 |
| Jul. 26, 1993 | [JP] | Japan | 5-202528 |

[51] Int. Cl.$^6$ .................................................. C07F 7/08
[52] U.S. Cl. ........................... 556/430; 556/465; 556/489
[58] Field of Search ................................... 556/465, 430, 556/489

[56] References Cited

U.S. PATENT DOCUMENTS

| 2,570,462 | 10/1951 | Lipscomb . | |
| 3,088,964 | 5/1963 | Ryan | 556/465 UX |
| 3,532,730 | 10/1970 | Culpepper | 556/465 UX |
| 4,269,993 | 5/1981 | Ohtake et al. | 556/465 UX |
| 4,614,812 | 9/1986 | Schilling, Jr. | 556/406 |
| 4,695,643 | 9/1987 | Oertle et al. | 556/465 |
| 5,296,624 | 3/1994 | Larson et al. | 556/465 X |
| 5,384,383 | 1/1995 | Legrow et al. | 556/465 UX |
| 5,527,938 | 6/1996 | Jung et al. | 556/430 UX |

FOREIGN PATENT DOCUMENTS 0 028 665  5/1981  European Pat. Off. .

OTHER PUBLICATIONS

Chemical Abstracts, vol. 67, No. 9, Aug. 28, 1967, p. 4055. "The Addition of Silicon Hydrides to Olefinic Double Bonds. Part VI. Addition to Branched Olefins", Journal of American Chemical Society, Mar. 10, 1961, pp. 1351–1355.
"Test of the Reversibility of the Platinum–Catalyzed Hydrosilylation of Olefins". The Journal of Organic Chemistry, vol. 32, 1967, pp. 222–223.
"(+)–(S)–2–Methylbutylsilane. Optical Asymmetry Due to Silicon vs. Carbon", The Journal of Organic Chemistry, vol. 31, 1966, pp. 3048–3049.
"Catalytic Asymmetric Hydrosilylation of Olefins", Journal of Organometallic Chemistry, vol. 118, 1976, pp. 161–181.
"Catalytic Asymmetric Hydrosilylation of Olefins", Journal of Organometallic Chemistry, vol. 118, 1976, pp. 331–348.
Chemical Abstracts, vol. 100, No. 7, Feb. 13, 1984, p. 588.
Chemical Abstracts, vol. 14, No. 2, 1920, pp. 1974–1976.
"Ray Initiated Reactions. II. The addition of Silicon Hydrides to Alkenes", Journal of the American Chemical Society, 1958, pp. 1737–1739.
"Novel Packaging Material for Optical Resolution: (+)–Poly(triphenylmethyl methacrylate) Coated on Macroporous Silica Gel", J. Am. Chem Soc., 103, 6791, 1981.
Bazant et al., Academic Press, vol. 2, Part 1, N.Y.(1965), pp.106 & 107.
Bazant et al., *Organosilicon Compounds*, vol. 2, Part 1, Academic Press, N.Y., Jun. 1995, pp. 93, 124, 127, 172, 180, and 241.

Primary Examiner—Paul F. Shaver

[57] ABSTRACT

The present invention provides an oganosilicon compound possessing a β-branched alkyl group or a β-branched aralkyl group represented by Formula (I):

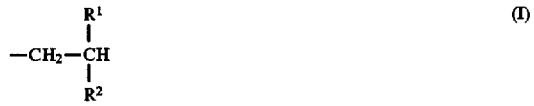

wherein $R^1$ represents methyl group or ethyl group; $R^2$ represents C1–C18 alkyl group or aryl group. The present invention relates to optically active organosilicon compounds for use as a new type of enantio-recognitive material, and organosilicons which can be anticipated for use as a high polymer standard material in one-dimensional semiconductor quantum wire structures.

11 Claims, 34 Drawing Sheets

ORGANOSILICON COMPOUNDS

BACKGROUND OF THE INVENTION

1. Field of the Invention

The present invention relates to optically active organosilicon compounds which have anticipated uses as new types of enantio-recognitive materials, and organopolysilanes which have anticipated uses as polymer standard materials in one-dimensional semiconductor.quantum wire structures.

2. Prior Art

Numerous organosilicon compounds for industrial use are currently available: for example, surface treating agents, water-repellent.oil-repellent agents, electric insulators, thermal media, and precursors of ceramic material, all represent polymers which incorporate silicon in a portion of their molecular skeletons. Recently, organopolysilanes which are soluble in certain solvents and which possess main-chains constructed only of silicon are attracting attention as a new type of functional material. With regard to this, a large amount of information is being reported relating to research being conducted on the practical application of the aforementioned organopolysilanes, such as in photoresists, optical waveguide materials, precursors of silicon carbides, electrophotographic sensitizing materials, nonlinear optical materials, photoluminescent materials, and the like.

In general, organopolysilane has an ultraviolet absorption band in approximately the 3 to 4 eV range in the Si—Si chain based on its characteristic main-chain. The backbone absorption at room temperature in solution normally displays a molecular absorption coefficient of approximately 5000–8000 (Si repeating unit)$^{-1}$.dm$^3$.cm$^{-1}$, with a full width at half maximum of approximately 0.5–0.6 eV (approximately 40–60 nm). In contrast, the photoluminescence full width at half maximum of the backbone at room temperature in solution is approximately 0.1–0.2 eV (approximately 10–20 nm), which is quite narrow when compared to the backbone absorption. In other words, the photoluminescence spectrum and the absorption spectrum of organopolysilane do not display a mirror image relationship as seen from the absorption photoluminescence phenomenon of normal organic material.

The reasons for this have been previously clarified as a result of extensive research in that a main-chain of organopolysilane with trans zig-zag or loose helical structures behave as a collection of various segments aggregate which is formed by segments with trans zig-zag or loose helical structures via a conformational defect. In other words, the full width at half maximum of the backbone of organopolysilane is the sum of these segments possessing the various absorption maximums. The light excitation of the backbone absorption causes energy migration to the segment portion with the lowest excitation energy, and photoluminescence occurs from this portion. Consequently, the optical and electrical properties such as the reported hole mobility, nonlinear optical characteristics and the like of conventional organopolysilane are essentially controlled by the many defects within the backbone, and are thus thought to be too far from the actual properties originally possessed by organopolysilane.

Because organopolysilane is a polymer with a main-chain comprised only from silicon, breakdown of the backbone easily occurs due to ultraviolet irradiation, which leads to molecular weight reduction or transformation to siloxane. Examples of practical application in which the aforementioned material was actually used as a photoresist have been reported. Consequently, organopolysilanes are not appropriate for practical use as functional materials relating to optics such as electrophoto sensitizing material, nonlinear optical material, photoluminescent material, and the like. However, because of the simplicity of synthesis, a polymer that is soluble in a solvent and displays ultraviolet absorption.photoluminescence can be easily produced using a relatively simple chemical synthesis, and thus, with regard to this point, is important in serving as an important model substance in the fundamental research of optical and electrical materials for one-dimensional semiconductor material; such a substance is quite marketable as a standard polymer material.

On the other hand, as a polymer material for recognizing enantiomers, carbon skeleton backbone polymers such as poly(triphenylmethyl methacrylate), poly (diphenylpyridylmethyl methacrylate), and the like are known which possess a one-handed helicity and are synthesized using sparteine as a polymerization initiator (see Okamoto, Y., et al., J. Am. Chem. Soc.; Vol. 103, page 6971 (1981)). These organic polymers having a one-handed helicity which, in actuality, are layered onto a silica gel surface, and are employed as column material for high speed liquid chromatography for carrying out separation and resolution of enantiomers, are commercially available ("Chiralpak-OT", "Chiralpack-OP", produced by Daicel Chemical Industries). However, these poly(triarylmethyl methacrylate)-based materials possess a fatal drawback in that the backbone helicity is gradually lost due to hydrolysis and/or solvolysis of the triaryl ester moiety of the side chain which fixes the backbone helicity, while a loss of the enantio-recognitive function occurs at the same time.

If the resistances to hydrolysis and solvolysis of the silicon main-chain and hydrocarbon side chains of the above organopolysilane can be developed, use as a column material for high performance liquid chromatography (hereafter referred to as HPLC) and gas chromatography (hereafter referred to as GC) under normal, dark, and deaeration conditions, will be possible. Furthermore, if the structure of the polymer is an organopolysiloxane structure with optical activity, the resistance to oxygen can be expected to be greater than that of organopolysilane. For example, it may be conceived that oxidation of a thermodynamically unstable organopolysilane skeleton may result in conversion to a thermodynamically stable, optically active organopolysiloxane. However, even still, the enantio-recognitive ability derived from the chirality of the backbone is maintained, and consequently, the ability to withstand repeated practical use over a long period can be anticipated.

At the moment, as a means for separating and analyzing using HPLC, there exists a particularly strong demand for column material (hereafter referred to as CSP) for use in enantiomer recognition which can be employed even under reversed phase mode conditions. Most of the CSP materials for use in reversed phase are substances originating in the biological species. A large portion of these substances are alkyl derivatives possessing amide bonds, and thus there still remains the problem of column degradation due to hydrolysis. If a monomeric or polymeric siloxane derived from a chlorosilane-based material possessing an optically active substituent can be carried by a column carrier, or if an optically active organopolysilane possessing the own helicity of the main-chain can be carried by a carrier, the material may be used as CSP for use in HPLC, or as CSP for use in GC. However, at the present time, the aforementioned types of organopolysilanes or organopolysiloxanes remain unknown.

SUMMARY OF THE INVENTION

An object of the present invention is to provide optically active organosilicon compounds possessing a structure in which an organic substituent incorporating a chiral center is directly bonded to a silicon atom, the compounds also having a one-handed helical stability, even in solution, at room temperature, as an enantio-recognitive material, in particular as material for use in CSP for HPLC or GC, as well as, as a model standard material for use in one-dimensional semiconductor.quantum wire structural property research.

In addition, it is another object of the present invention to provide an organopolysilane possessing an extremely strong backbone absorption and an extremely narrow full width at half maximum which is produced by a sodium-mediated polymerization reaction of organochlorosilanes with a β-branched chiral or achiral alkyl substituent, for use as a model in the aforementioned research, since model material for use in one-dimensional semiconductor and model material for use in exciton research which can ignore the interchain interaction, have not been obtained as described above.

The present invention provides an organosilicon compound possessing a β-branched alkyl group or a β-branched aralkyl group represented by Formula (I):

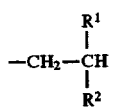

(I)

wherein $R^1$ represents methyl group or ethyl group; $R^2$ represents C1–C18 alkyl group or aryl group.

Figure 20:
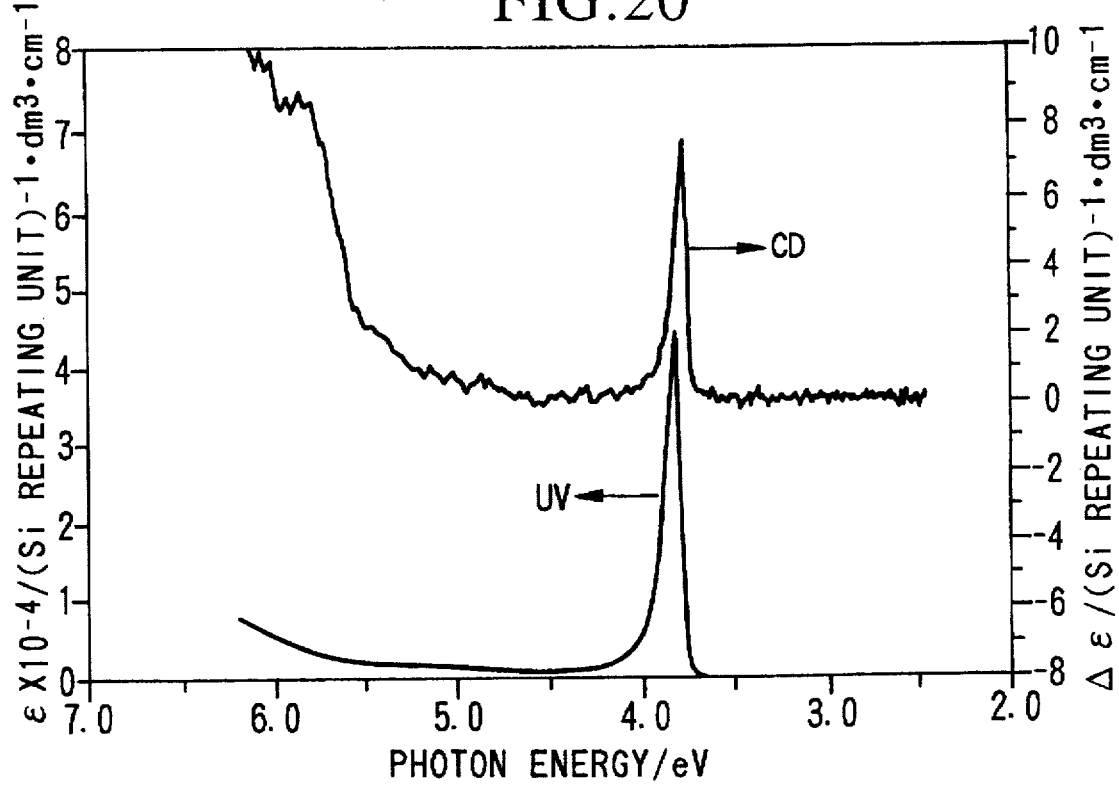
Figure 21:
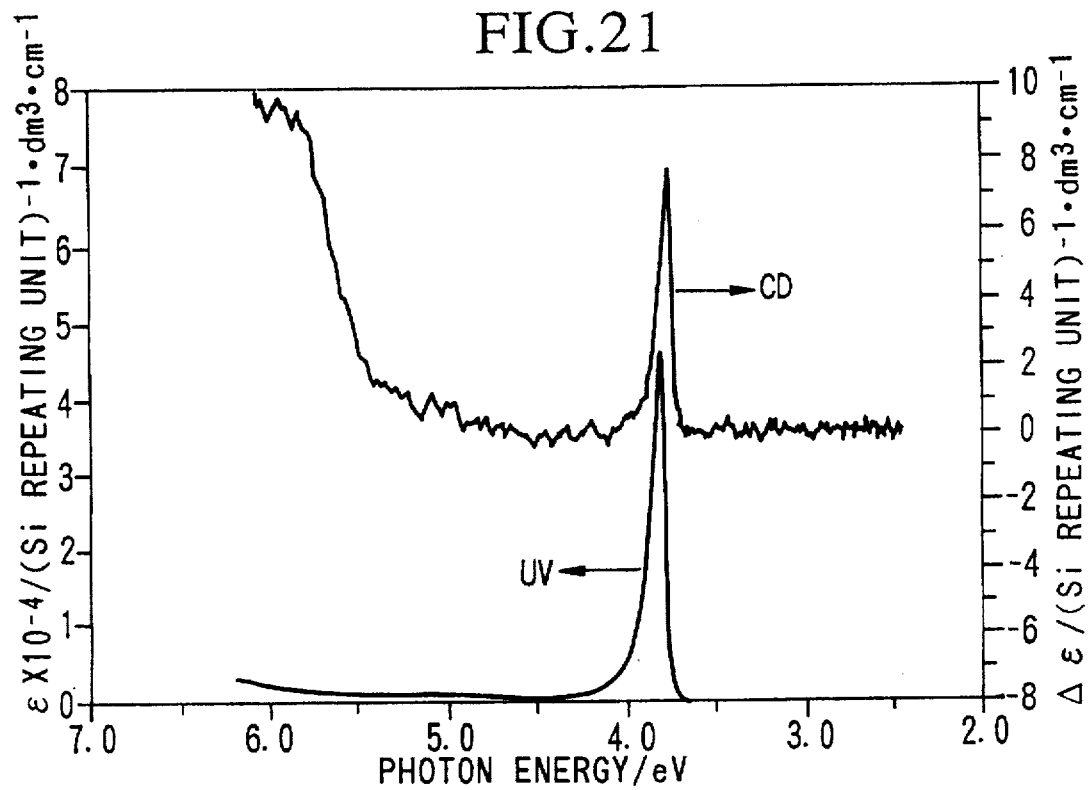
Figure 22:
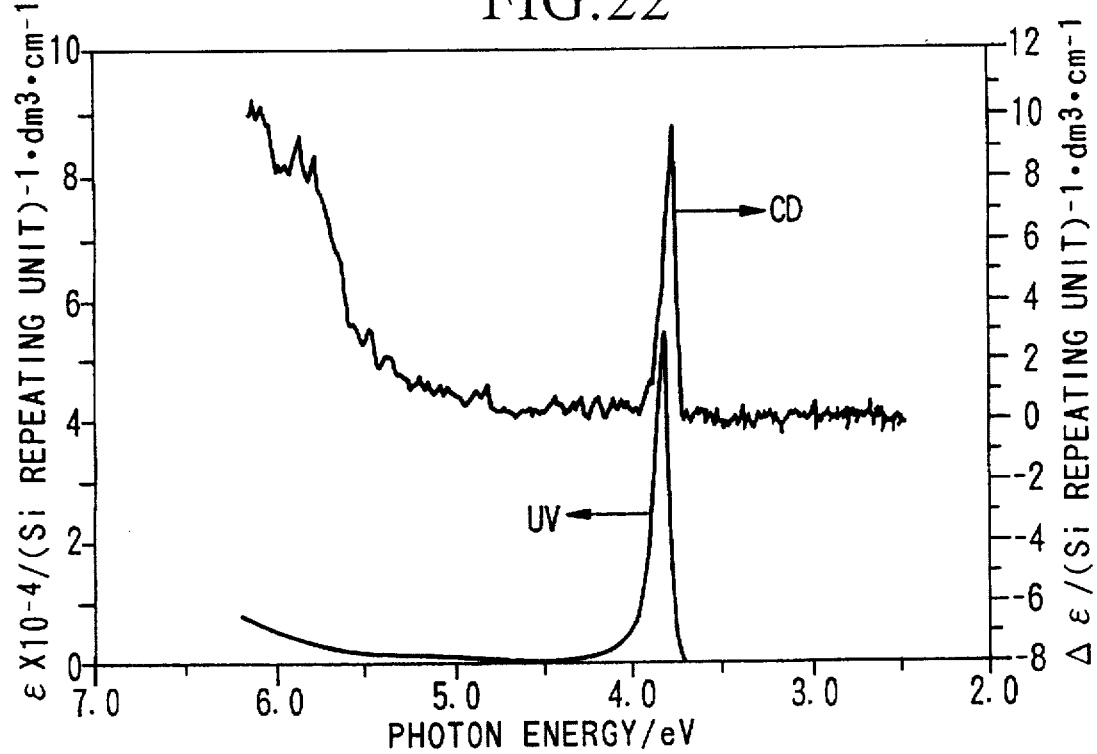
Figure 23:
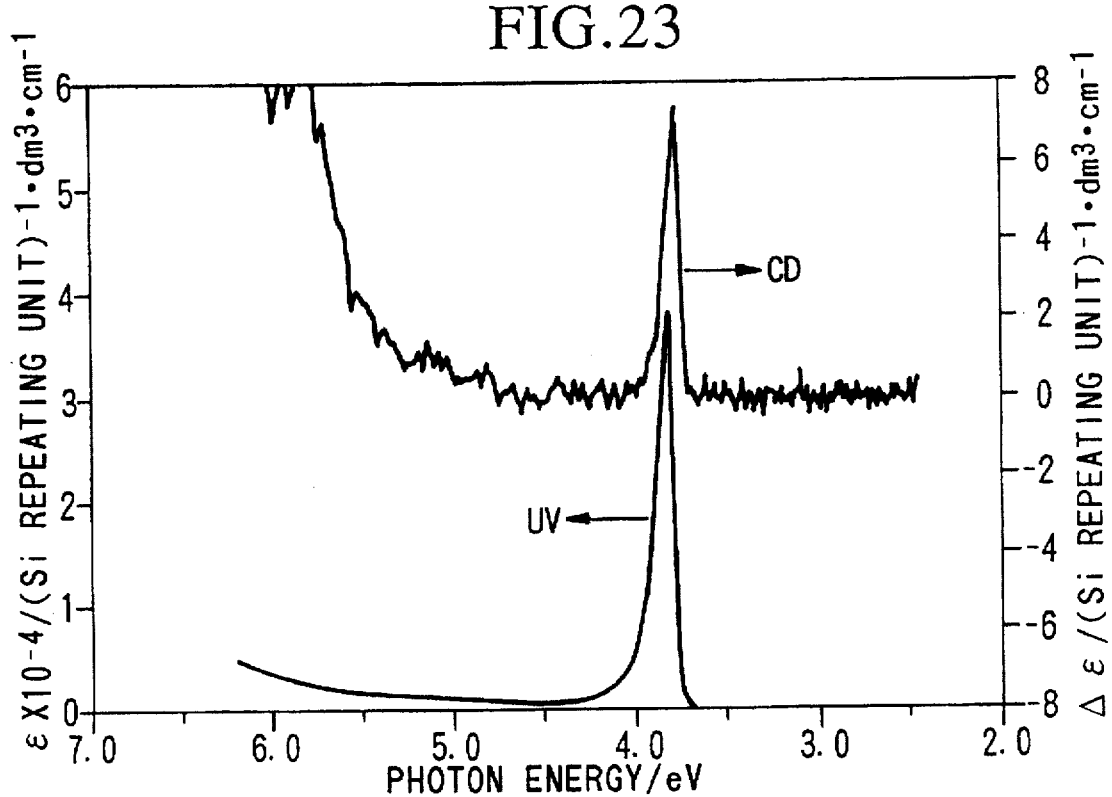
Figure 24:
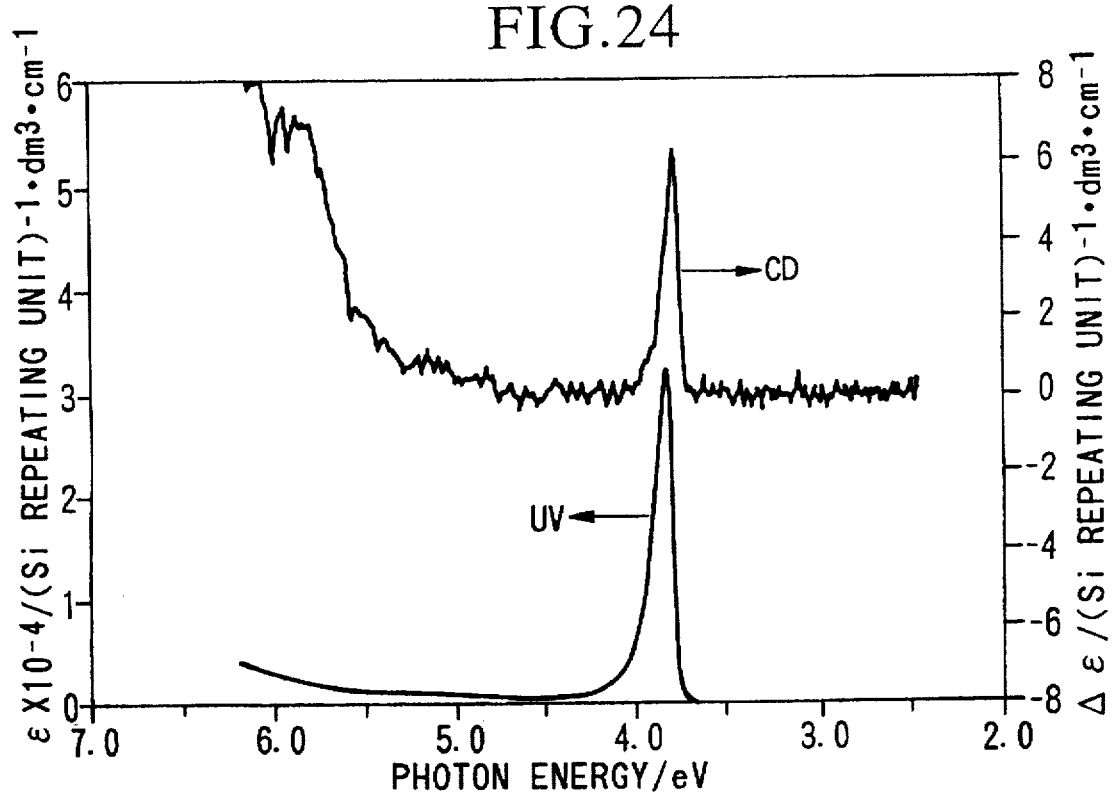
Figure 25:
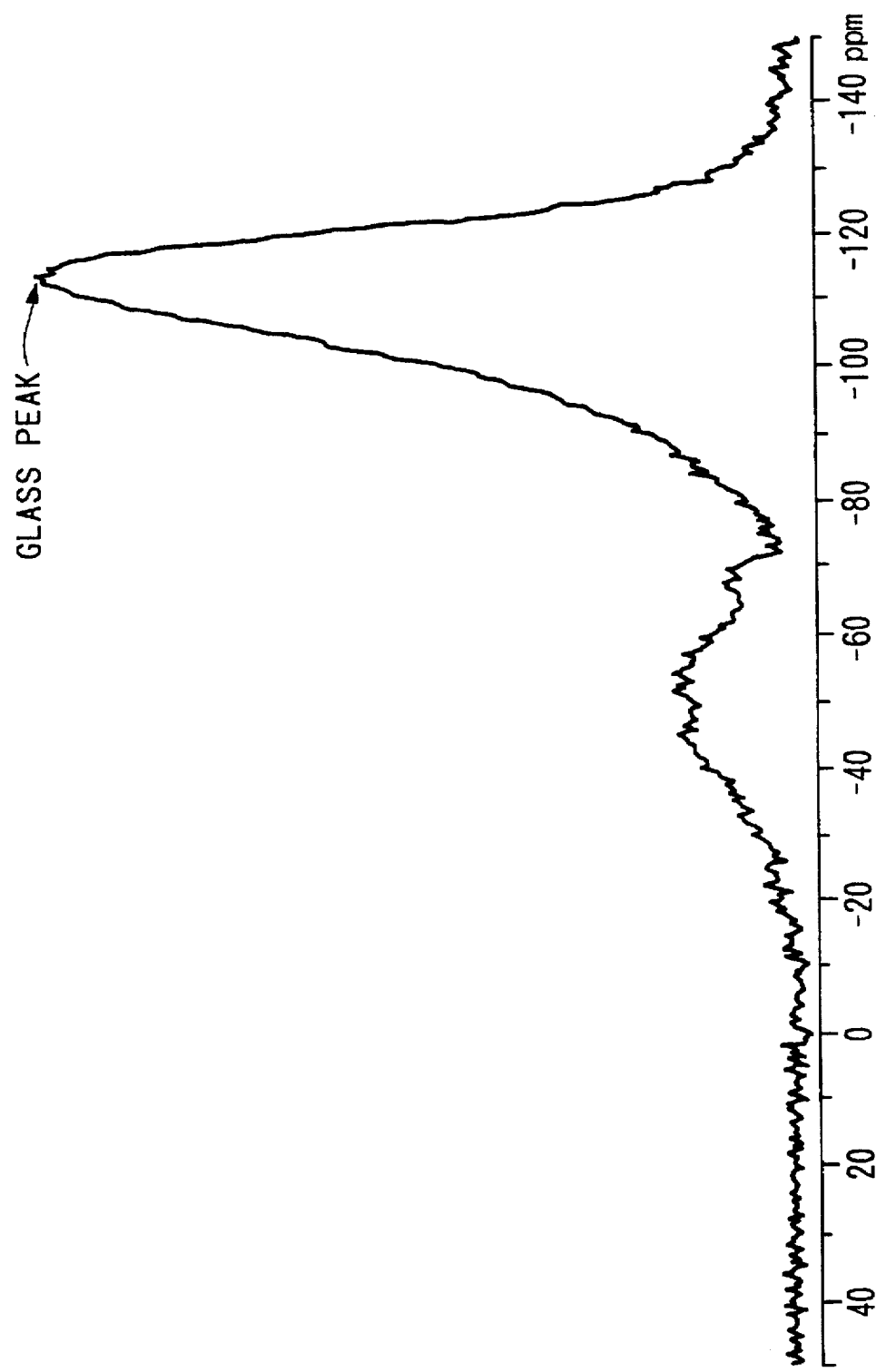
Figure 26:
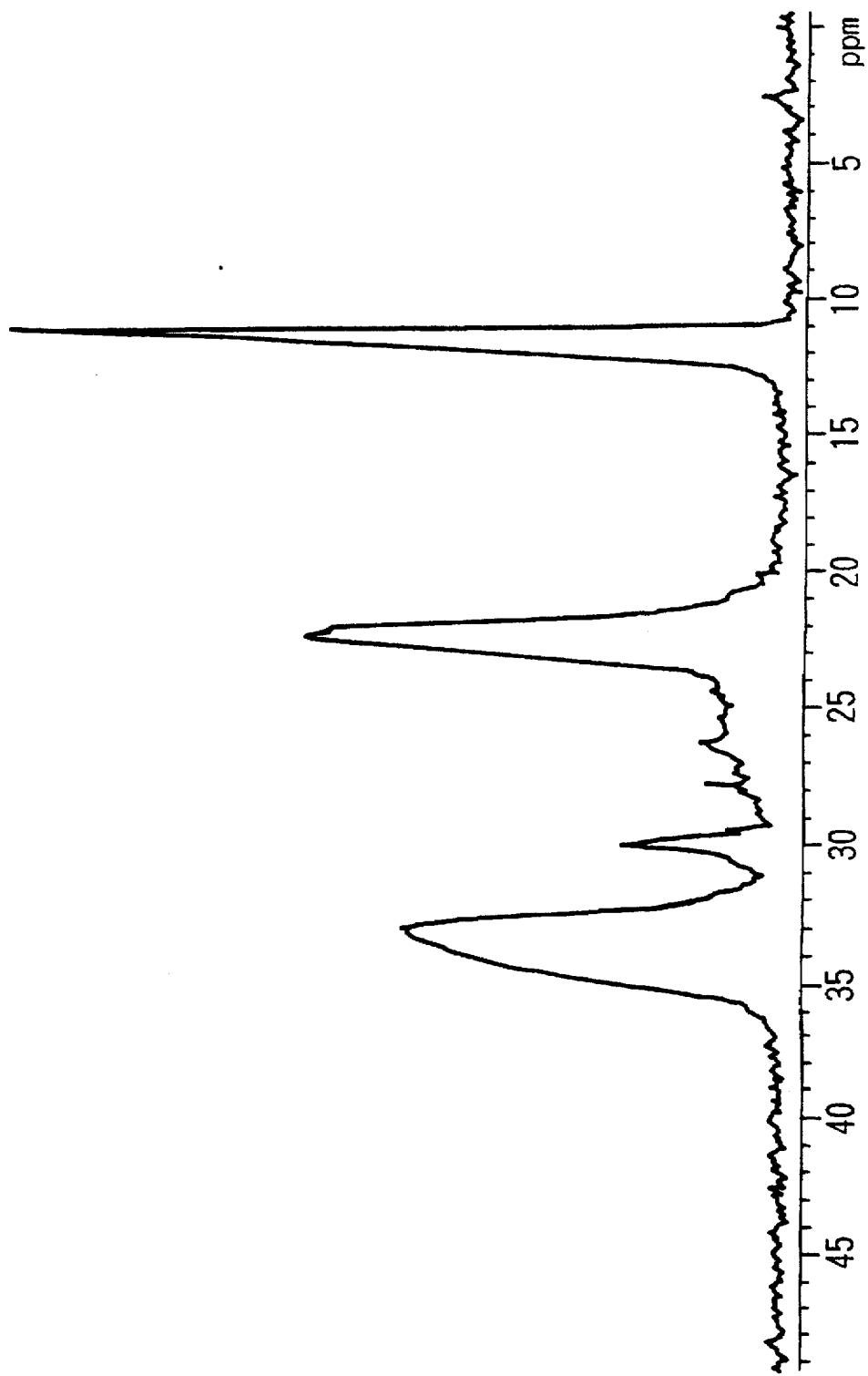
Figure 27:
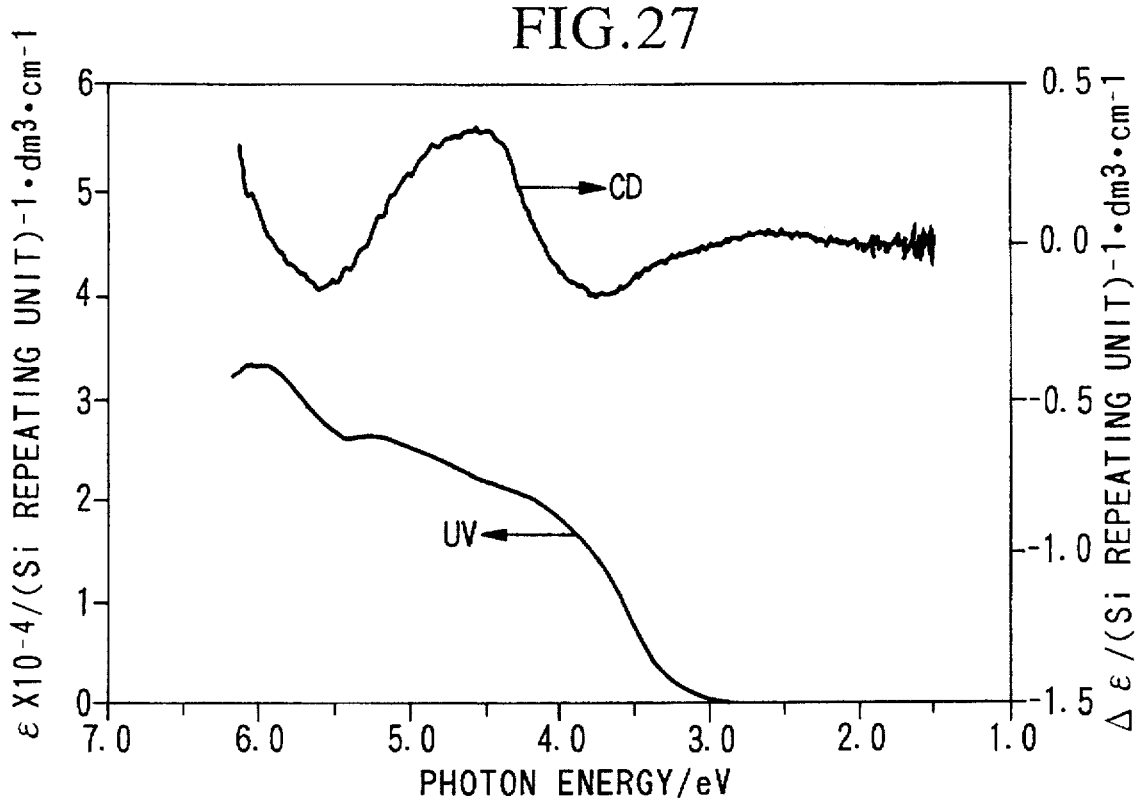
Figure 28:
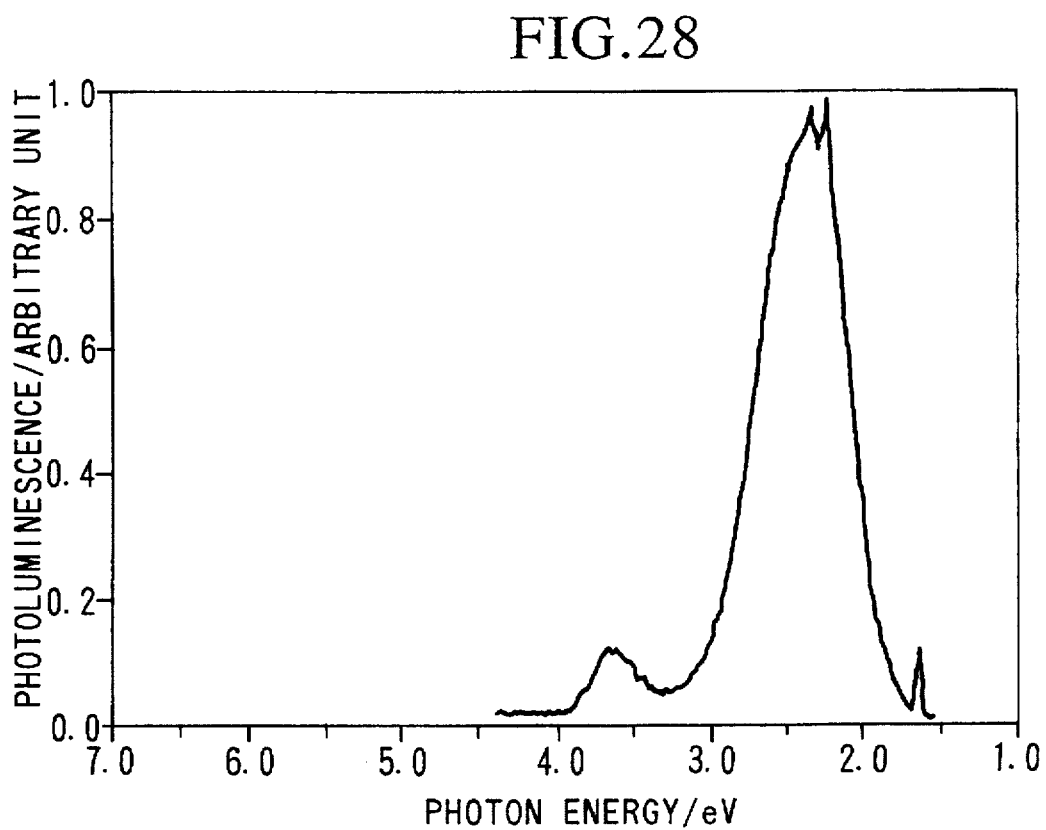
Figure 29:
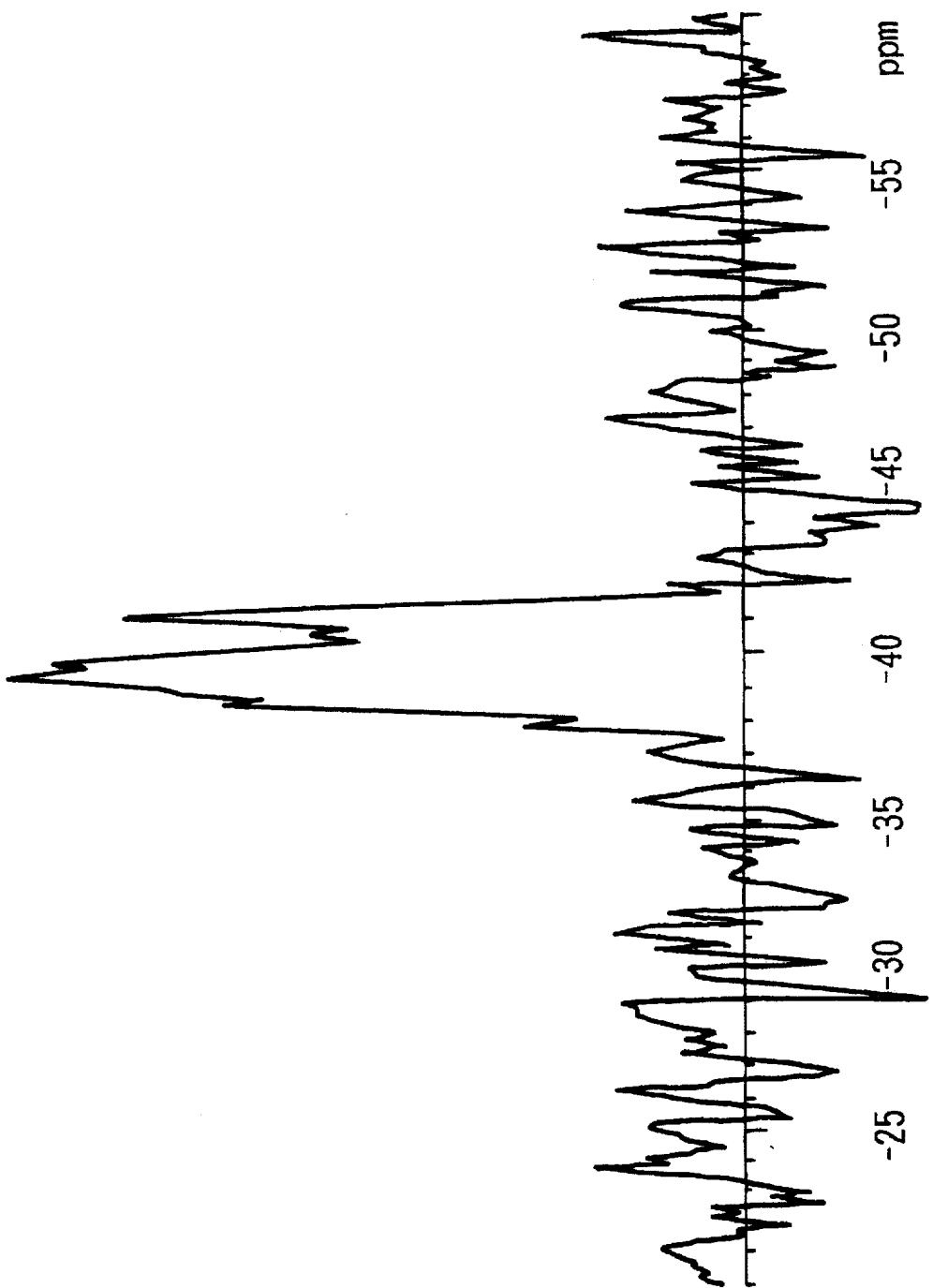
Figure 30:
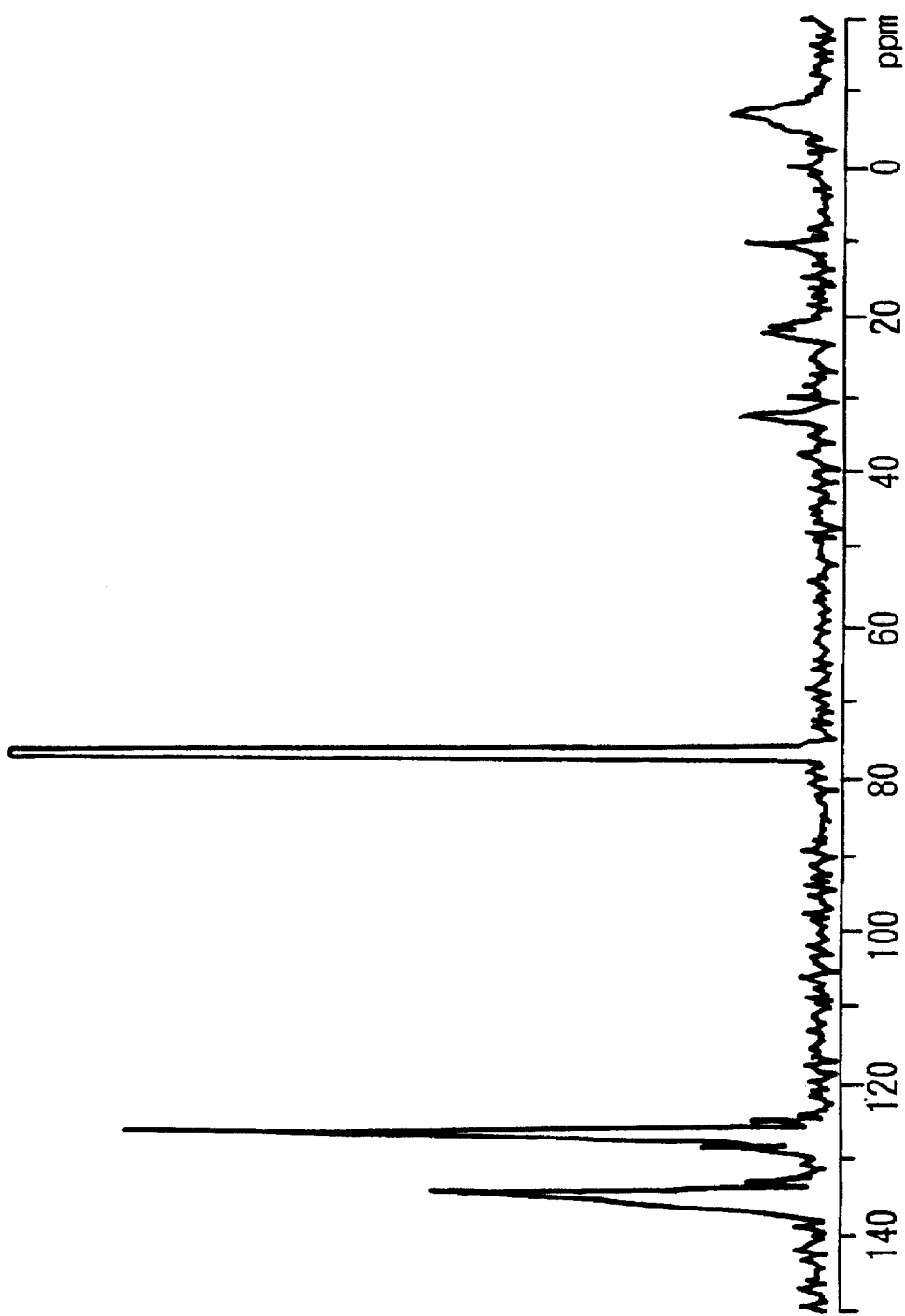
Figure 31:
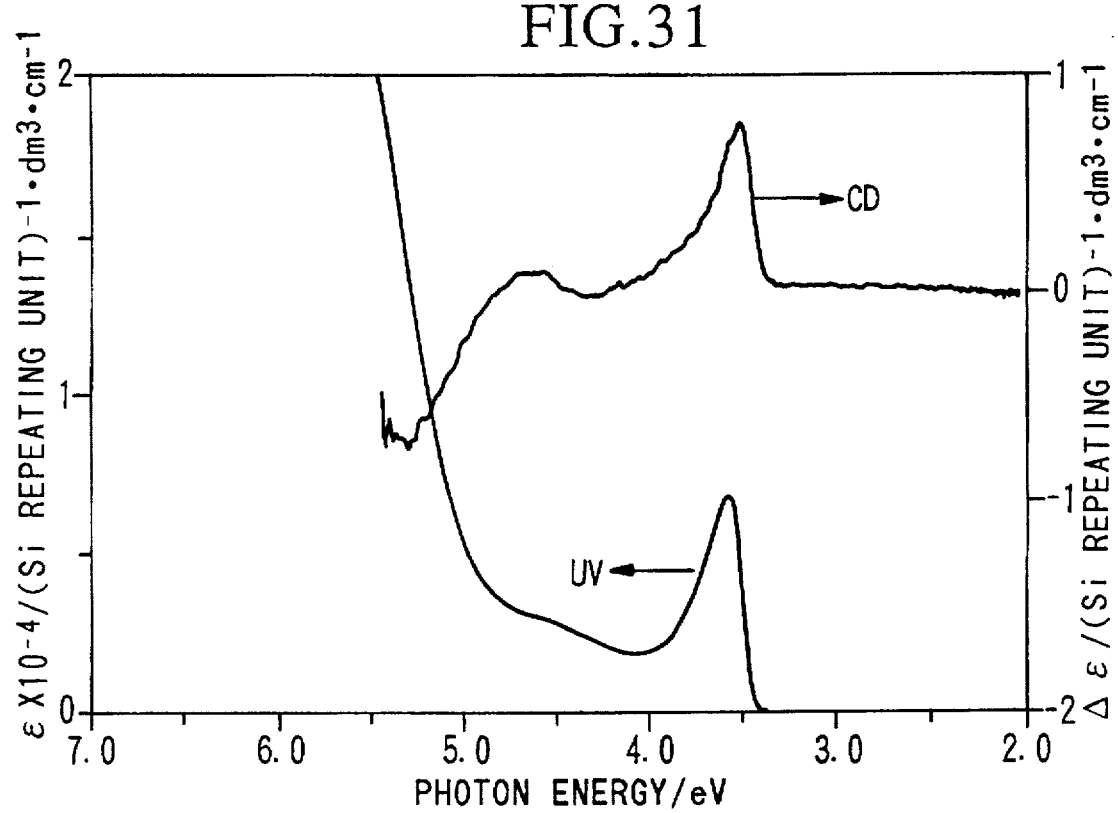
Figure 32:
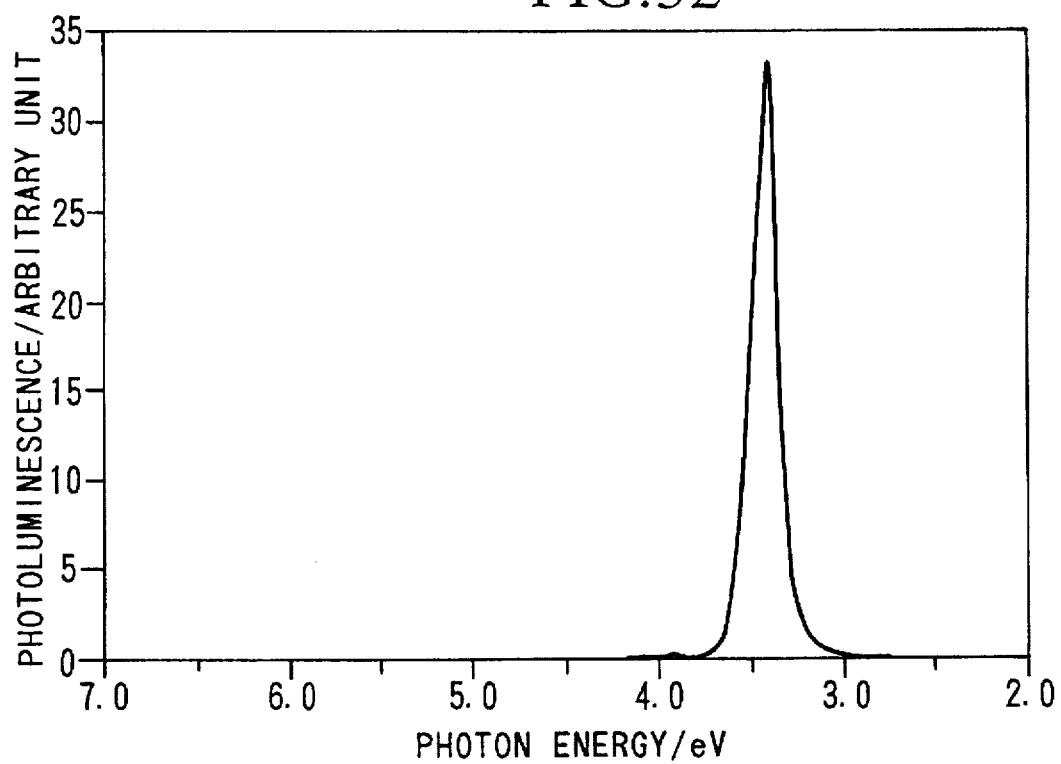
Figure 33:
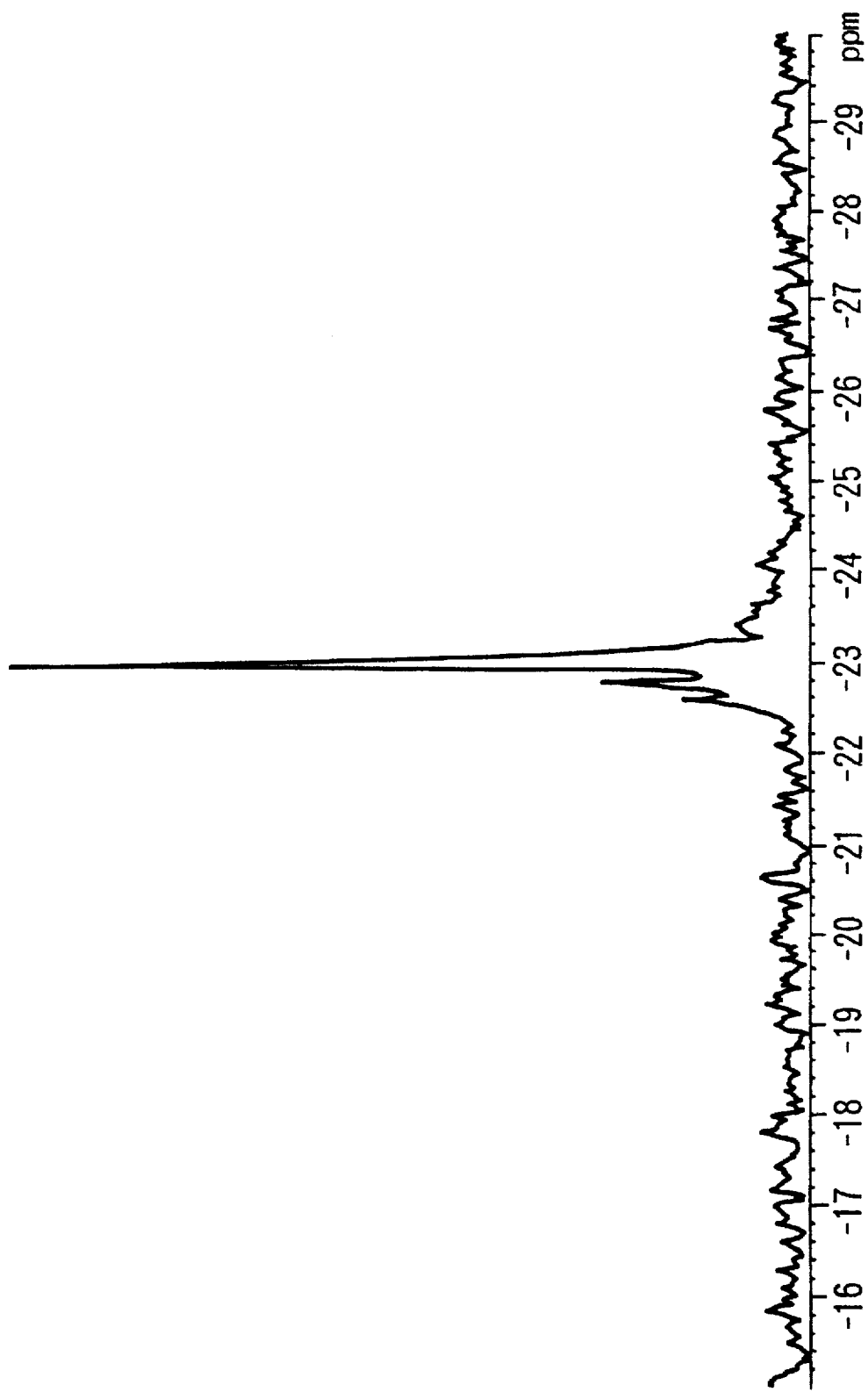
Figure 34:
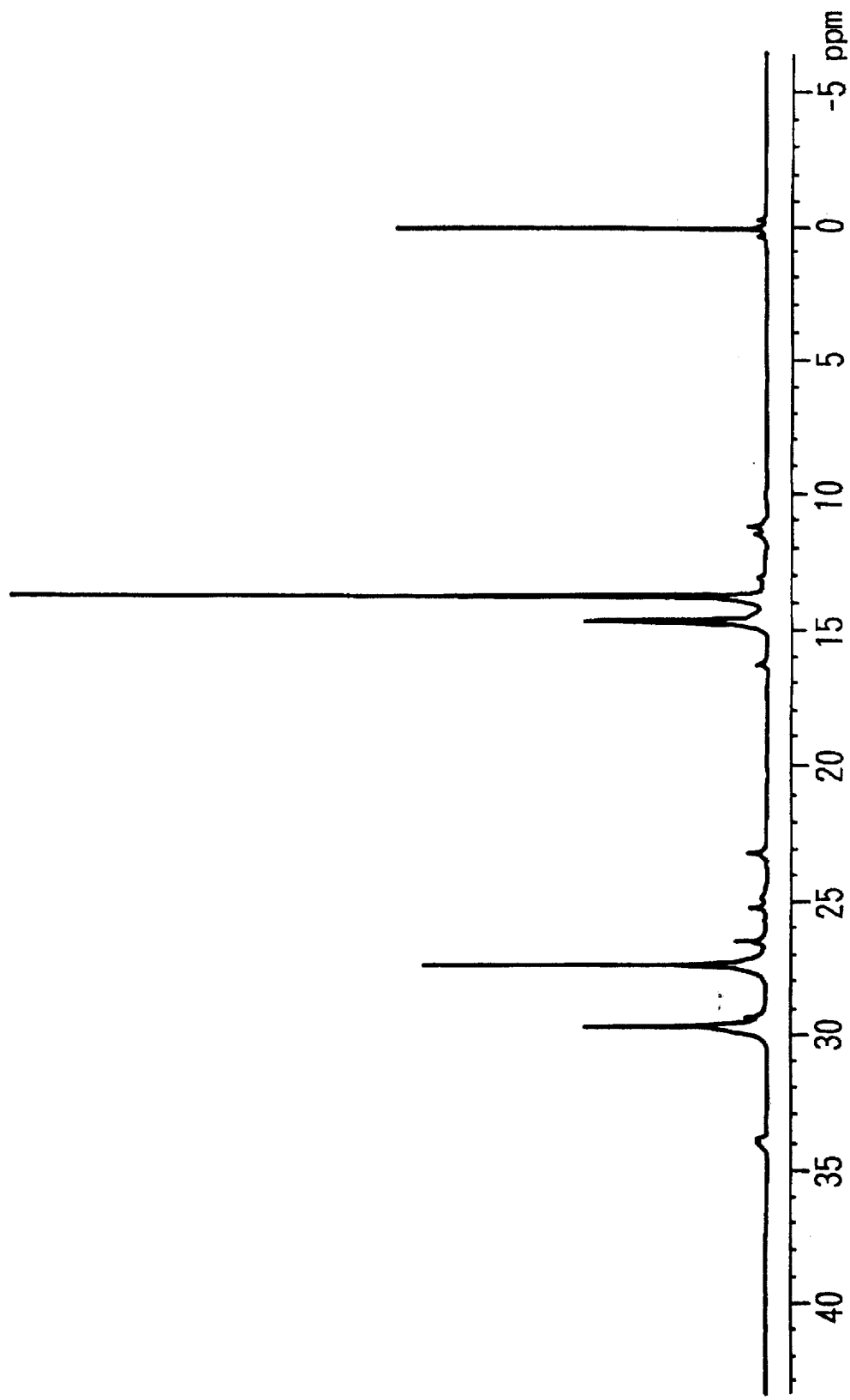
Figure 35:
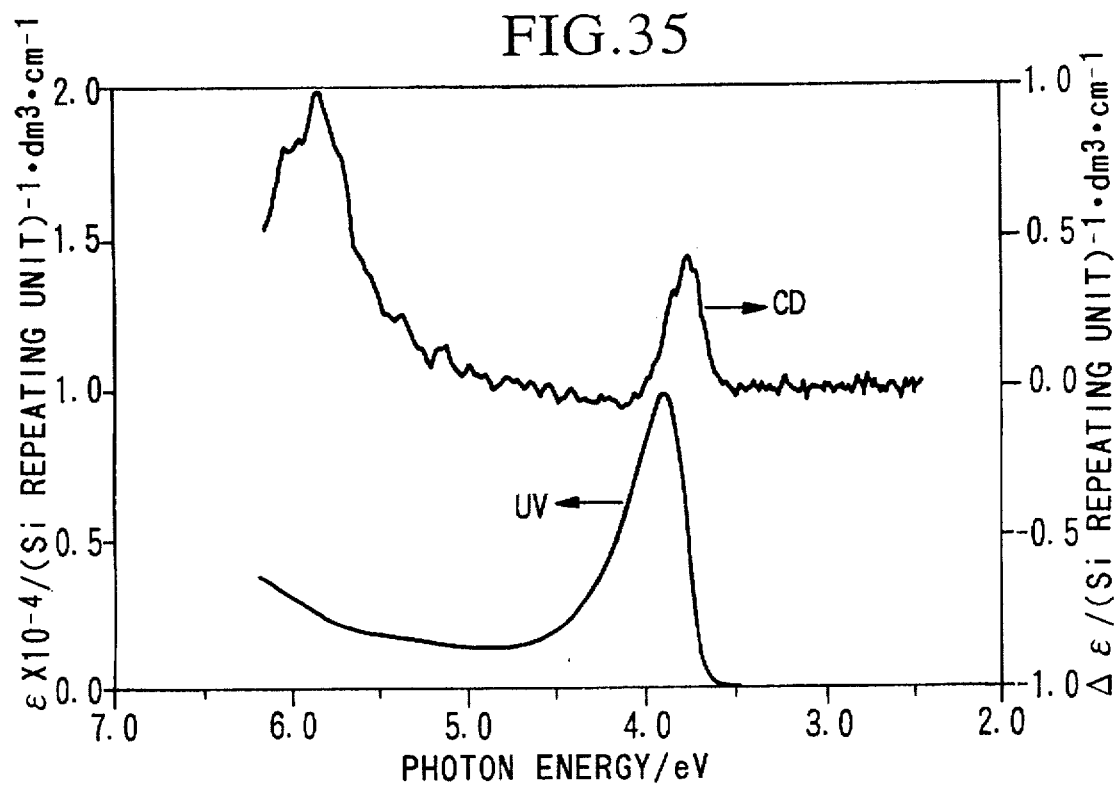
Figure 36:
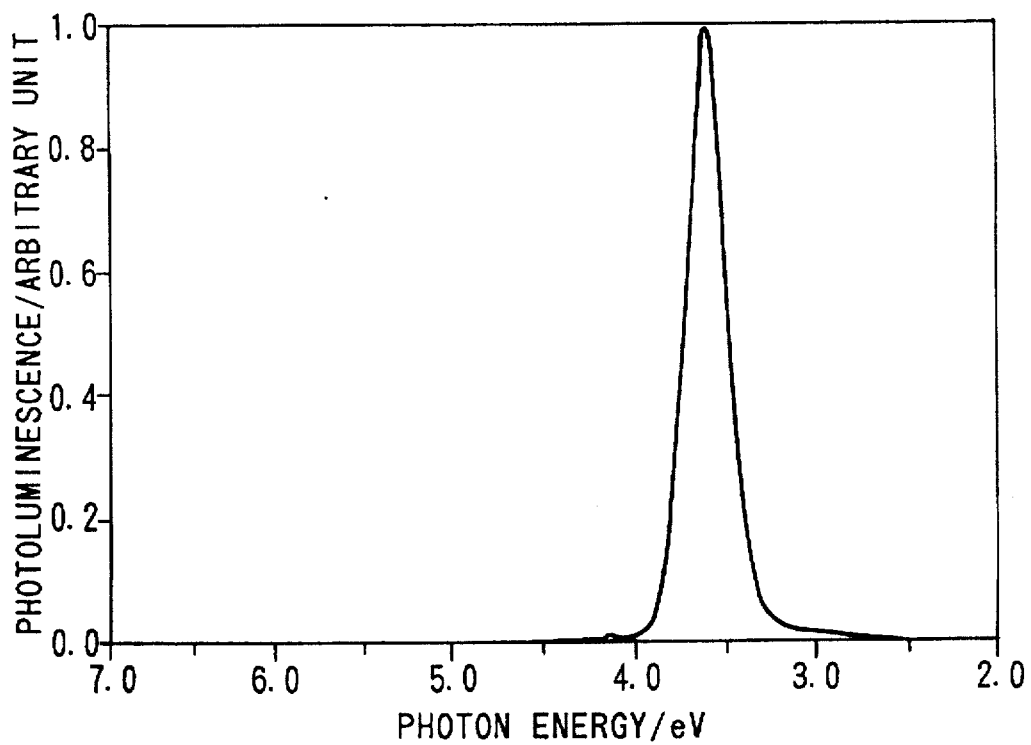
Figure 37:
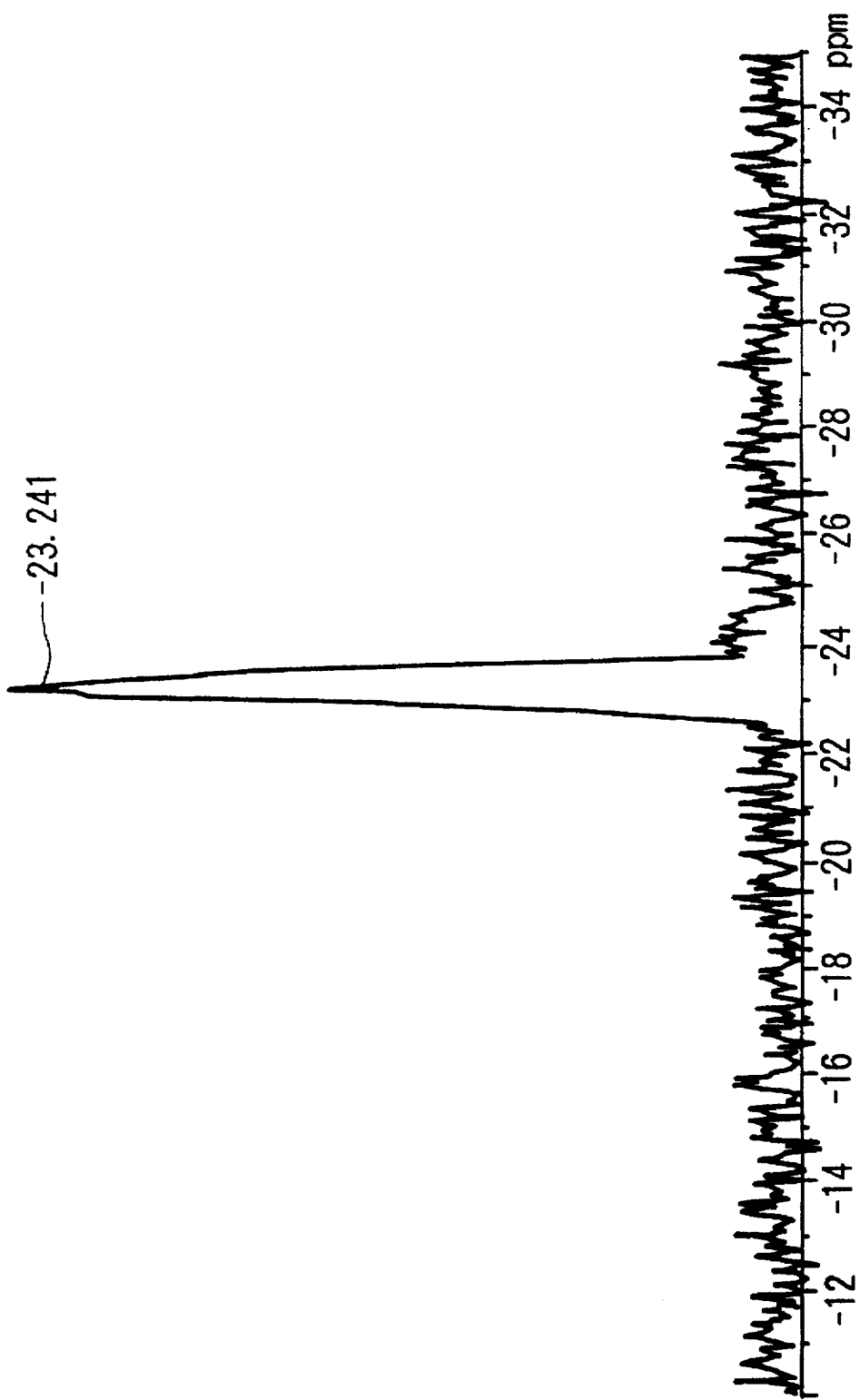
Figure 38:
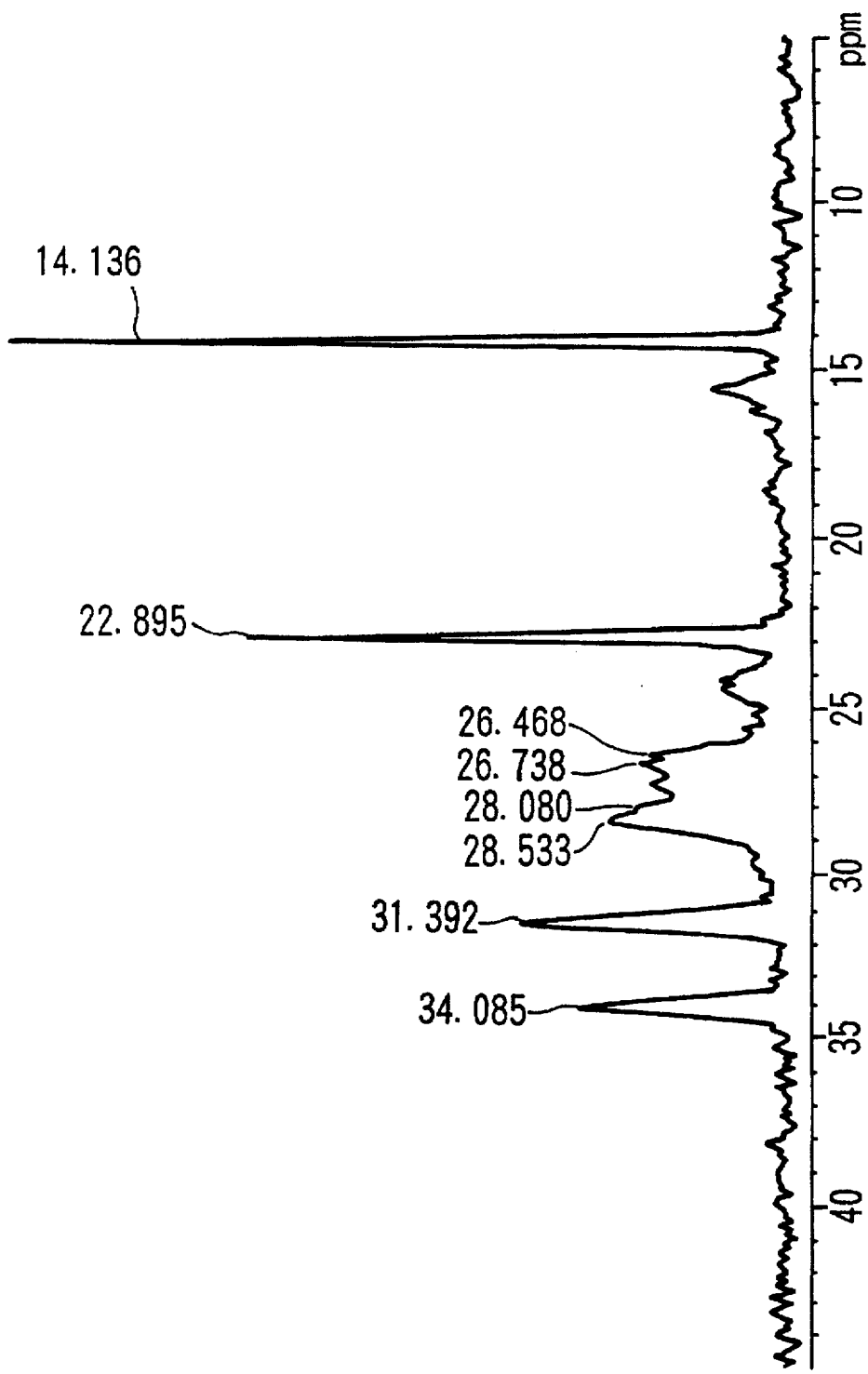
Figure 39:
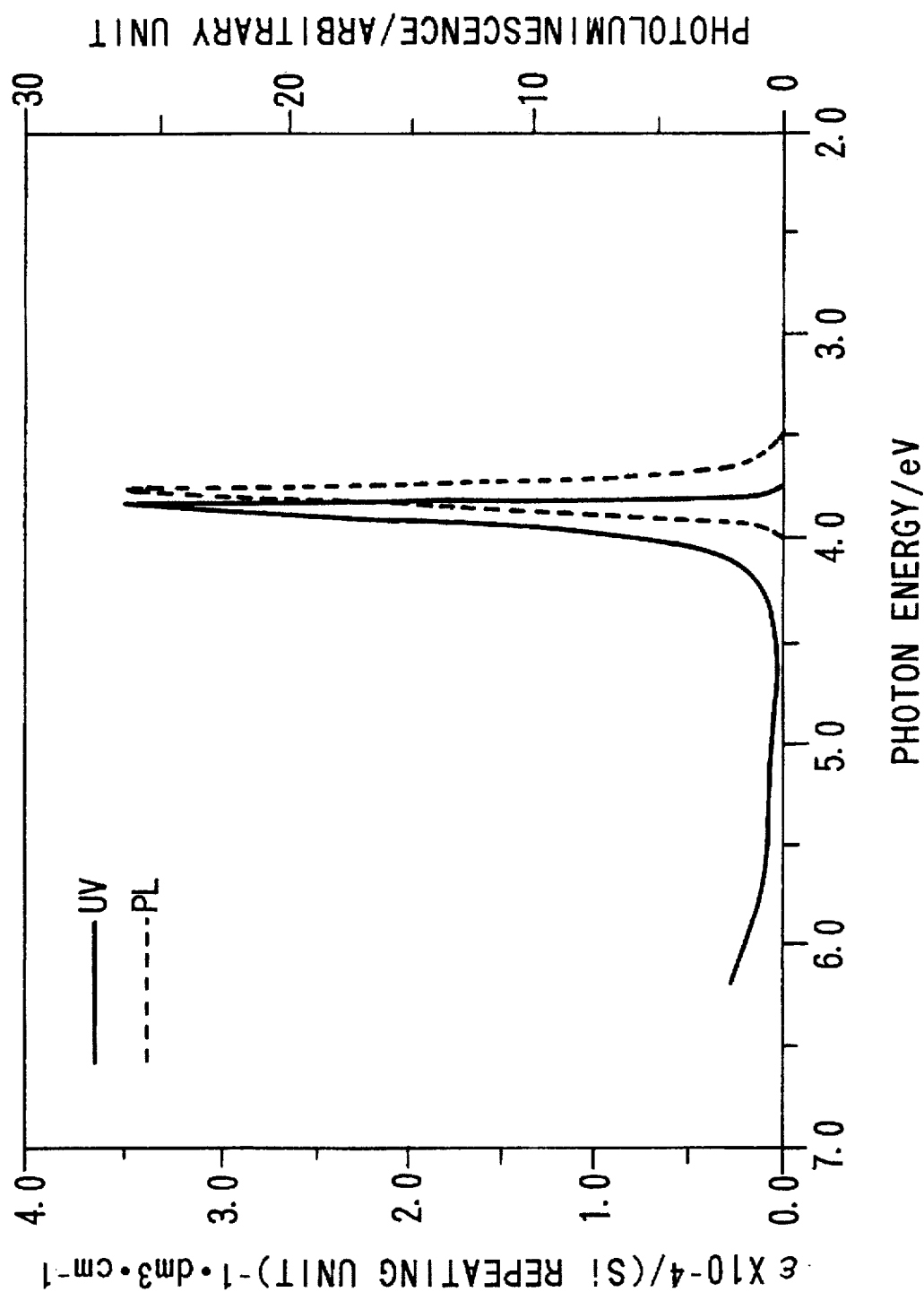
Figure 40:
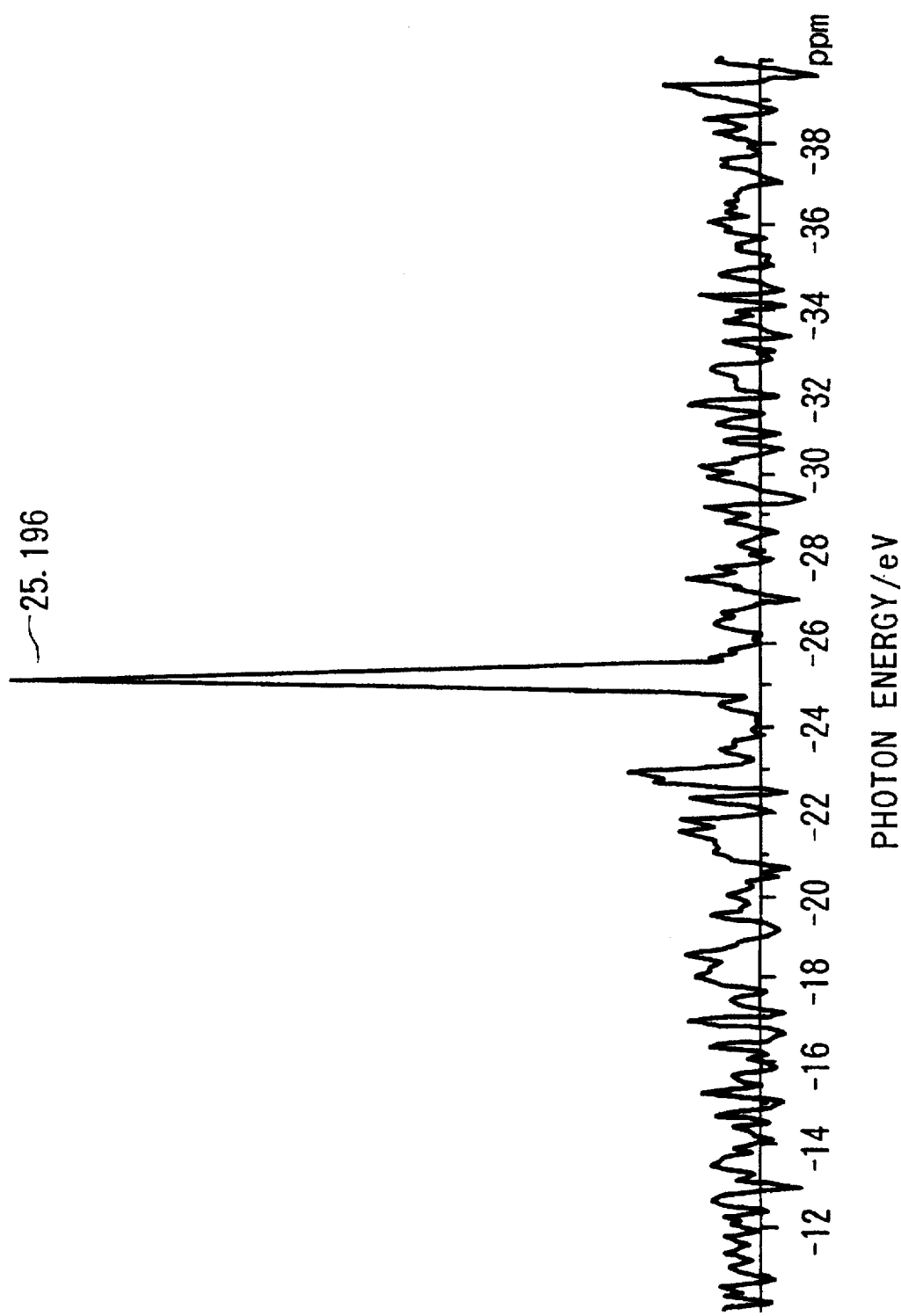
Figure 41:
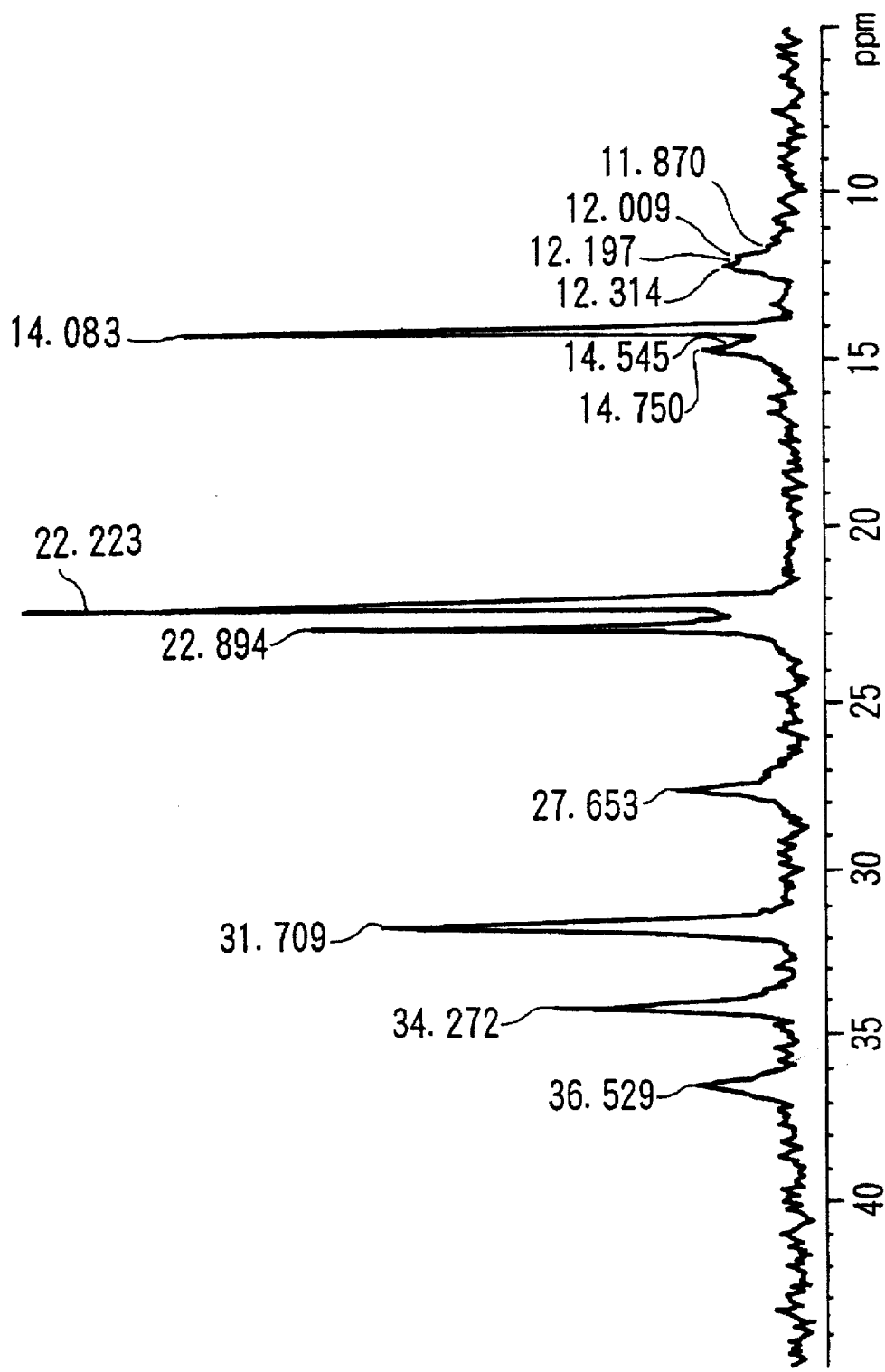
Figure 42:
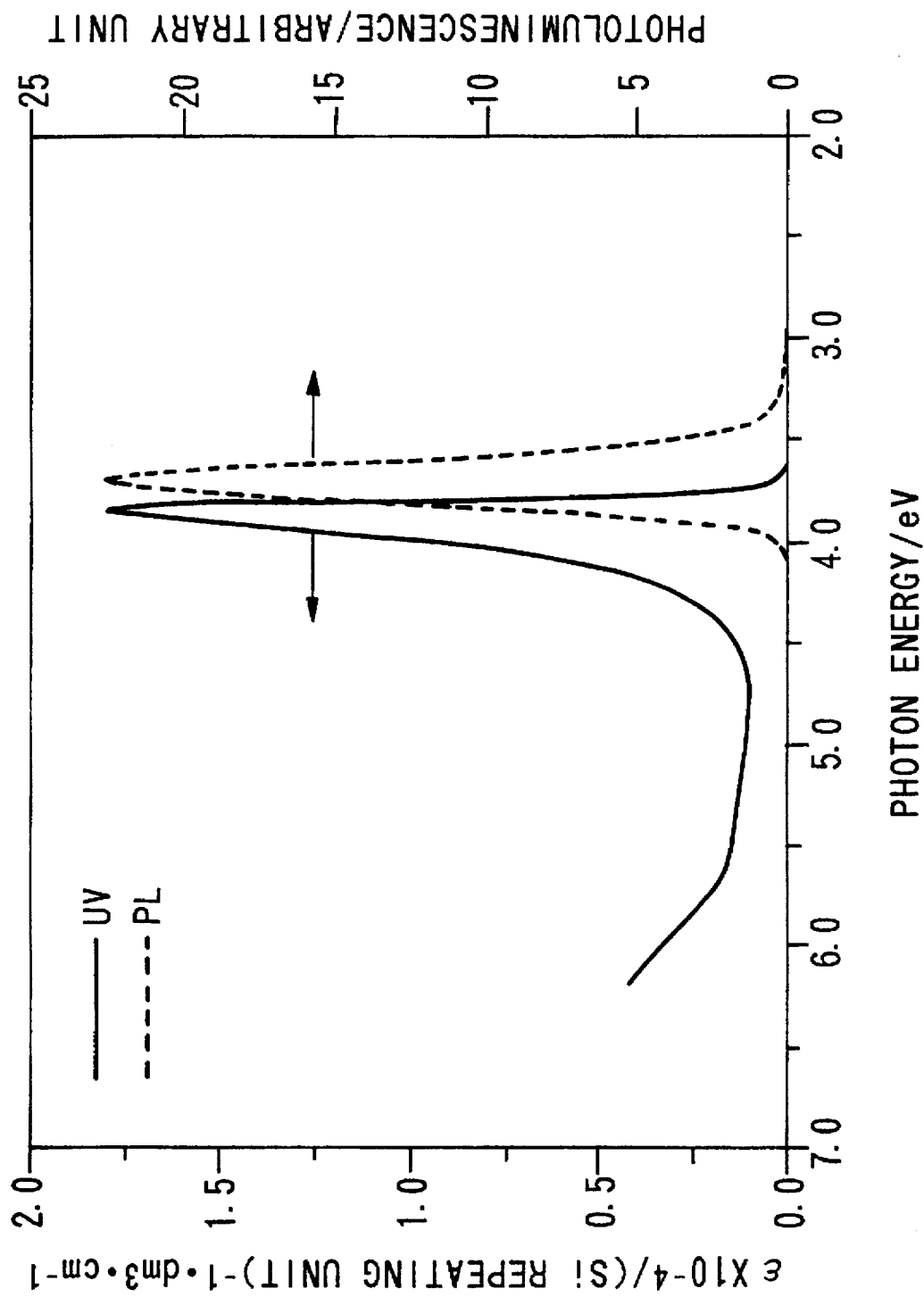
Figure 43:
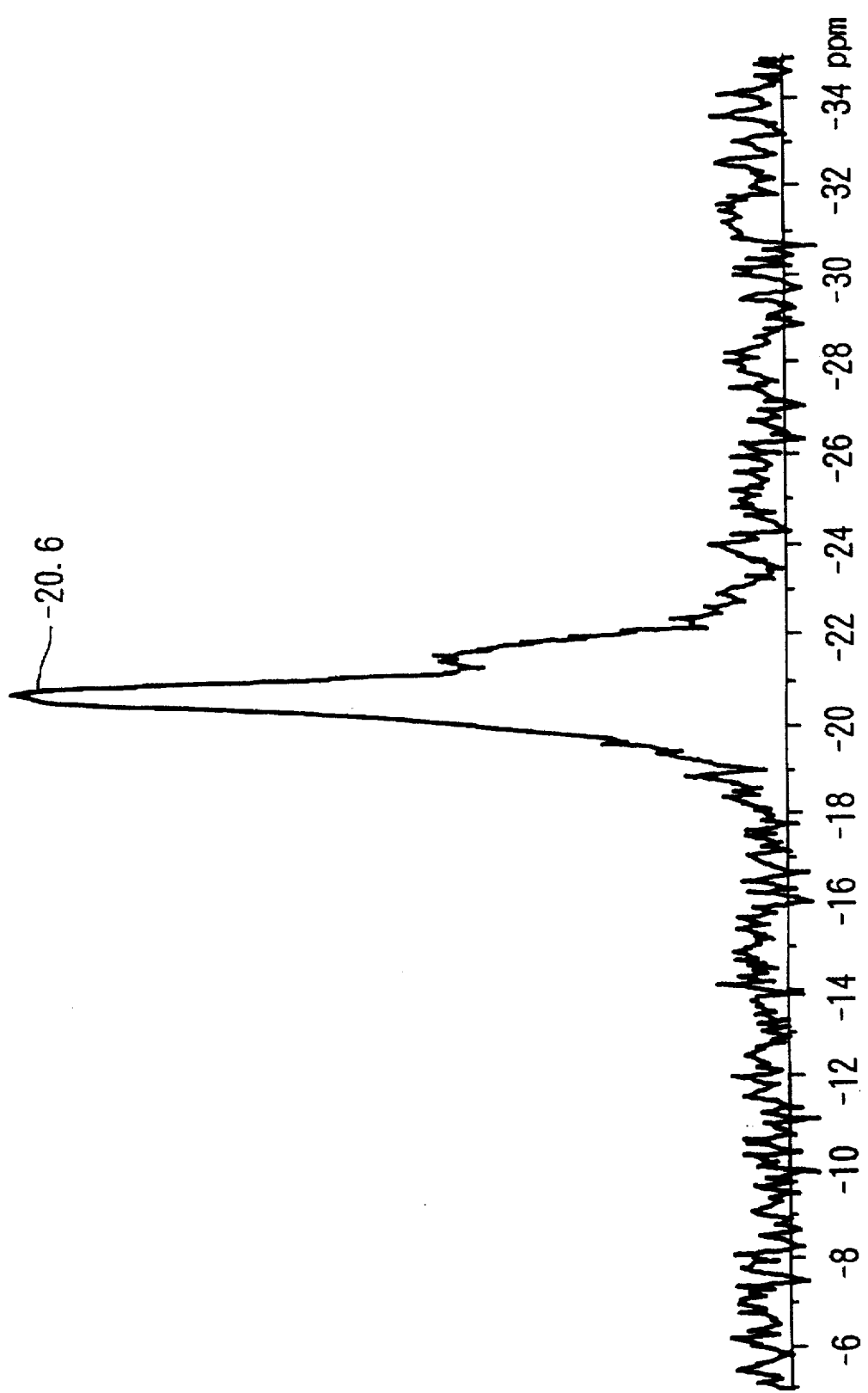
Figure 44:
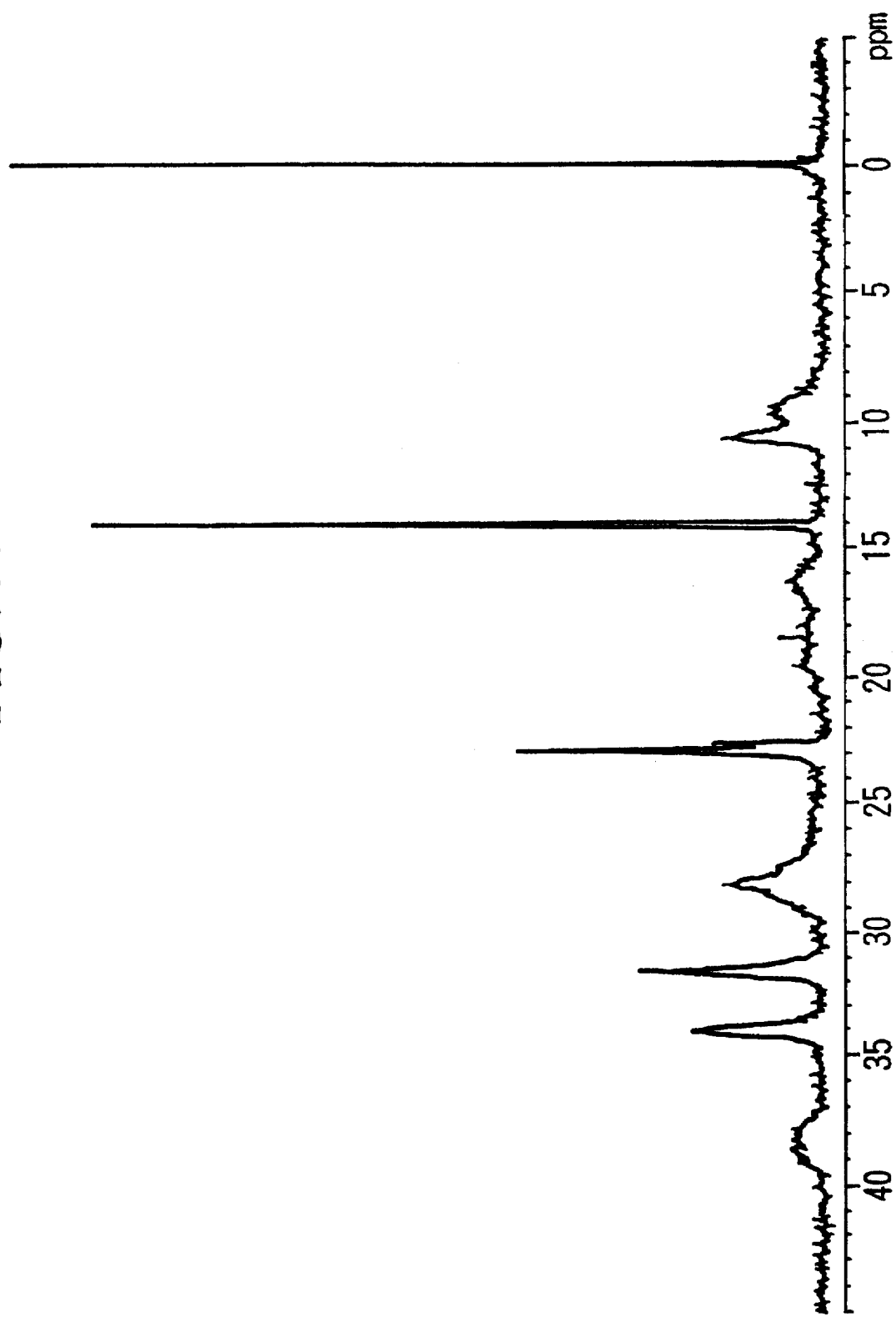
Figure 45:
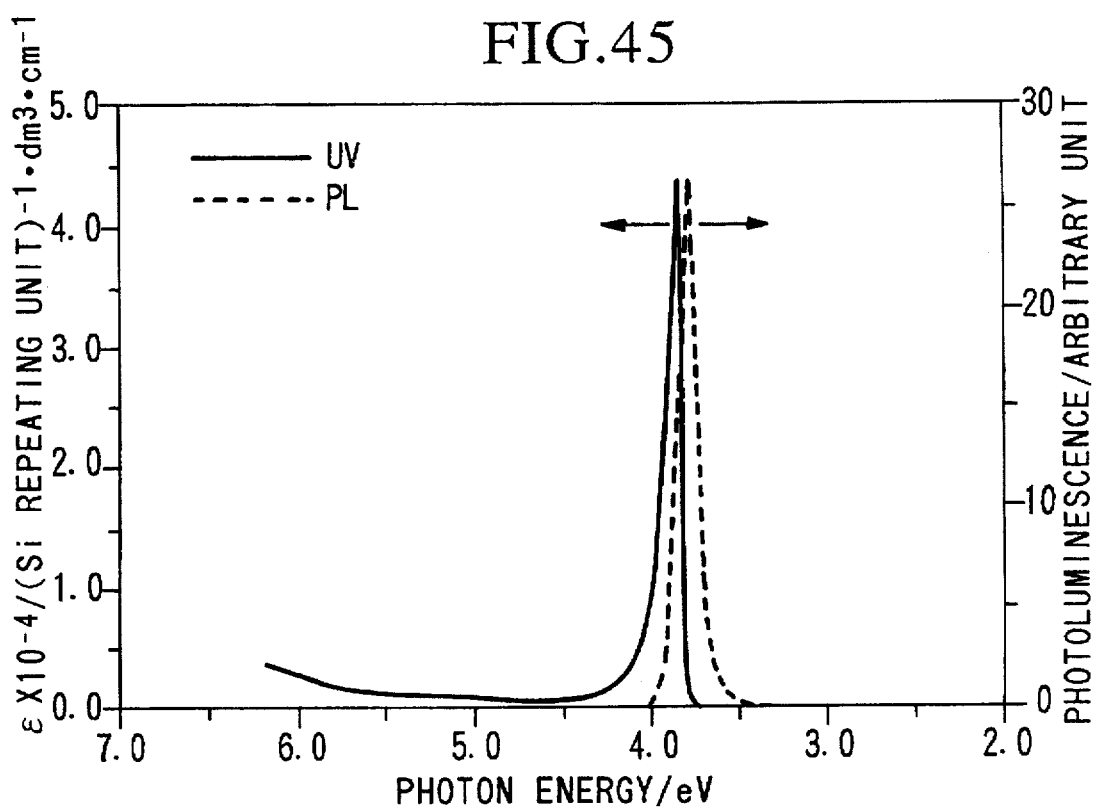
Figure 46:
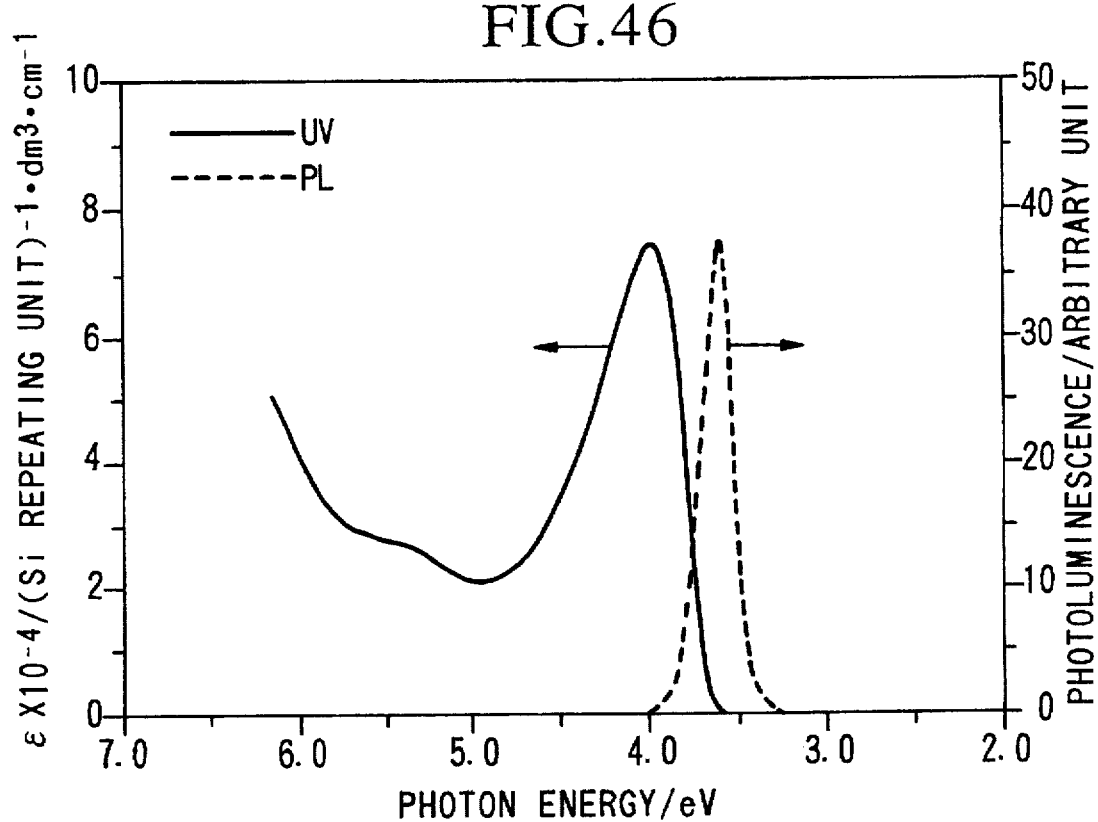
Figure 47:
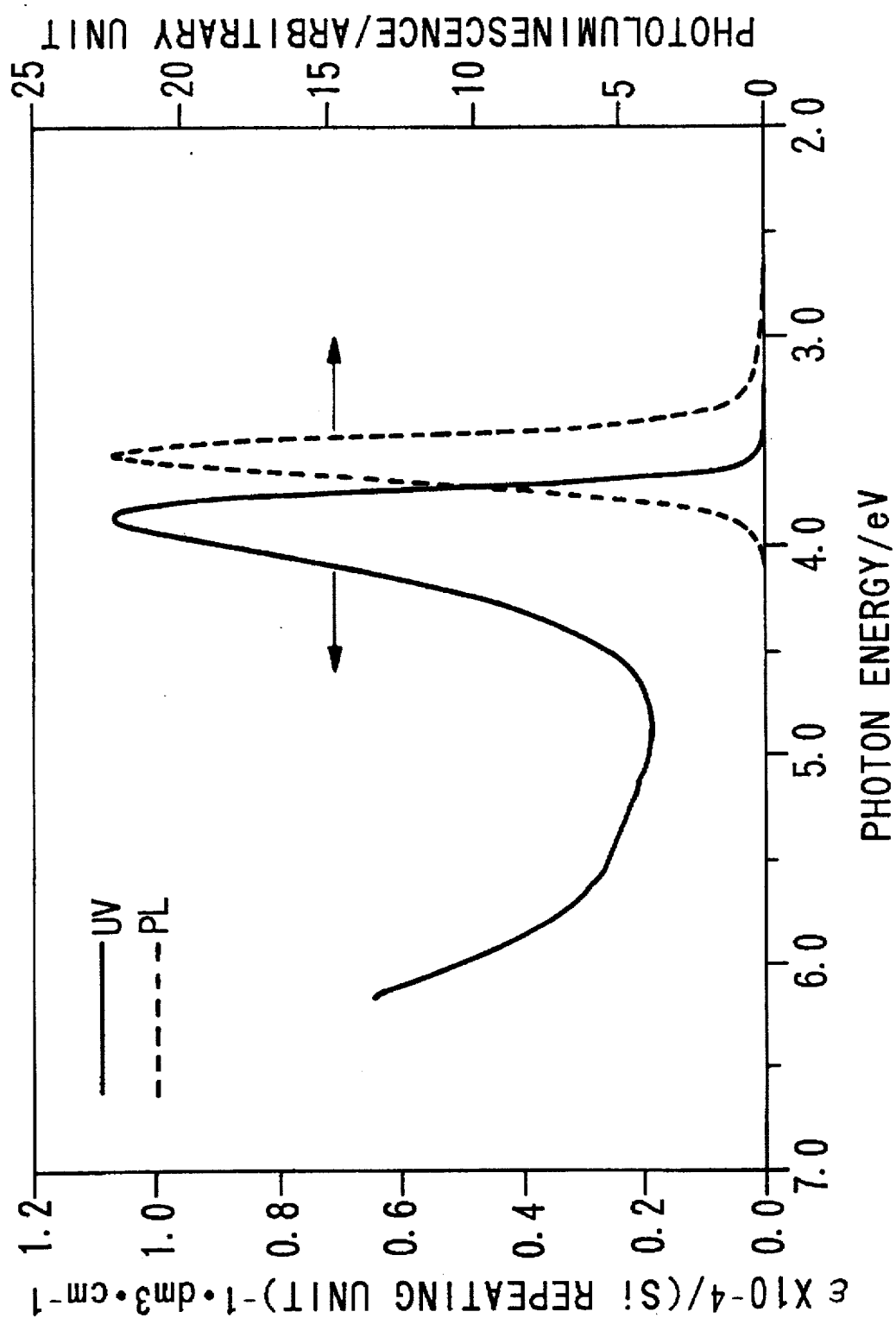

FIG. 20 is a drawing showing both an ultraviolet absorption spectrum and a circular dichroism spectrum (each in i-octane, 20° C.) of the first fractional precipitate of poly[n-octyl-(S)-2-methylbutylsilane] (50650 of weight-average molecular weight and 1.85 of polydispersity) synthesized according to the process described in Example 6;

FIG. 21 is a drawing showing both an ultraviolet absorption spectrum and a circular dichroism spectrum (each in i-octane, 20° C.) of poly[n-nonyl-(S)-2-methylbutylsilane] (40110 of weight-average molecular weight and 2.28 of polydispersity) synthesized according to the process described in Example 6;

FIG. 22 is a drawing showing both an ultraviolet absorption spectrum and a circular dichroism spectrum (each in i-octane, 20° C.) of the first fractional precipitate of poly[n-decyl-(S)-2-methylbutylsilane] (415300 of weight-average molecular weight and 5.6 of polydispersity) synthesized according to the process described in Example 6;

FIG. 23 is a drawing showing both an ultraviolet absorption spectrum and a circular dichroism spectrum (each in i-octane, 20° C.) of the first fraction of poly[n-undecyl-(S)-2-methylbutylsilane] (45600 of weight-average molecular weight and 2.55 of polydispersity) synthesized according to the process described in Example 6;

FIG. 24 is a drawing showing both an ultraviolet absorption spectrum and a circular dichroism spectrum (each in i-octane, 20° C.) of the first fractional precipitate of poly[n-dodecyl-(S)-2-methylbutylsilane] (36400 of weight-average molecular weight and 2.08 of polydispersity) synthesized according to the process described in Example 6;

FIG. 25 is a drawing showing a spectrum of $^{29}$Si-NMR (CDCl$_3$, tetramethylsilane as an internal standard, gated proton decoupling technique) of poly[(S)-2-methylbutylsilyne] (4200 of weight-average molecular weight and 1.8 of polydispersity) obtained in Example 7;

FIG. 26 is a drawing showing a spectrum of $^{13}$C-NMR (CDCl$_3$, tetramethylsilane as an internal standard, proton noise decoupling technique) of poly[(S)-2-methylbutylsilyne] (4200 of weight-average molecular weight and 1.8 of polydispersity) obtained in Example 7;

FIG. 27 is a drawing showing both an ultraviolet absorption spectrum and a circular dichroism spectrum (each in i-octane, 20° C.) of poly[(S)-2-methylbutylsilyne](4200 of weight-average molecular weight and 1.8 of polydispersity) obtained in Example 7;

FIG. 28 is a drawing showing a photoluminescence spectrum (in i-octane, 20° C.) of poly[(S)-2-methylbutylsilyne] (4200 of weight-average molecular weight and 1.8 of polydispersity) obtained in Example 7;

FIG. 29 is a drawing showing a spectrum of $^{29}$Si-NMR (CDCl$_3$, tetramethylsilane as an internal standard, gated proton decoupling technique) of the first fractional precipitate of poly[(methylphenylsilane)$_{90}$-co-{(S)-2-methylbutyl-phenylsilane}$_{10}$] (154000 of weight-average molecular weight and 3.0 of polydispersity) obtained in Example 8;

FIG. 30 is a drawing showing a spectrum of $^{13}$C-NMR (CDCl$_3$, tetramethylsilane as an internal standard, proton noise decoupling technique) of the first fractional precipitate of poly[(methylphenylsilane)$_{90}$-co-{(S)-2-methylbutyl-phenylsilane}$_{10}$] (154000 of weight-average molecular weight and 3.0 of polydispersity) obtained in Example 8;

FIG. 31 is a drawing showing both an ultraviolet absorption spectrum and a circular dichroism spectrum (each in i-octane, 20° C.) of the high molecular weight obtained in Example 8;

FIG. 32 is a drawing showing a photoluminescence spectrum (in i-octane, 20° C.) of the high molecular weight component of poly[(methylphenylsilane)$_{90}$-co-{(S)-2-methylbutyl-phenylsilane}$_{10}$] obtained in Example 8;

FIG. 33 is a drawing showing a spectrum of $^{29}$Si-NMR (CDCl$_3$, tetramethylsilane as an internal standard, gated proton decoupling technique) of the first fractional precipitate of poly[(di-n-butylsilane)$_{90}$-co-[bis{(S)-2-methylbutyl}silane]$_{10}$] obtained in Example 9;

FIG. 34 is a drawing showing a spectrum of $^{13}$C-NMR (CDCl$_3$, tetramethylsilane as an internal standard, proton noise decoupling technique) of the first fractional precipitate of poly[(di-n-butylsilane)$_{90}$-co-[bis{(S)-2-methylbutyl}silane]$_{10}$] obtained in Example 9;

FIG. 35 is a drawing showing both an ultraviolet absorption spectrum and a circular dichroism spectrum (each in i-octane, 20° C.) of the first fractional precipitate of poly[(di-n-butylsilane)$_{90}$-co-[bis{(S)-2-methylbutyl}silane]$_{10}$] obtained in Example 9;

FIG. 36 is a drawing showing a photoluminescence spectrum (in i-octane, 20° C.) of the first fractional precipitate of poly[(di-n-butylsilane)$_{90}$-co-[bis{(S)-2-methylbutyl}silane]$_{10}$] obtained in Example 9;

FIG. 37 is a drawing showing a spectrum of $^{29}$Si-NMR (CDCl$_3$, tetramethylsilane as an internal standard, gated proton decoupling technique) of poly[n-hexyl-i-butylsilane] obtained in Example 13;

FIG. 38 is a drawing showing a spectrum of $^{13}$C-NMR (CDCl$_3$, tetramethylsilane as an internal standard, proton noise decoupling technique) of poly[n-hexyl-i-butylsilane] obtained in Example 13;

FIG. 39 is a drawing showing both an ultraviolet absorption spectrum and a circular dichroism spectrum (each in i-octane, 20° C.) of poly[n-hexyl-i-butylsilane] obtained in Example 13;

FIG. 40 is a drawing showing a spectrum of $^{29}$Si-NMR (CDCl$_3$, tetramethylsilane as an internal standard, gated proton decoupling technique) of poly[n-hexyl-3-methylbutylsilane] obtained in Example 14;

FIG. 41 is a drawing showing a spectrum of $^{13}$C-NMR (CDCl$_3$, tetramethylsilane as an internal standard, proton noise decoupling technique) of poly[n-hexyl-3-methylbutylsilane] obtained in Example 14;

FIG. 42 is a drawing showing both an ultraviolet absorption spectrum and a circular dichroism spectrum (each in i-octane, 20° C.) of poly[n-hexyl-3-methylbutylsilane] obtained in Example 14;

FIG. 43 is a drawing showing a spectrum of $^{29}$Si-NMR (CDCl$_3$, tetramethylsilane as an internal standard, gated proton decoupling technique) of poly[n-hexyl-2-ethylbutylsilane] obtained in Example 15;

FIG. 44 is a drawing showing a spectrum of $^{13}$C-NMR (CDCl$_3$, tetramethylsilane as an internal standard, proton noise decoupling technique) of poly[n-hexyl-2-ethylbutylsilane] obtained in Example 15;

FIG. 45 is a drawing showing both an ultraviolet absorption spectrum and a circular dichroism spectrum (each in i-octane, 20° C.) of poly[n-hexyl-2-ethylbutylsilane] obtained in Example 15;

FIG. 46 is a drawing showing both an ultraviolet absorption spectrum and a circular dichroism spectrum (each in i-octane, 20° C.) of poly[methyl-n-propylsilane] obtained in Comparative Example 1; and FIG. 47 is a drawing showing both an ultraviolet absorption spectrum and a circular dichroism spectrum (each in i-octane, 20° C.) of poly[di-n-hexylsilane] obtained in Comparative Example 2.

DETAILED DESCRIPTION OF THE INVENTION

The present invention provides an organosilicon compound possessing a β-branched alkyl group or a β-branched aralkyl group represented by Formula (I):

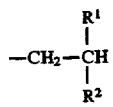   (I)

wherein $R^1$ represents methyl group or ethyl group; $R^2$ represents a C1–C18 alkyl group or aryl group.

The organosilicon compound according to the present invention includes (1) an optically active organosilicon monomer, (2) an optically active homopolymer derived from the monomer defined (1), (3) an optically inactive organosilicon monomer, (4) an optically inactive homopolymer derived from the monomer defined in (3), and (5) an optically active copolymer derived from the optically active organosilicon monomer defined in (1) and the optically inactive organosilicon monomer such as defined in (3).

With regard to organosilicon compounds (1) to (5), detailed descriptions are given hereinafter.

(1) Optically active organosilicon monomer

According to the present invention, an organosilicon monomer represented by Formula (II):

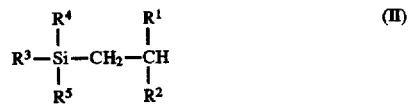   (II)

wherein $R^1$ represents methyl group or ethyl group; $R^2$ represents a C1–C18 alkyl group or aryl group; and $R^3$, $R^4$ and $R^5$, each represent independently Si, Cl, alkyl group, aryl group, or aralkyl group, is provided.

Since the organosilicon monomer represented by Formula (II) is optically active, $R^1$ and $R^2$ are different from each other. For example, $R^1$ is methyl group; $R^2$ is ethyl group; and $R^3$ represents alkyl group, aryl group, or aralkyl group; and $R^4$ and $R^5$, each represent Cl; or $R^3$, $R^4$ and $R^5$, each represent Cl.

With regard to synthesis of optically active organosilicon monomers according to the present invention, detailed descriptions are given hereinafter. A chlorosilane which possesses asymmetric-substituent type of optically active organic substituent having one or two Si—Cl bond is synthesized according to Scheme A as follows:

Scheme A

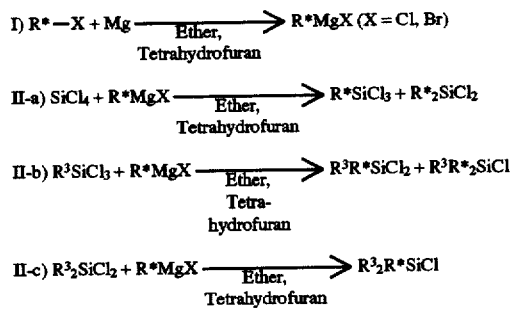

-continued
Scheme A

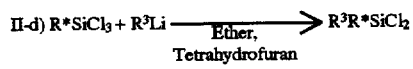

wherein R* represents a chiral branched alkyl group or a chiral branched aralkyl group represented by Formula (I), and $R^3$ is alkyl group, aryl group, or aralkyl group. In other words, as R* group, in Formula (I), $R^1$ and $R^2$ are different from each other.

As $R^3$, there can be mentioned alkyl group including $CH_3$, $C_2H_5$, $n-C_3H_7$, $n-C_4H_9$, $n-C_5H_{11}$, $n-C_6H_{13}$, $n-C_7H_{15}$, $n-C_8H_{17}$, $n-C_9H_{19}$, $n-C_{10}H_{21}$, $n-C_{11}H_{23}$, $n-C_{12}H_{25}$, $i-C_4H_9$, $3-CH_3-C_4H_9$, or the like, aryl group such as phenyl, p-tolyl, or the like, or aralkyl group such as benzyl, β-phenethyl. As R*, a group represented by Formula (VII) is preferred.

   (VII)

With regard to synthesis of a dichlorosilane which possesses a symmetric-substituent type of optically active organic substituent having two Si—Cl bonds or a trichlorosilane which possesses an optically active organic substituent having three Si—Cl bonds is synthesized according to Scheme B as follows:

Scheme B

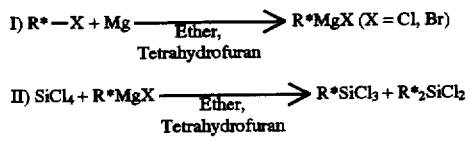

wherein R* has the same meaning defined in Scheme A.

As a chiral organic substituent, (S)-(+)-1-halo-2-methylbutane is advantageous since it is easily available and relatively inexpensive. Using a Grignard reagent derived from this alkylhalide, the corresponding chiral alkylsilane chloride compound can be easily prepared. As a chiral alkylhalide, there can be mentioned not only a compound possessing a chiral center at β-position from a silicon atom, represented by (S)-(+)-1-halo-2-methylbutane, but also a compound possessing a chiral center at an α-position from a silicon atom such as 1-menthyl chloride. In the case of a compound possessing a chiral center at an α-position, the compound is sometimes racemic. Therefore, a chiral alkylhalide possessing a plurality of chiral centers, except at the α-position, is preferred.

As described above, the optically active organochlorosilane represented by Formula (II) can be obtained.

(2) Optically active organosilicon homopolymer

According to the present invention, an organosilicon homopolymer represented by Formula (III):

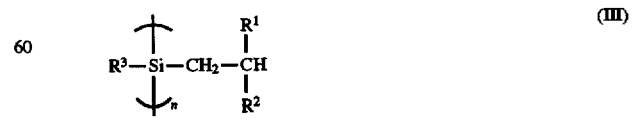   (III)

wherein $R^1$ represents methyl group or ethyl group; $R^2$ represents a C1–C18 alkyl group or aryl group; and $R^3$ represents alkyl group, aryl group, or aralkyl group; and n is an integer of 10 or more, is provided.

In the organosilicon homopolymer represented by Formula (III), for example, $R^1$ is methyl group; $R^2$ is ethyl group; and $R^3$ represents alkyl group, aryl group, or aralkyl group.

Such optically active organosilicon homopolymers can be synthesized by virtue of a sodium-mediated coupling reaction of a dichlorosilane possessing an optically active substituent using an Na metal, according to the following Scheme C or D:

Scheme C

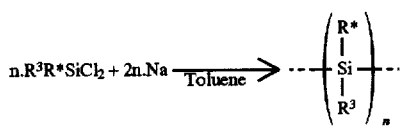

Scheme D

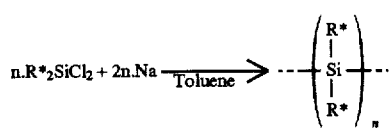

wherein $R^*$ and $R^3$ have the same meanings defined in Scheme A.

In view of simplicity for synthesis, a combination between alkyl group including $CH_3$, $C_2H_5$, n-$C_3H_7$, n-$C_4H_9$, n-$C_5H_{11}$, n-$C_6H_{13}$, n-$C_7H_{15}$, n-$C_9H_{19}$, n-$C_{10}H_{21}$, n-$C_{11}H_{23}$, n-$C_{12}H_{25}$, i-$C_4H_9$, or the like, or aralkyl group such as β-phenethyl, or the like as $R^3$ and (S)-2-methylbutyl as $R^*$ is preferred. As the chiral center of the dichlorosilane possessing the optically active organic substituent is at β-position, it is impossible to be racemic upon the sodium-mediated coupling reaction. Furthermore, the steric hindrance between the silicon monomers on the condensation reaction is relatively small. For these reasons, from the dichlorosilane possessing the optically active organic substituent, an optically active chain-like organopolysilane having a high molecular weight can be obtained. According to our information, since relatively compact alkyl groups, i.e., methyl group and ethyl group, are bound to the chiral carbon atom at the β-position, by virtue of this steric factor, the chain-like backbone of the organopolysilane obtained in Scheme C or D may possess a one-handed helical structure with a constant pitch.

According to the present invention, an organosilicon homopolymer represented by Formula (IV):

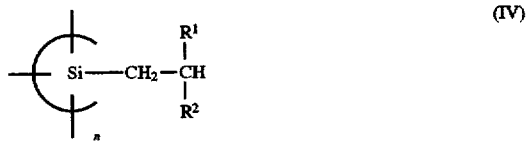

wherein $R^1$ represents methyl group or ethyl group; $R^2$ represents a C1–C18 alkyl group or aryl group; and n is an integer of 10 or more, is provided.

In the organosilicon homopolymer represented by Formula (IV), for example, $R^1$ is methyl group; and $R^2$ is ethyl group.

A network type of optically active organosilicon homopolymer can be synthesized by virtue of a sodium-mediated coupling reaction of a trichlorosilane possessing an optically active substituent using an Na metal, according to the following Scheme E:

Scheme E

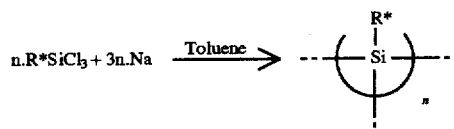

wherein $R^*$ has the same meaning as defined in Scheme A.

As a trichlorosilane possessing an optically active organic substituent, [(S)-2-methylbutyl]trichlorosilane is advantageous because of the simplicity of synthesis. Since the trichlorosilane possessing an optically active organic substituent has a chiral center at the β-position, a racemization does not occur upon the sodium-mediated coupling reaction. In addition, the steric hindrance between the silicon monomers on the condensation reaction is not so large. For this reason, an optically active network-type of organopolysilane having a high molecular weight can be obtained.

(3) Optically inactive organosilicon monomer

According to the present invention, an optically inactive organosilicon monomer represented by Formula (II):

$$R^3-\underset{\underset{R^5}{|}}{\overset{\overset{R^4}{|}}{Si}}-CH_2-\underset{\underset{R^2}{|}}{\overset{\overset{R^1}{|}}{CH}} \qquad (II)$$

wherein both $R^1$ and $R^2$ represent methyl group or ethyl group; and $R^3$, $R^4$ and $R^5$, each represent independently Si, Cl, alkyl group, aryl group, or aralkyl group, is provided.

As the organosilicon monomer represented by Formula (II) is not optically active, $R^1$ and $R^2$ are the same groups. For example, both $R^1$ and $R^2$ represent methyl group or ethyl group; $R^3$ represents alkyl group, aryl group, or aralkyl group; and $R^4$ and $R^5$, each represent Cl.

With regard to synthesis of optically inactive organosilicon monomer according to the present invention, detailed descriptions are given hereinafter. A dichlorosilane which possesses an asymmetric-substituent type of optically active organic substituent including an achiral branched alkyl group and a dichlorosilane which possesses a symmetric-substituent type of optically active organic substituent including an achiral branched alkyl group are synthesized according to Scheme F as follows:

Scheme F

I) $R'-X + Mg \xrightarrow[\text{Tetrahydrofuran}]{\text{Ether,}} R'MgX$ (X = Cl, Br)

II-a) $SiCl_4 + R'MgX \xrightarrow[\text{Tetrahydrofuran}]{\text{Ether,}} R'_2SiCl_2$ II-b) $R^3SiCl_3 + R'MgX \xrightarrow[\text{Tetrahydrofuran}]{\text{Ether,}} R^3R'SiCl_2$ wherein R' represents an achiral branched alkyl group or an achiral branched aralkyl group represented by Formula (I) and $R^3$ is alkyl group, aryl group, or aralkyl group. In other words, as the R' group, in Formula (I), $R^1$ and $R^2$ are the same groups.

As $R^3$, there can be preferably mentioned alkyl group including $C_2H_5$, n-$C_3H_7$, n-$C_4H_9$, n-$C_5H_{11}$, n-$C_6H_{13}$, n-$C_7H_{15}$, n-$C_8H_{17}$, n-$C_9H_{19}$, n-$C_{10}H_{21}$, n-$C_{11}H_{23}$, n-$C_{12}H_{25}$, or the like. As R', a group represented by Formula (VIII), i.e., i-butyl group or 2-ethylbutyl group, is preferred.

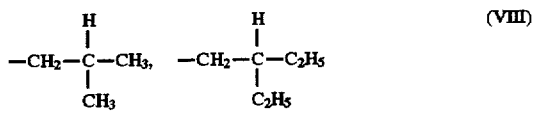
(VIII)

(4) Optically inactive organosilicon homopolymer

According to the present invention, organosilicon homopolymer represented by Formula (V):

(V)

wherein both $R^1$ and $R^2$ represent methyl group or ethyl group; and $R^3$ represents Si, Cl, alkyl group, aryl group, or aralkyl group, is provided.

In the organosilicon homopolymer represented by Formula (V), for example, both $R^1$ and $R^2$ represent methyl group or ethyl group; and $R^3$ represents alkyl group, aryl group, or aralkyl group.

Such optically inactive organosilicon homopolymers can be synthesized by virtue of a sodium-mediated coupling reaction of a dichlorosilane possessing an achiral branched alkyl group using an Na metal, according to the following Scheme G or H:

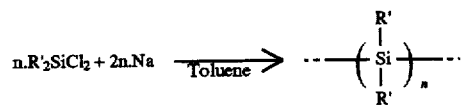

wherein R' and $R^3$ have the same meanings defined in Scheme F.

In view of simplicity for synthesis, a combination between alkyl group including $C_2H_5$, n-$C_3H_7$, n-$C_4H_9$, n-$C_5H_{11}$, n-$C_6H_{13}$, n-$C_7H_{15}$, n-$C_8H_{17}$, n-$C_9H_{19}$, n-$C_{10}H_{21}$, n-$C_{11}H_{23}$, n-$C_{12}H_{25}$, or the like as $R^3$ and i-butyl or 2-ethylbutyl, possessing a β-branched structure, as R' is preferred. Since an organodichlorosilane having a combination between a β-branched structure and n-alkyl group structure possesses a relatively small steric hindrance between silicon monomers upon the sodium-mediated coupling reaction, a chain-like organopolysilane possessing high molecular weight and an increased absorption intensity of the backbone can be obtained. According to our information, since a relatively compact alkyl group, i.e., methyl group or ethyl group, is bound to the chiral carbon atom at the b-position, by virtue of this steric factor, the chain-like backbone of the organopolysilane obtained in Scheme G or H may possess a one-handed helical structure with a constant pitch.

On the other hand, in the case of an α-branched structure, e.g. i-propyl group, instead of a β-branched structure, the steric hindrance is extremely high. For this reason, the resulting organopolysilane according to the process in Scheme G or H possesses low polymeric properties such as an extremely low molecular weight (1000 or lower), 300 nm to 320 nm of the absorption maximum of the backbone, and an extremely broad absorption width.

(5) Optically active organosilicon copolymer

According to the present invention, an organosilicon copolymer represented by Formula (VI):

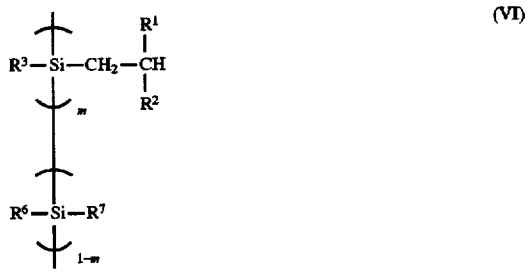
(VI)

wherein $R^1$ represents methyl group or ethyl group; $R^2$ represents a C1–C18 alkyl group or aryl group; $R^3$, $R^4$, and $R^5$, each represent independently Si, Cl, alkyl group, aryl group, or aralkyl group; $R^6$ and $R^7$, each represent independently alkyl group, aryl group, or aralkyl group; and 0.01<m<1 is provided.

The optically active organosilicon copolymer represented by Formula (VI) is derived from an optically active silane compound and an optically inactive silane compound.

Examples 8 and 9 described below show the synthesis examples of an optically active organopolysilane (copolymer) by Na-condensation of chlorosilane monomer including an optically active organic substituent which possesses a relatively small steric hindrance and dichlorosilane monomer possessing an optically inactive organic substituent.

In the case where the optically active organic substituent of the monomer possesses a relatively large steric hindrance, i.e., the substituent being a phenyl group, benzyl group, (S)-2-methylbutyl group, or the like, the desired optically active organopolysilane possesses a low degree of polymerization or cannot be obtained, upon the Na-condensation of the monomer. In this case, by virtue of copolymerization between a dichlorosilane possessing at least one optically active organic substituent and a chlorosilane possessing an optically inactive organic substituent which has a small steric hindrance, an optically active organopolysilane copolymer can be synthesized. It is preferred that the ratio of the optically active dichlorosilane be in the range of 0.01 parts by mole to 0.50 parts by mole. In Examples 8 and 9, m is 0.1.

EXAMPLES

The present invention is illustrated by the following examples. However, it should be understood that the present invention is not limited to the specific details of these examples.

Example 1

Synthesis of Methyl[(S)-2-methylbutyl] dichlorosilane.

Anhydrous tetrahydrofuran (125 mL) was put into a reactor with magnesium (9.5 g, 0.41 mol) and molecular sieves 4A which had been dehydrated and deaerated, followed by charging of argon gas. A small amount of iodine was slowly added to the mixture. (S)-(+)-1-bromo-2-methylbutane (4.5 g, 0.03 mol) was added dropwise to the slowly stirred mixture. In addition, (S)-(+)-1-chloro-2- methylbutane (36 g, 0.34 mol) was added dropwise to the stirred mixture so that the reaction mixture was gradually refluxed. After the reaction was complete, the obtained Grignard reagent was transferred to a dropping funnel. The Grignard reagent was added dropwise to a solution being stirred containing methyltrichlorosilane (80 g, 0.54 mol) in anhydrous diethyl ether (150 mL) in another reactor which had been dehydrated and deaerated, followed by charging of argon gas, at 2° C.–5° C. The reaction mixture was then stirred overnight at room temperature. Hexane (500 mL) was added to the reaction mixture, and the resulting mixture was filtered under pressure, followed by fractional distillation of the filtrate to provide the desired product.

Main fraction:

Boiling point 78° C.–79° C./20 mmHg.

Yield 20.5 g (30%).

$^{29}$Si-NMR (CDCl$_3$, tetramethylsilane as an internal standard, gated proton decoupling technique) 32.5 ppm.

$^{13}$C-NMR (CDCl$_3$, tetramethylsilane as an internal standard, WALTZ proton noise decoupling technique) 32.2, 30.3, 29.4, 21.7, 11.1, 6.4 ppm.

Example 2

Synthesis of [(S)-2-methylbutyl] phenyldichlorosilane.

Anhydrous tetrahydrofuran (125 mL) was put into a reactor with magnesium (5.7 g, 0.24 mol) and molecular sieves 4A which had been dehydrated and deaerated, followed by charging of argon gas. A small amount of iodine was slowly added to the mixture. (S)-(+)-1-bromo-2-methylbutane (30 g, 0.20 mol) was added dropwise to the slowly stirred mixture so that the reaction mixture was gradually refluxed. After the reaction was complete, the obtained Grignard reagent was transferred to a dropping funnel. The Grignard reagent was added dropwise to a solution being stirred containing phenyltrichlorosilane (50 g, 0.24 mol) in anhydrous tetrahydrofuran (50 mL) in another reactor which had been dehydrated and deaerated, followed by charging of argon gas, at 40° C.–50° C. The reaction mixture was then stirred overnight at room temperature. Hexane (500 mL) was added to the reaction mixture, and the resulting mixture was filtered under pressure, followed by fractional distillation of the filtrate to provide the desired product.

Main fraction:

Boiling point 77° C.–78° C./0.8 mmHg.

Yield 19.8 g (34%).

$^{29}$Si-NMR (CDCl$_3$, tetramethylsilane as an internal standard, gated proton decoupling technique) 18.9 ppm.

$^{13}$C-NMR (CDCl$_3$, tetramethylsilane as an internal standard, WALTZ proton noise decoupling technique) 133.4, 133.3, 131.5, 128.3, 32.3, 30.4, 28.4, 21.8, 11.2 ppm.

Example 3

Syntheses of [(S)-2-methylbutyl]trichlorosilane and bis[(S)-2-methylbutyl]dichlorosilane.

Anhydrous diethyl ether (125 mL) was put into a reactor with magnesium (7.4 g, 0.31 mol) and molecular sieves 4A which had been dehydrated and deaerated, followed by charging of argon gas. A small amount of iodine was slowly added to the mixture. (S)-(+)-1-bromo-2-methylbutane (2.5 g, 0.02 mol) was added dropwise to the slowly stirred mixture. In addition, (S)-(+)-1-chloro-2-methylbutane (27 g, 0.25 mol) was added dropwise to the stirred mixture so that the reaction mixture was gradually refluxed. After the reaction was complete, the obtained Grignard reagent was transferred to a dropping funnel. The Grignard reagent was added dropwise to a solution being stirred containing tetrachlorosilane (15 g, 0.088 mol) in anhydrous diethyl ether (50 mL) in another reactor which had been dehydrated and deaerated, followed by charging of argon gas, at 40° C.–50° C. The reaction mixture was then stirred overnight at room temperature. Hexane (500 mL) was added to the reaction mixture, and the resulting mixture was filtered under pressure, followed by fractional distillation of the filtrate to provide the desired product.

Main fraction:

Boiling point 45° C.–46° C./7 mmHg.

Yield 12.1 g (22%).

$^{29}$Si-NMR (CDCl$_3$, tetramethylsilane as an internal standard, gated proton decoupling technique) 12.6 ppm.

$^{13}$C-NMR (CDCl$_3$, tetramethylsilane as an internal standard, WALTZ proton noise decoupling technique) 32.0, 30.5, 21.5, 11.2 ppm.

The second fraction:

Boiling point 77° C.–78° C./2.5 mmHg.

Yield 6.5 g (20%).

$^{29}$Si-NMR (CDCl$_3$, tetramethylsilane as an internal standard, gated proton decoupling technique) 32.7 ppm.

$^{13}$C-NMR (CDCl$_3$, tetramethylsilane as an internal standard, WALTZ proton noise decoupling technique) 32.3, 30.2, 28.9, 21.8, 11.2 ppm.

According to the above described data of $^{29}$Si-NMR and boiling point, the first fraction (main fraction) and the second fraction were identified with [(S)-2-methylbutyl]trichlorosilane and bis[(S)-2-methylbutyl]dichlorosilane, respectively.

With regard to other fourteen dichlorosilanes containing (S)-2-methylbutyl group which were synthesized according to the same manner as described above, the data of boiling point, chemical shifts of $^{29}$Si-NMR (CDCl$_3$, tetramethylsilane as an internal standard, gated proton decoupling technique) and $^{13}$C-NMR (CDCl$_3$, tetramethylsilane as an internal standard, WALTZ proton noise decoupling technique) are listed on Tables 1 to 3. In the tables, "X 2" and "X 3" used in the data of $^{13}$C-NMR mean two-fold and three-fold in peak intensity, respectively. In the data of $^{13}$C-NMR, "R$^+$" is identified with the carbon peak of 5 kinds of carbons in (S)-2-methylbutyl group.

The yields of these dichlorosilanes are in the range of about 45% and 55%, based on the starting material, i.e., (S)-(+)-1-bromo-2-methylbutane or (S)-(+)-1-chloro-2-methylbutane.

TABLE 1

| R(Chiral) SiCl$_2$ | C2 | n-C3 | n-C4 | n-C5 | n-C6 |
|---|---|---|---|---|---|
| bp (°C./mmHg) | 66–71/12 | 76–77/8 | 69–70/2.5 | 104–106/8 | 79–82/0.85 |
| $^{29}$Si (ppm) | 34.54 | 34.54 | 33.19 | 33.20 | 33.13 |
| $^{13}$C (ppm) | 6.16 | 11.23(R$^+$) | 11.21(R$^+$) | 11.22(R$^+$) | 11.21(R$^+$) |
| | 11.21(R$^+$) | 16.20 | 13.59 | 13.87 | 14.05 |
| | 13.59 | 17.26 | 21.03 | 21.25 | 21.32 |
| | 21.80(R$^+$) | 21.84(R$^+$) | 21.81(R$^+$) | 21.82(R$^+$) | 21.81(R$^+$) |
| | 27.64(R$^+$) | 23.68 | 24.58 | 22.10 | 22.41 |
| | 30.21(R$^+$) | 28.17(R$^+$) | 25.54 | 22.16 | 22.49 |
| | 32.34(R$^+$) | 30.24(R$^+$) | 28.06(R$^+$) | 28.07(R$^+$) | 28.07(R$^+$) |
| | | 32.37(R$^+$) | 30.23(R$^+$) | 30.23(R$^+$) | 30.23(R$^+$) |
| | | | 32.35(R$^+$) | 32.36(R$^+$) | 31.33 |
| | | | | 34.66 | 32.18 |
| | | | | | 32.36(R$^+$) |

TABLE 2

| R(Chiral)SiCl$_2$ | n-C7 | n-C8 | n-C9 | n-C10 | n-C11 |
|---|---|---|---|---|---|
| bp (°C./mmHg) | 101–102/0.9 | 93–94/0.30 | 104–105/0.35 | 119–121/0.40 | 135–136/0.40 |
| $^{29}$Si (ppm) | 33.24 | 33.10 | 33.20 | 33.19 | 33.19 |
| $^{13}$C (ppm) | 11.22(R$^+$) | 11.20(R$^+$) | 11.22(R$^+$) | 11.22(R$^+$) | 11.22(R$^+$) |
|  | 14.08 | 14.09 | 14.11 | 14.12 | 14.13 |
|  | 21.32 | 21.33 | 21.33 | 21.33 | 21.33 |
|  | 21.84(R$^+$) | 21.82(R$^+$) | 21.84(R$^+$) | 21.84(R$^+$) | 21.84(R$^+$) |
|  | 22.45 | 22.45 | 22.45 | 22.45 | 22.45 |
|  | 22.66 | 22.68 | 22.70 | 22.71 | 22.71 |
|  | 28.08(R$^+$) | 28.08(R$^+$) | 28.09(R$^+$) | 28.08(R$^+$) | 28.08(R$^+$) |
|  | 28.81 | 29.12 | 29.15 | 29.15 | 29.15 |
|  | 30.24(R$^+$) | 29.15 | 29.33 | 29.34 | 29.34 |
|  | 31.67 | 30.24(R$^+$) | 29.43 | 29.48 | 29.48 |
|  | 32.36(R$^+$) | 31.89 | 30.24(R$^+$) | 29.63 | 29.64 (X2) |
|  |  | 32.53 | 32.37(R$^+$) | 31.93 | 31.94 |
|  |  |  | 32.52 | 32.37(R$^+$) | 32.37(R$^+$) |
|  |  |  |  | 32.52 | 32.52 |

TABLE 3

| R(Chiral)SiCl$_2$ | n-C12 | PhCH$_2$ | PhCH$_2$CH$_2$ | i-C4 |
|---|---|---|---|---|
| bp (°C./mmHg) | 148–151/0.35 | 83–84/0.40 | 101–102/0.35 | 69–70/2.5 |
| $^{29}$Si (ppm) | 33.18 | 37.61 | 32.50 | 32.16 |
| $^{13}$C (ppm) | 11.23(R$^+$) | 11.33(R$^+$) | 11.38(R$^+$) | 11.21(R$^+$) |
|  | 14.14 | 21.87(R$^+$) | 21.95(R$^+$) | 21.84(R$^+$) |
|  | 21.33 | 27.02(R$^+$) | 23.47 | 24.26 |
|  | 21.84(R$^+$) | 30.28(R$^+$) | 28.24 | 25.59 |
|  | 22.45 | 30.76 | 28.71(R$^+$) | 25.65 |
|  | 22.72 | 32.41(R$^+$) | 30.34(R$^+$) | 28.93(R$^+$) |
|  | 28.08(R$^+$) | 125.86 | 32.47(R$^+$) | 30.28(R$^+$) |
|  | 29.15 | 128.65 (X2) | 126.30 | 31.27 |
|  | 29.39 | 129.12 (X2) | 128.05 (X2) | 32.38(R$^+$) |
|  | 29.48 | 134.48 | 128.69 (X2) |  |
|  | 29.67 (X3) |  | 142.84 |  |
|  | 30.24(R$^+$) |  |  |  |
|  | 31.95 |  |  |  |
|  | 32.37(R$^+$) |  |  |  |
|  | 32.52 |  |  |  |

Examples 4 to 6 described below show synthesis examples of optically active chain-like organopolysilanes, using alkyl[(S)-2-methylbutyl]dichlorosilanes. The present invention reveals that the fine molecular structures, material characteristics, and optical properties are varied greatly by virtue of the alkyl structure.

Example 4

Synthesis of poly[methyl-(S)-2-methylbutylsilane]

Sodium metal (30% dispersion, in toluene, 1.9 g), 18-crown-6 (0.05 g), and anhydrous diethyl ether (50 mL) were put into a flask which had been dehydrated and deaerated, followed by charging of argon gas. Methyl[(S)-2-methylbutyl]dichlorosilane (2.05 g, 0.011 mol) was added to the mixture at the oil bath temperature of 40° C., and stirred for 12 hours. The reaction mixture was filtered under pressure, and ethyl alcohol was added to the filtrate. The generated white viscous precipitate was recovered using a centrifuge and then dried in vacuo at 60° C. Yield was 0.45 g. A gel-permeation chromatograph (hereafter, referred to as GPC) on the basis of mono disperse polystyrene standards showed that the polymer possessed a monomodal molecular weight distribution, 51000 of weight-average molecular weight and 3.1 of polydispersity (=weight-average degree of polymer/number-average degree of polymer).

Figure 1:
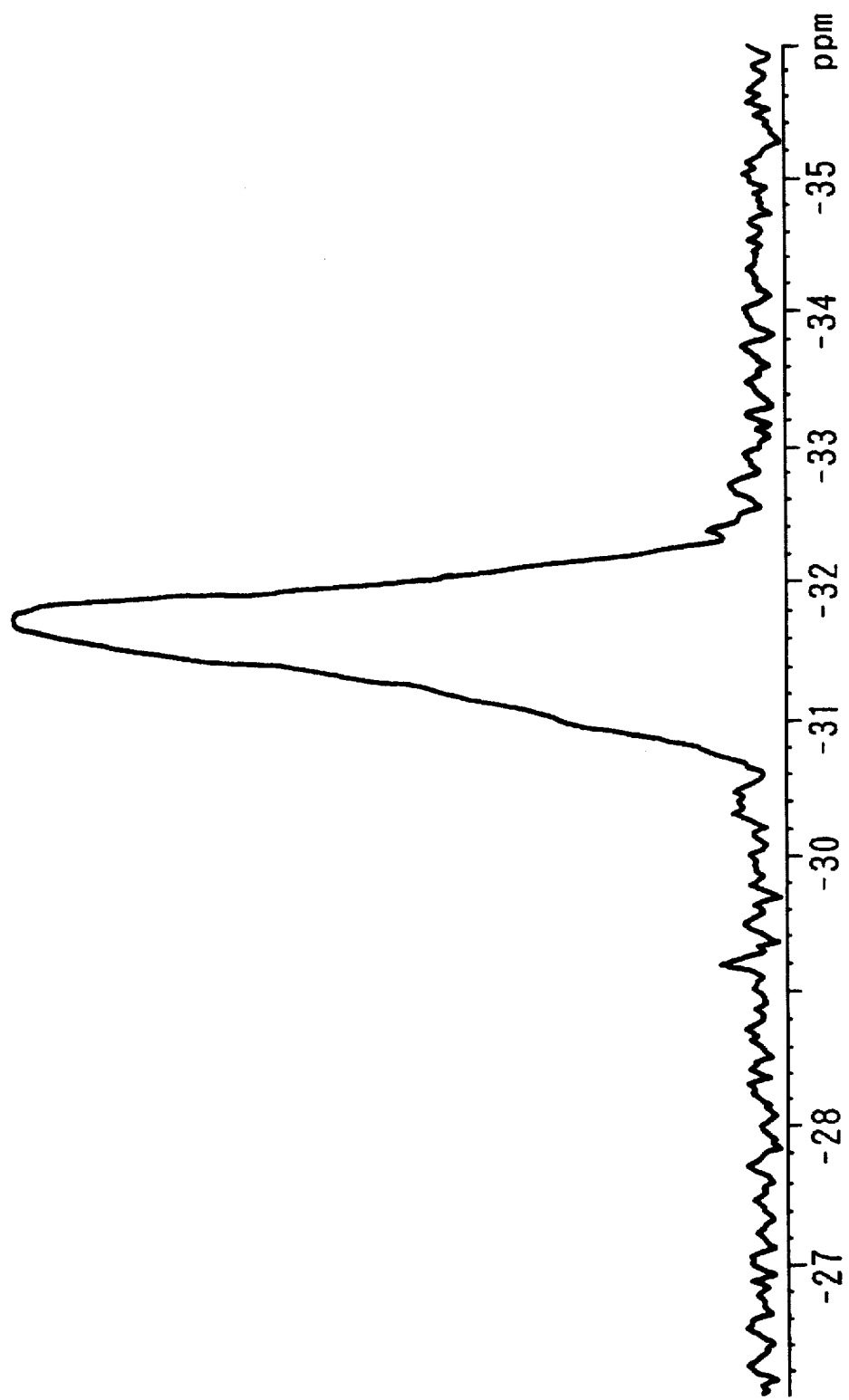
FIG. 1 is a drawing showing a spectrum of $^{29}$Si-NMR (CDCl$_3$, tetramethylsilane as an internal standard, gated proton decoupling technique) of poly[methyl-(S)-2-methylbutylsilane] (51000 of weight-average molecular weight and 3.1 of polydispersity) obtained in Example 4.

The $^{29}$Si-NMR spectrum (CDCl$_3$, tetramethylsilane as an internal standard, gated proton decoupling technique) of the obtained chain-like organopolysilane is shown in FIG. 1. One broad peak appeared at around 31.5 ppm.

As a result of an improved resolution of the peak by virtue of a mathematical treatment, it was found that the peak included at least 7 peaks which were overlapped.

Figure 2:
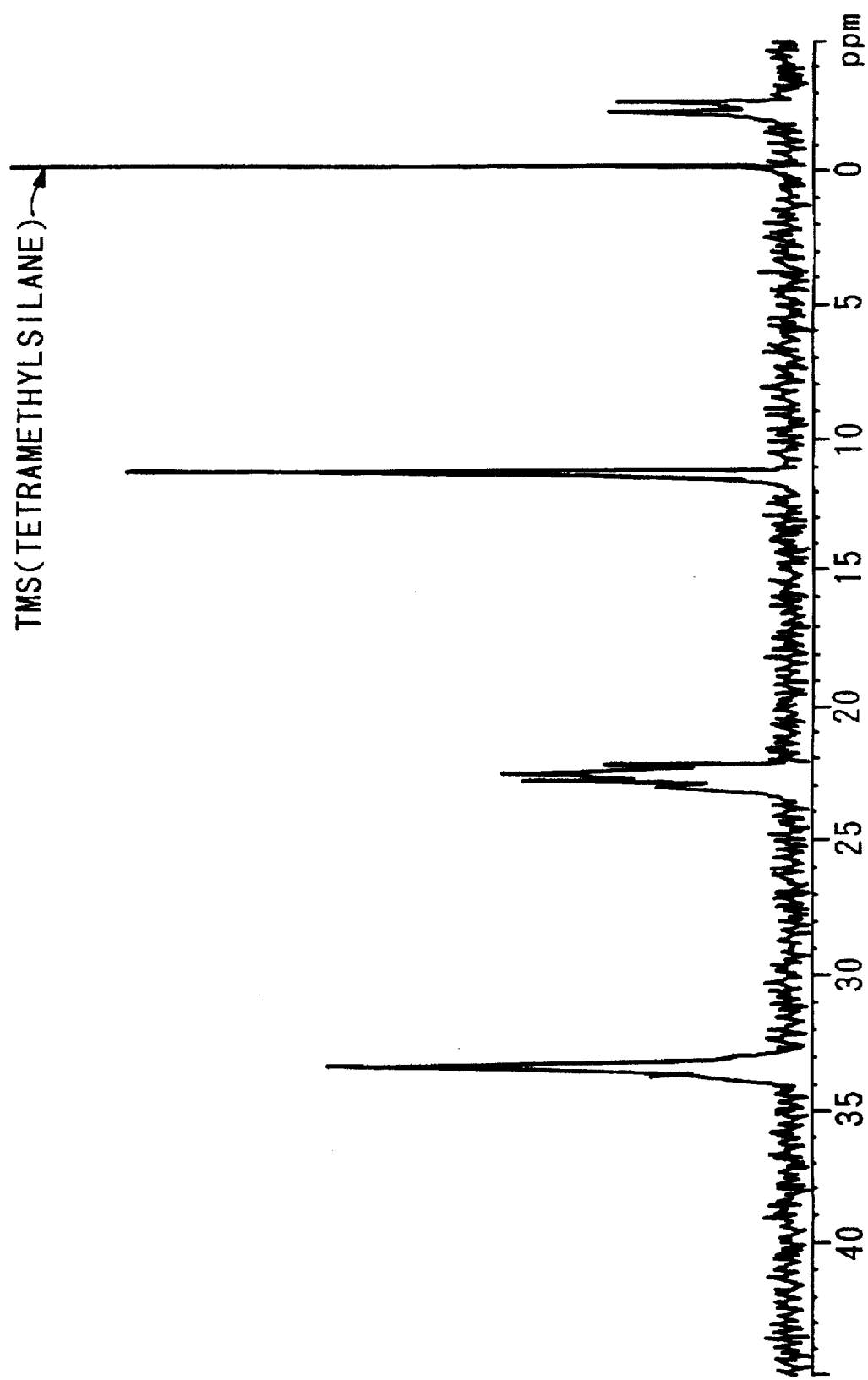
FIG. 2 is a drawing showing a spectrum of $^{13}$C-NMR (CDCl$_3$, tetramethylsilane as an internal standard, proton noise decoupling technique) of poly[methyl-(S)-2-methylbutylsilane] (51000 of weight-average molecular weight and 3.1 of polydispersity) obtained in Example 4.

The $^{13}$C-NMR spectrum (CDCl$_3$, tetramethylsilane as an internal standard, proton noise decoupling technique) of the obtained chain-like organopolysilane is shown in FIG. 2. Broad peaks appeared at around 34, 23, 11, and −2 ppm.

Figure 3:
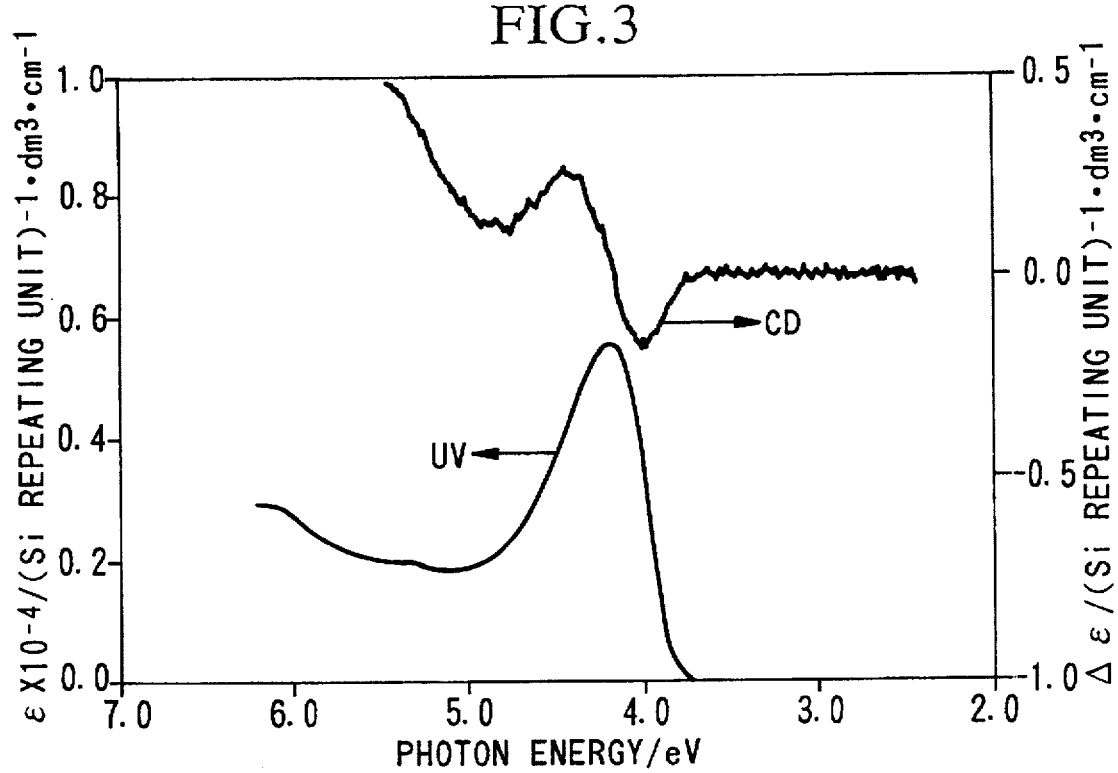
FIG. 3 is a drawing showing both an ultraviolet absorption spectrum and a circular dichroism spectrum (each in i-octane, 20° C.) of poly[methyl-(S)-2-methylbutylsilane] (51000 of weight-average molecular weight and 3.1 of polydispersity) obtained in Example 4.
Figure 4:
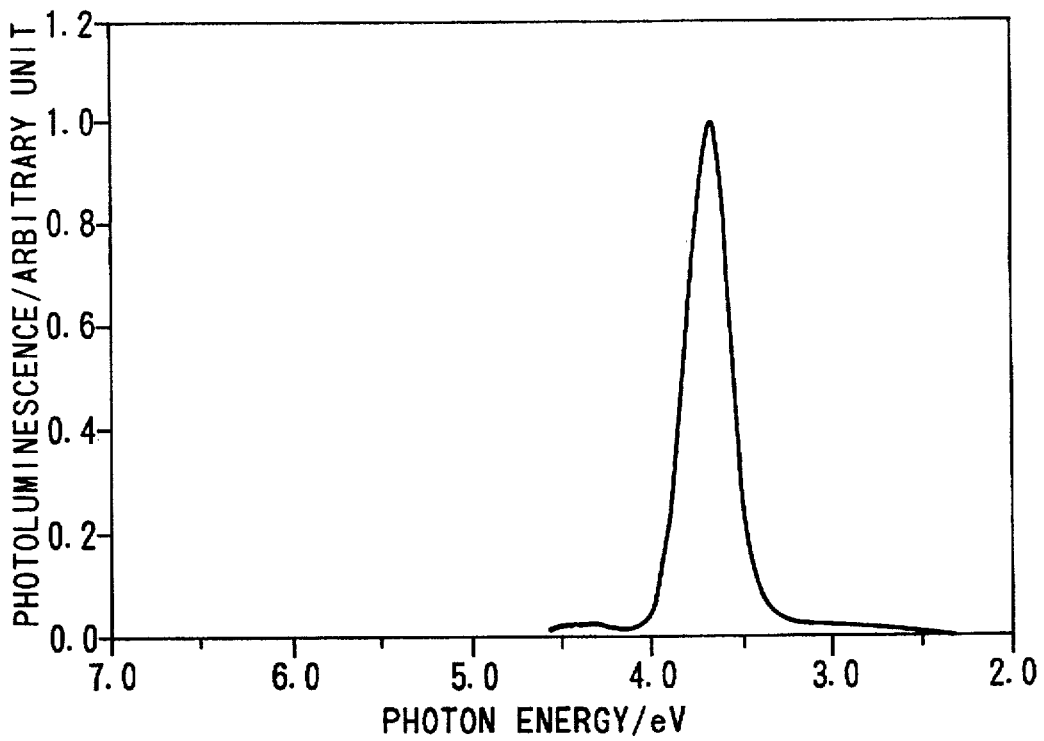
FIG. 4 is a drawing showing a photoluminescence spectrum (in i-octane, 20° C.) of poly[methyl-(S)-2-methylbutylsilane] (51000 of weight-average molecular weight and 3.1 of polydispersity) obtained in Example 4.

The ultraviolet absorption spectrum and the circular dichroism spectrum (each in i-octane, 20° C.) are shown in FIG. 3, and the photoluminescence spectrum of the same (in i-octane, 20° C.) is shown in FIG. 4.

From these three spectra, it was revealed that the lowest excited state of the main-chain at approximately 4.2 eV in the obtained chain-like organopolysilane was composed of a positive Cotton signal at approximately 4.0 eV and a negative Cotton signal at approximately 4.5 eV. In addition, the photoluminescence spectrum appears to display a mirror image relationship with the negative Cotton peak of the circular dichroism spectrum rather than the ultraviolet absorption spectrum and the circular dichroism spectrum. For comparison, in a poly(methylpropylsilane) homopolymer, such a Cotton signal was not observed.

From the results described above, with regard to the obtained optically active chain-like organopolysilane, the following hypothesis can be offered: In a main-chain of the polysilane, both a right handed helical structure and a left handed helical structure, which are different from each other with respect to an excitation energy, exist; the ratio of the right handed helical structure to the left handed helical structure is nearly 1; and silicon bonding electrons are not dispersed over the whole polymer chains but instead are localized at a right-handed helical segment and a left-handed helical segment, which are different from each other with respect to an energy eigenvalue.

Example 5

Synthesis of poly[n-butyl-(S)-2-methylbutylsilane]

Sodium metal (30% dispersion, in toluene, 3.8 g), 15-crown-5 (0.05 g), and anhydrous toluene (50 mL) were put into a flask which had been dehydrated and deaerated, followed by charging of argon gas. n-Butyl[(S)-2-methylbutyl]dichlorosilane (5.0 g, 0.022 mol) was added to the mixture at the oil bath temperature of 120° C., and stirred for 8 hours. The reaction mixture was filtered under pressure, and ethyl alcohol was added to the filtrate. The generated white precipitate was recovered using a centrifuge and then dried in vacuo at 60° C. Yield was 0.27 g, and 7.9% based on n-butyl[(S)-2-methylbutyl]dichlorosilane. The GPC spectrum showed that the polymer was a mono-dispersing type of polymer possessing 3140 of weight average molecular weight and 1.14 of polydispersity.

Figure 5:
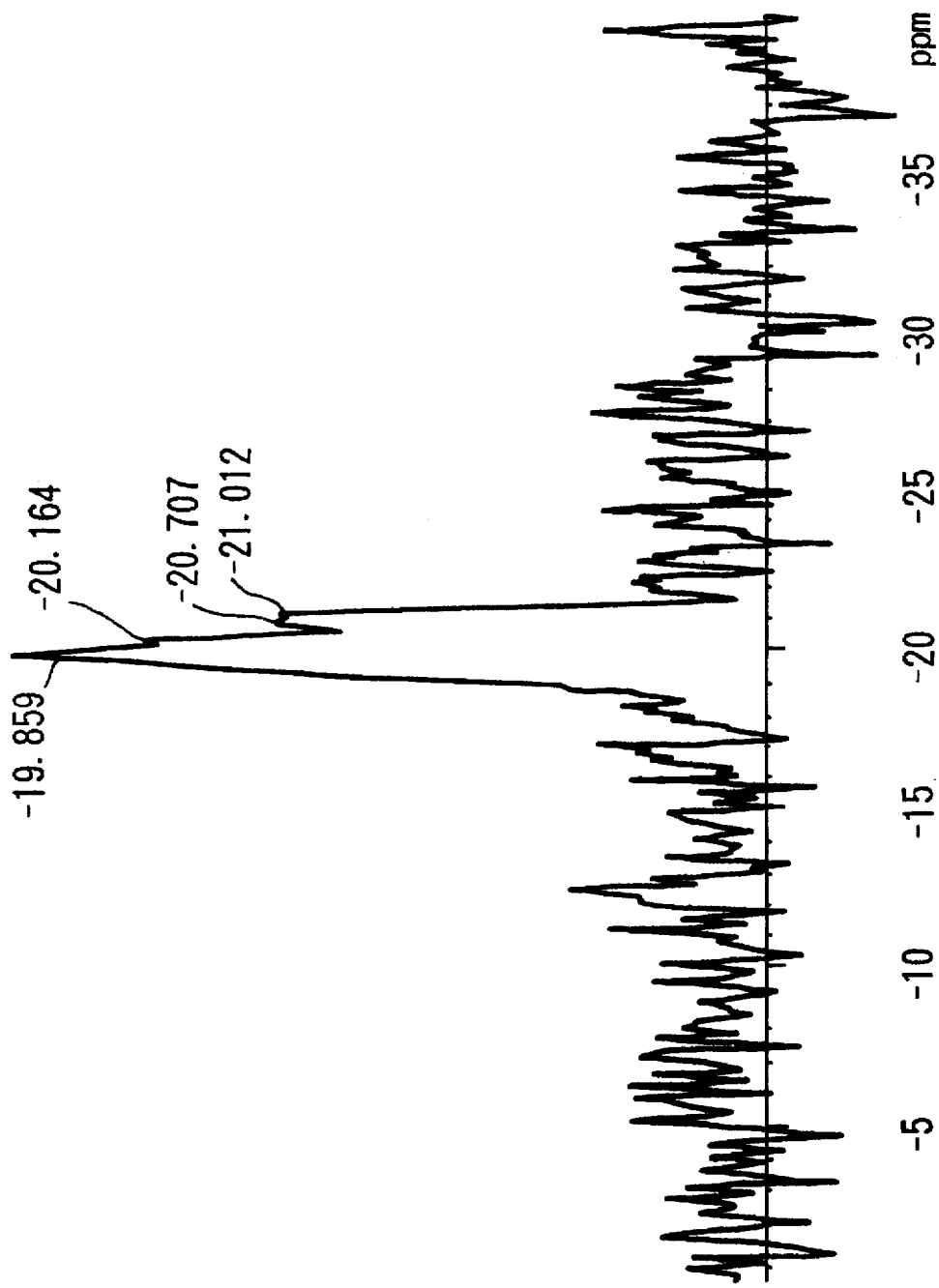
FIG. 5 is a drawing showing a spectrum of $^{29}$Si-NMR (C$_6$D$_5$CD$_3$, tetramethylsilane as an internal standard, gated proton decoupling technique) of poly[n-butyl-(S)-2-methylbutylsilane] (3140 of weight-average molecular weight and 1.14 of polydispersity) obtained in Example 5.

The $^{29}$Si-NMR spectrum (C$_6$D$_5$CD$_3$, tetramethylsilane as an internal standard, gated proton decoupling technique, measuring temperature: 60° C.) of the obtained chain organopolysilane is shown in FIG. 5. Almost one broad peak based on the main-chain appeared at around −20.0 ppm.

Figure 6:
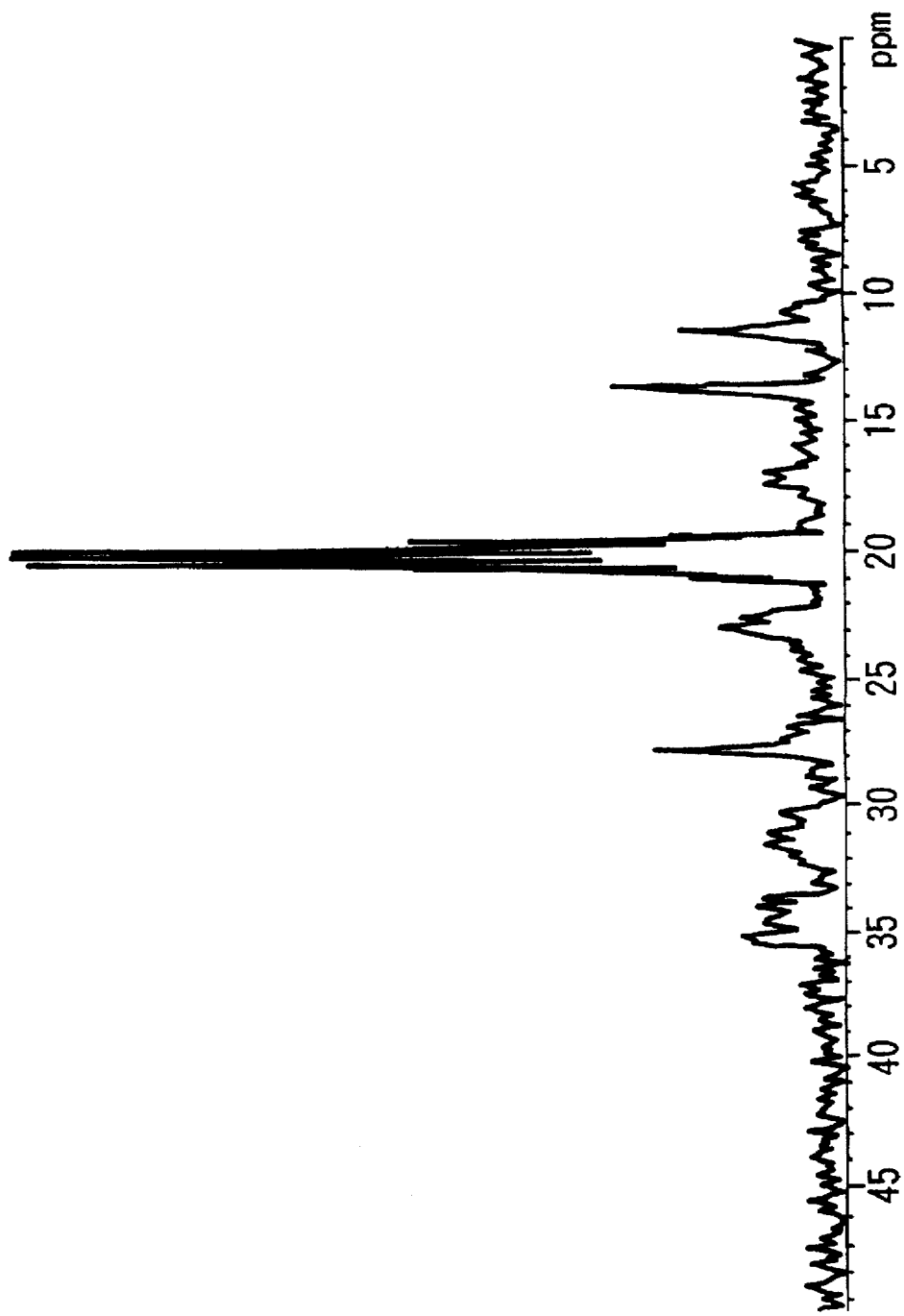
FIG. 6 is a drawing showing a spectrum of $^{13}$C-NMR (C$_6$D$_5$CD$_3$, tetramethylsilane as an internal standard, proton noise decoupling technique) of poly[n-butyl-(S)-2-methylbutylsilane] (3140 of weight-average molecular weight and 1.14 of polydispersity) obtained in Example 5.

The $^{13}$C-NMR spectrum (C$_6$D$_5$CD$_3$, tetramethylsilane as an internal standard, proton noise decoupling technique, measuring temperature: 60° C.) of the obtained chain organopolysilane is shown in FIG. 6. Several peaks appeared at around 35, 31, 28, 23, 17, 14, and 12 ppm (with the proviso that the seven peaks at around 20 ppm were assigned to the deuterized methyl group of C$_6$D$_5$CD$_3$).

Figure 7:
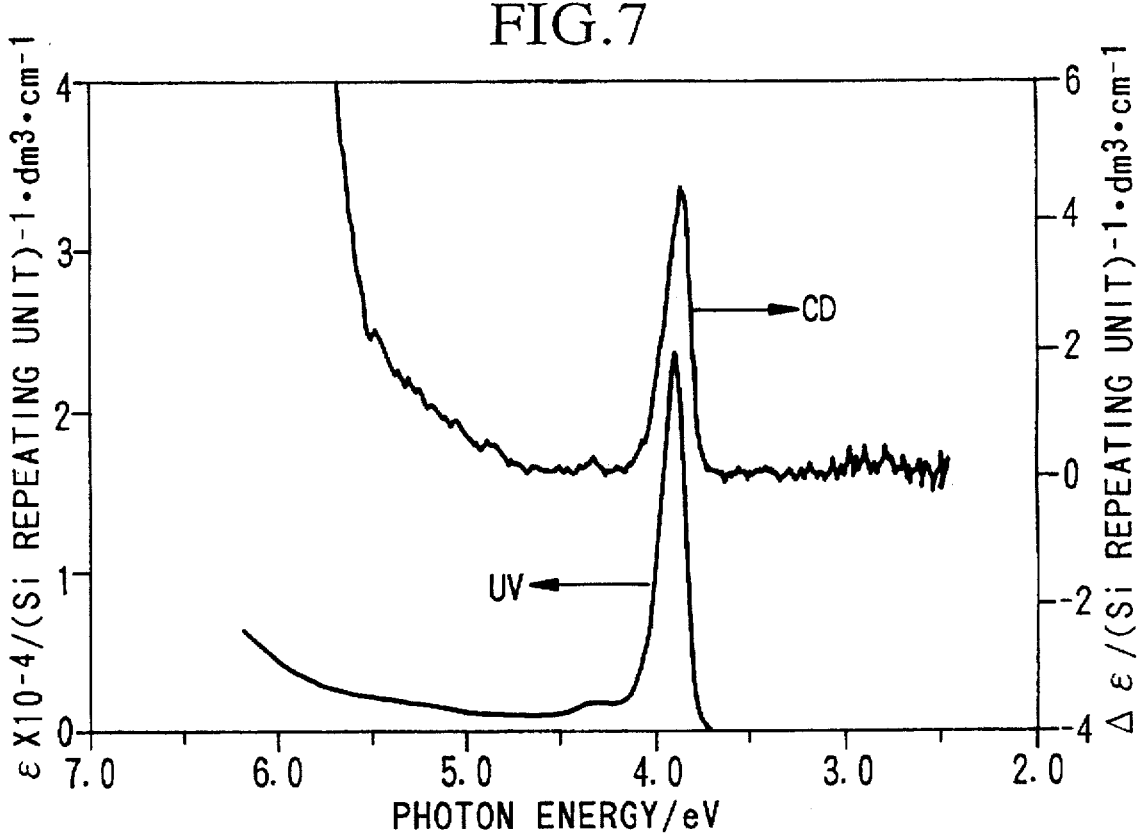
FIG. 7 is a drawing showing both an ultraviolet absorption spectrum and a circular dichroism spectrum (each in i-octane, 20° C.) of poly[n-butyl-(S)-2-methylbutylsilane] (3140 of weight-average molecular weight and 1.14 of polydispersity) obtained in Example 5.
Figure 8:
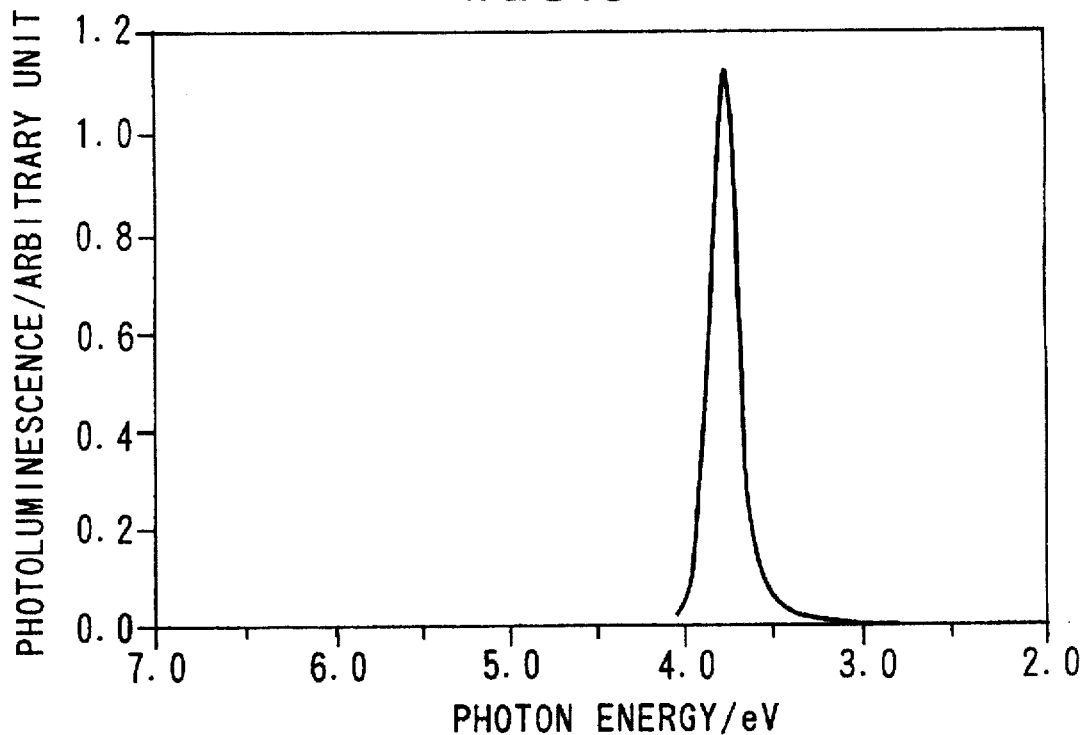
FIG. 8 is a drawing showing a photoluminescence spectrum (in i-octane, 20° C.) of poly[n-butyl-(S)-2-methylbutylsilane] (3140 of weight-average molecular weight and 1.14 of polydispersity) obtained in Example 5.
Figure 9:
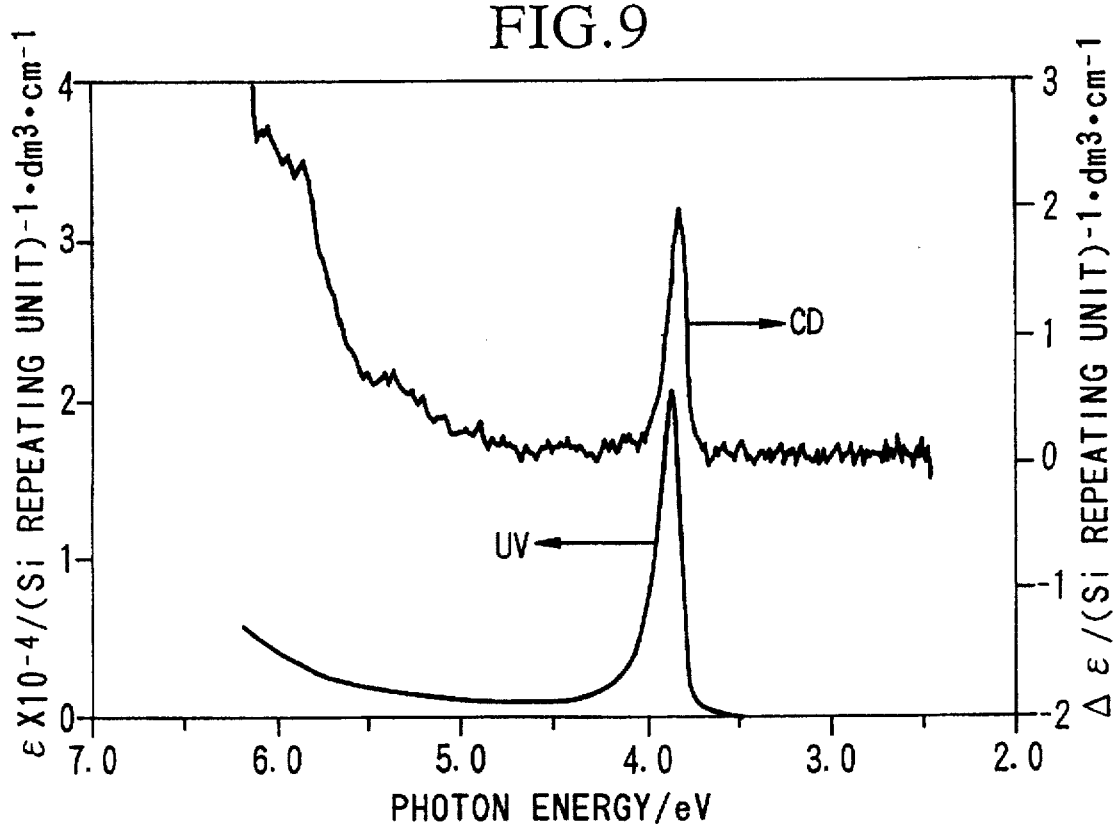
FIG. 9 is a drawing showing both an ultraviolet absorption spectrum and a circular dichroism spectrum (each in i-octane, 20° C.) of poly[ethyl-(S)-2-methylbutylsilane] (8240 of weight-average molecular weight and 1.40 of polydispersity) synthesized according to the process described in Example 5.
Figure 10:
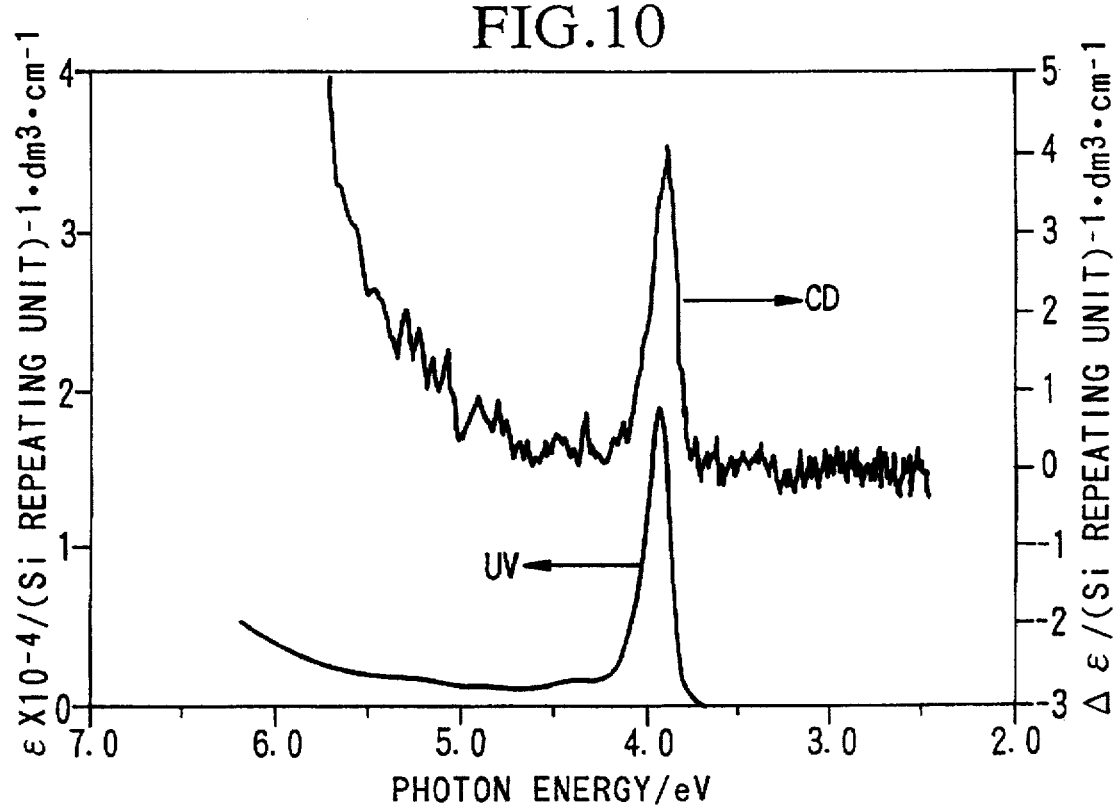
FIG. 10 is a drawing showing both an ultraviolet absorption spectrum and a circular dichroism spectrum (each in i-octane, 20° C.) of poly[n-propyl-(S)-2-methylbutylsilane] (2950 of weight-average molecular weight and 1.11 of polydispersity) synthesized according to the process described in Example 5.
Figure 11:
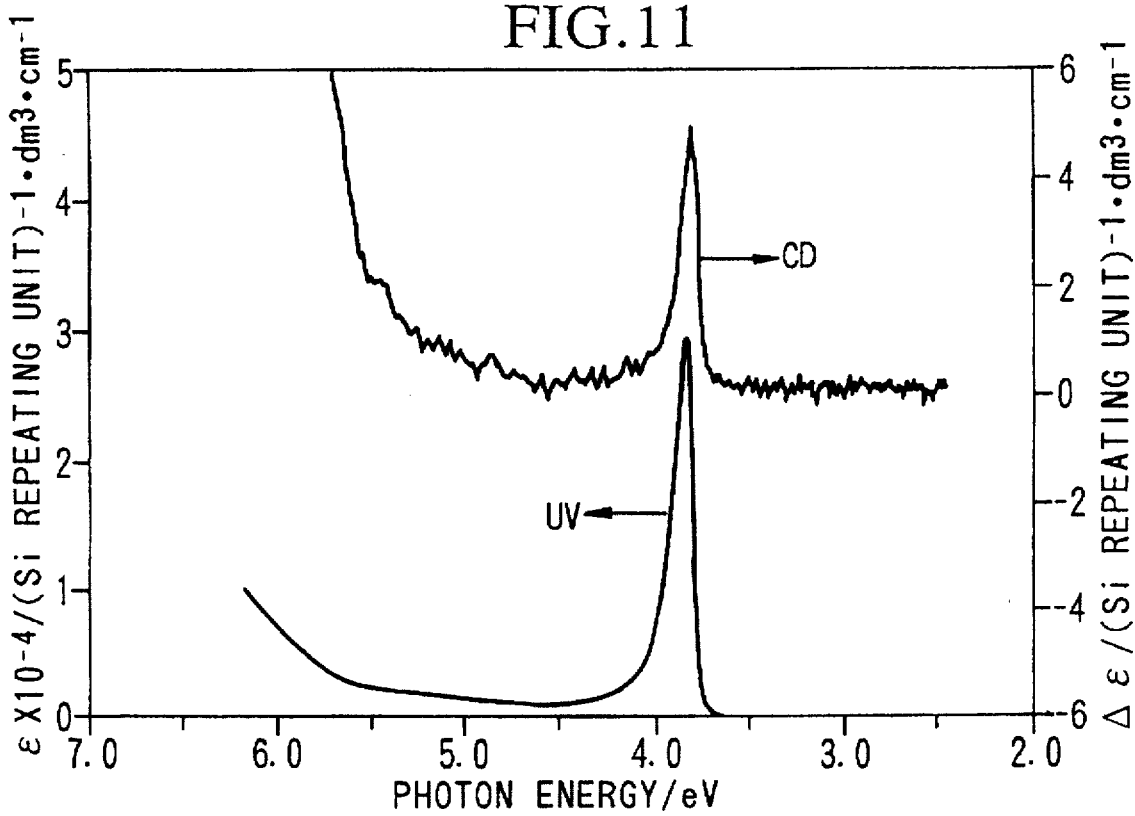
FIG. 11 is a drawing showing both an ultraviolet absorption spectrum and a circular dichroism spectrum (each in i-octane, 20° C.) of poly[n-pentyl-(S)-2-methylbutylsilane] (5960 of weight-average molecular weight and 1.19 of polydispersity) synthesized according to the process described in Example 5.
Figure 12:
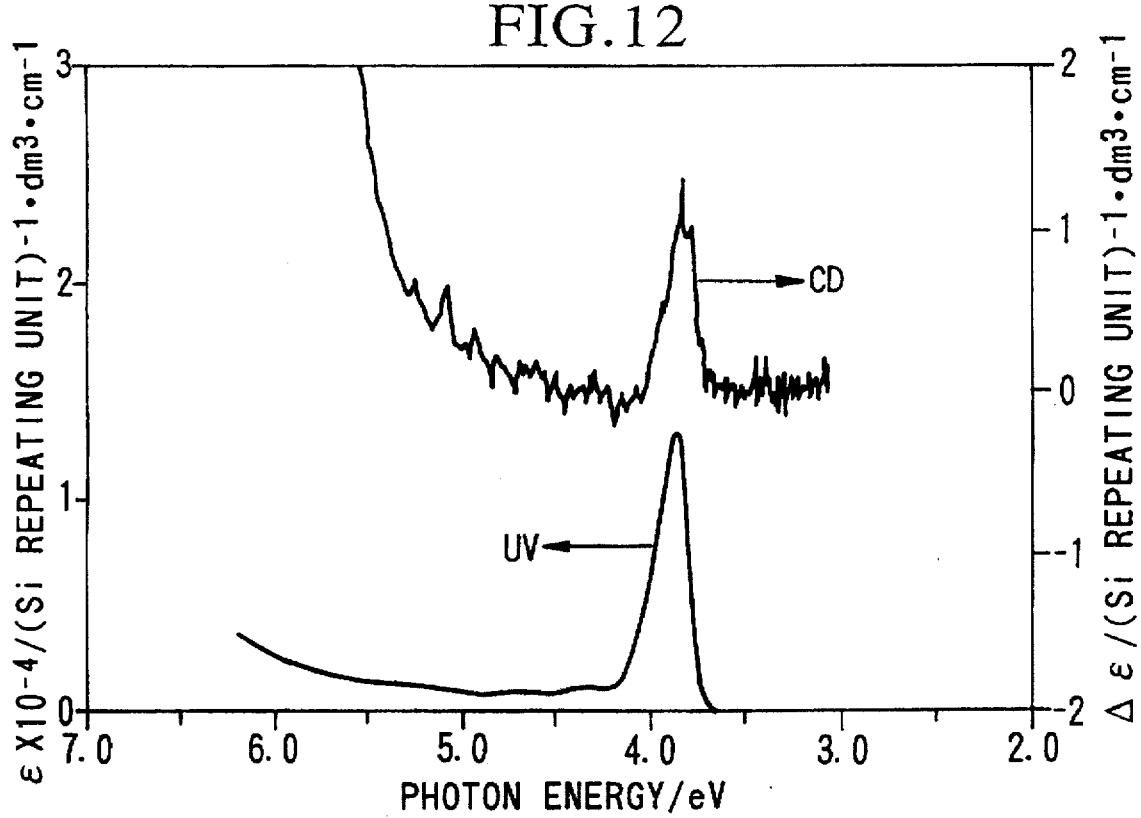
FIG. 12 is a drawing showing both an ultraviolet absorption spectrum and a circular dichroism spectrum (each in i-octane, 20° C.) of poly[i-butyl-(S)-2-methylbutylsilane] (2 140 of weight-average molecular weight and 1.11 of polydispersity) synthesized according to the process described in Example 5.
Figure 13:
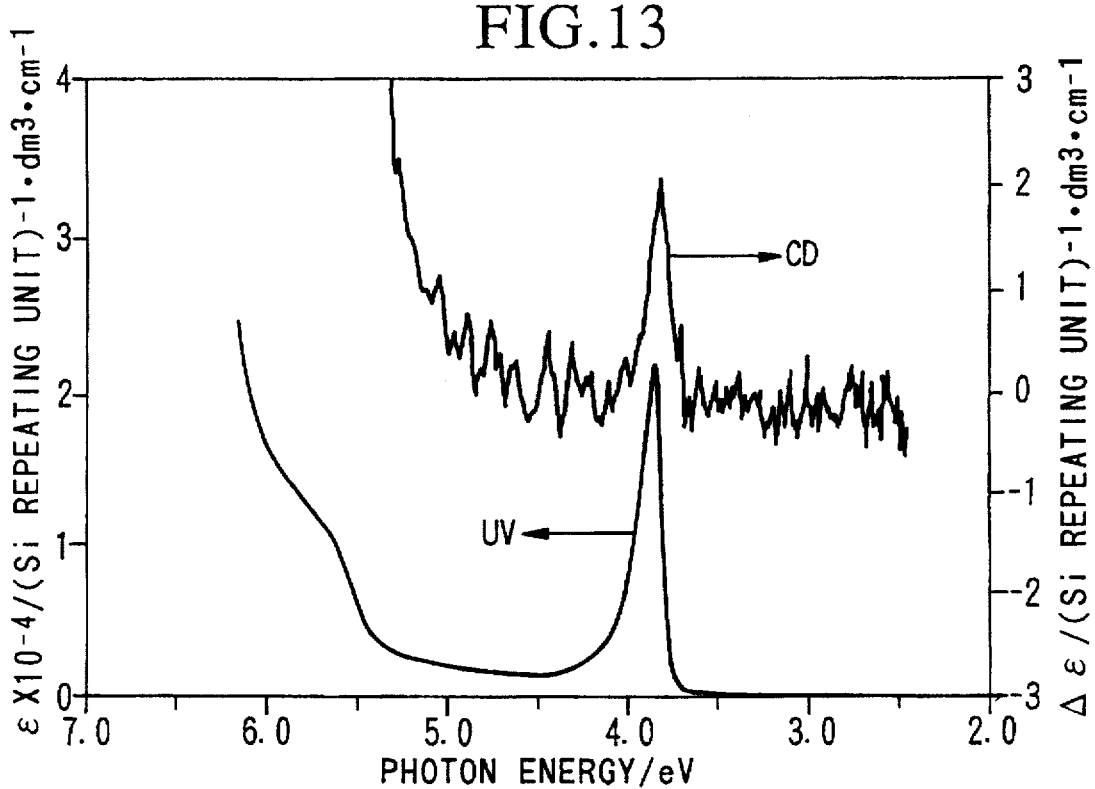
FIG. 13 is a drawing showing both an ultraviolet absorption spectrum and a circular dichroism spectrum (each in i-octane, 20° C.) of poly[β-phenethyl-(S)-2-methylbutylsilane] (5810 of weight-average molecular weight and 1.27 of polydispersity) synthesized according to the process described in Example 5.
Figure 14:
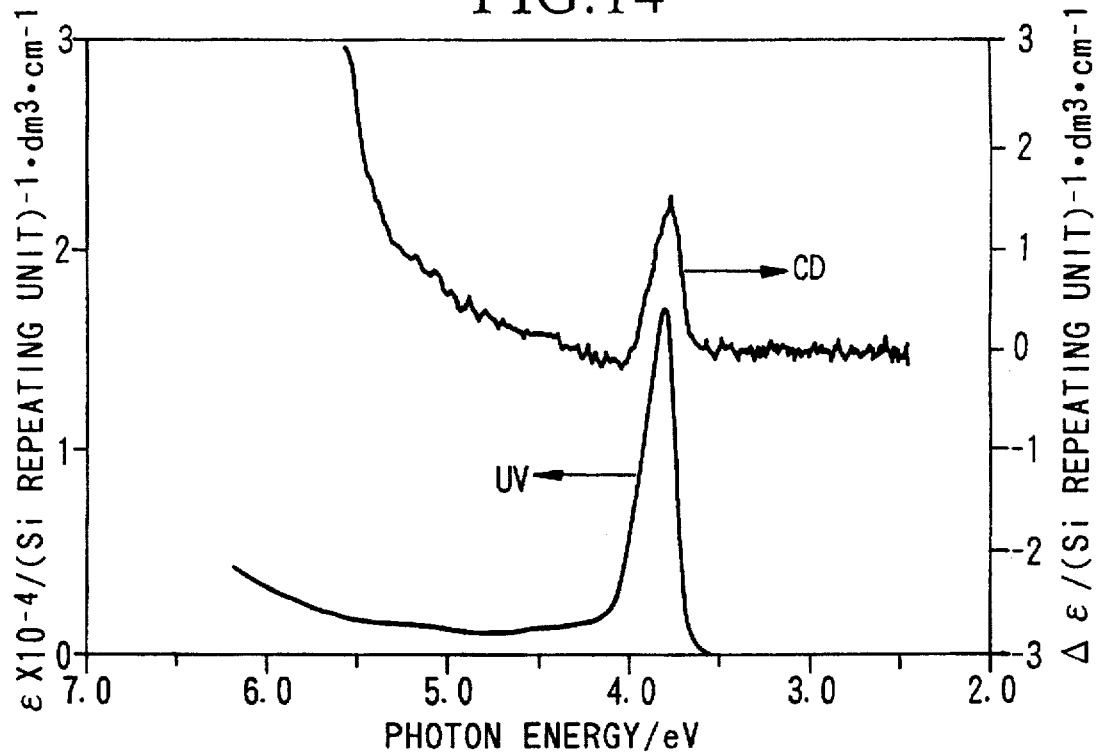
FIG. 14 is a drawing showing both an ultraviolet absorption spectrum and a circular dichroism spectrum (each in i-octane, 20° C.) of poly[bis{(S)-2-methylbutyl}silane] (2680 of weight-average molecular weight and 1.13 of polydispersity) synthesized according to the process described in Example 5.

The ultraviolet absorption spectrum and the circular dichroism spectrum (each in i-octane, 20° C.) are shown in FIG. 7, and the photoluminescence spectrum of the same (in i-octane, 20° C.) is shown in FIG. 8.

From these three spectra, it was revealed that the Cotton band at 3.93 eV possessed an essentially identical curve as the backbone absorption at 3.93 eV and the absorption maximum identified with that of the backbone absorption, and that the configuration of the photoluminescence spectrum at 3.82 eV displayed a mirror image relationship with the backbone absorption or Cotton absorption at 3.93 eV. For this reason, it was found that an optically active organopolysilane main-chain itself possessed only a right-handed helical structure with a constant pitch.

The backbone absorption of the obtained poly[n-butyl-(S)-2-methylbutylsilane] possessed the optical characteristics such that the absorption intensity and full width at half maximum were, respectively, approximately three times and one-third, compared with that of the well-known optically inactive organopolysilane such as poly[methyl-n-propylsilane], as well as the characteristics that the molecular weight distribution was extremely narrow and substantially a mono-dispersion. Furthermore, it was apparent that the obtained polysilane possessing a one-handed helical structure could be extremely stable in a solution at around room temperature, since the backbone absorption intensity and the Cotton band intensity at −10° C. are approximately 110% based on those at 80° C., in i-octane.

The properties of poly[n-butyl-(S)-2-methylbutylsilane] (the mono disperse of the molecular weight, the increase of intensity and narrowness of width of the backbone absorption, the mirror image property of the absorption spectrum and photoluminescence spectrum, and the identification between the absorption spectrum and the circular dichroism spectrum) were obtained in the case where the n-butyl group of poly[n-butyl-(S)-2-methylbutylsilane] was replaced with ethyl group, n-propyl group, i-butyl group, n-pentyl group, (S)-2-methylbutyl group, or a β-phenethyl group.

The ultraviolet absorption spectra and the circular dichroism spectra (each in i-octane, 20° C.) of poly[ethyl-(S)-2-methylbutylsilane], poly[n-propyl-(S)-2-methylbutylsilane], poly[i-butyl-(S)-2-methylbutylsilane], poly[n-pentyl-(S)-2-methylbutylsilane], poly[bis{(S)-2-methylbutyl}silane], and poly[β-phenethyl-(S)-2-methylbutylsilane], which are synthesized under the same polymerization condition as described in Example 5, are shown in FIG. 9 through FIG. 14, respectively.

Example 6

Synthesis of poly[n-hexyl-(S)-2-methylbutylsilane]

Sodium metal (30% dispersion, in toluene, 3.8 g), 15-crown-5 (0.05 g), and anhydrous toluene (50 mL) were put into a flask which had been dehydrated and deaerated, followed by charging of argon gas. n-hexyl[(S)-2-ethylbutyl]dichlorosilane (5.2 g) was added to the mixture at the oil bath temperature of 120° C., and stirred for 3 hours. The reaction mixture was filtered under pressure, and ethyl alcohol was added to the filtrate. The generated white precipitates (the first fraction and the second fraction) were recovered using a centrifuge and then dried in vacuo at 60° C. Yields of the first fraction and the second fraction were 0.19 g (5.1%) and 0.44 g (12.0%), respectively. The GPC showed that the polymer possessed a bimodal molecular weight distribution, 5160 of weight average molecular weight and 1.38 of polydispersity with regard to the first fraction, and 19200 of weight average molecular weight and 1.66 of polydispersity with regard to the second fraction.

Figure 15:
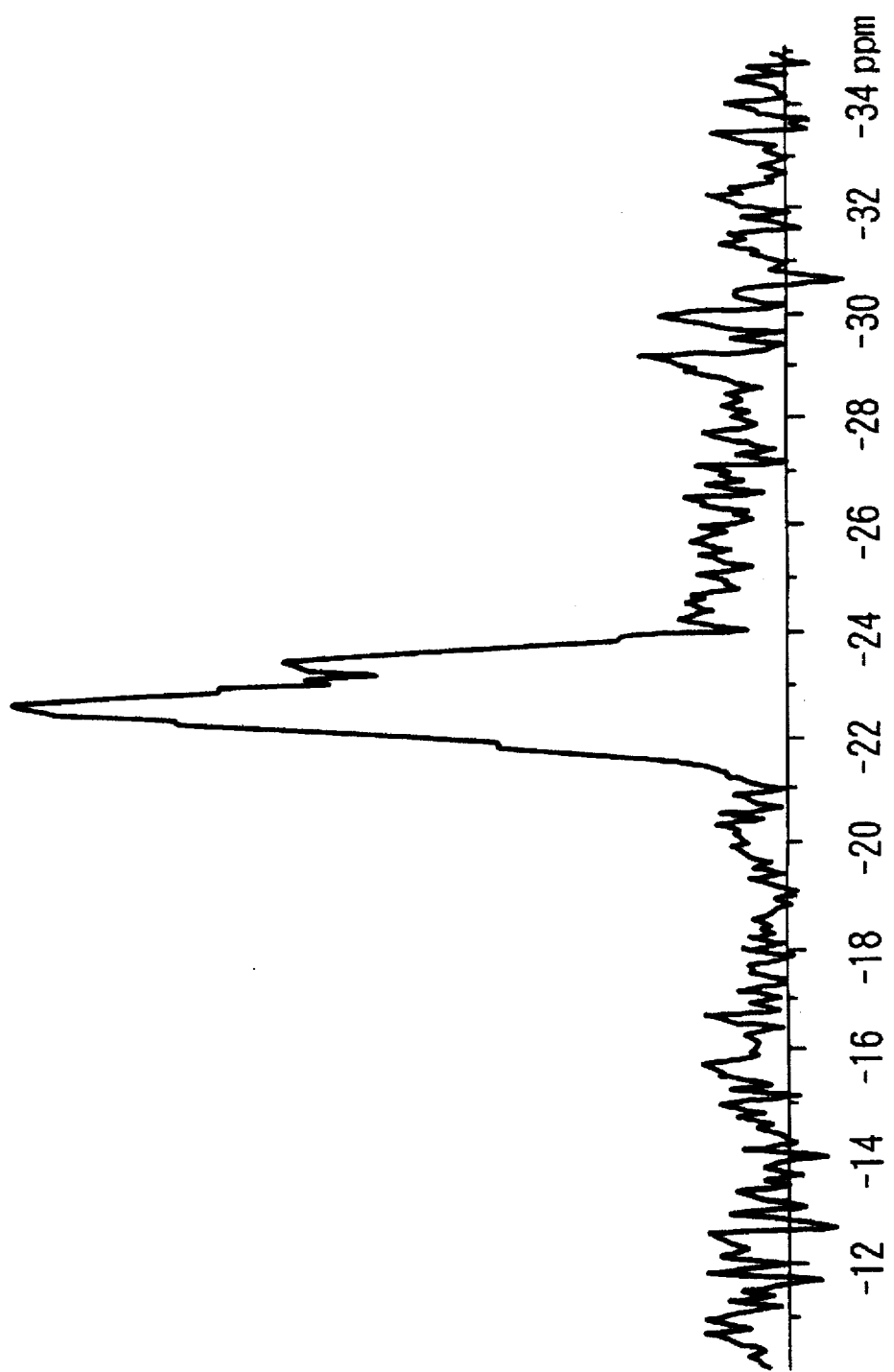
FIG. 15 is a drawing showing a spectrum of $^{29}$Si-NMR (CDCl$_3$, tetramethylsilane as an internal standard, gated proton decoupling technique) of the first fraction of poly[n-hexyl-(S)-2-methylbutylsilane] (5160 of weight-average molecular weight and 1.38 of polydispersity) obtained in Example 6.

The $^{29}$Si-NMR spectrum (CDCl$_3$, tetramethylsilane as an internal standard, gated proton decoupling technique, measuring temperature: 60° C.) of the obtained rust fraction, poly[n-hexyl-(S)-2-ethylbutylsilane], is shown in FIG. 15. One broad peak based on the main-chain appeared at the range of around −22 ppm and −23 ppm.

Figure 16:
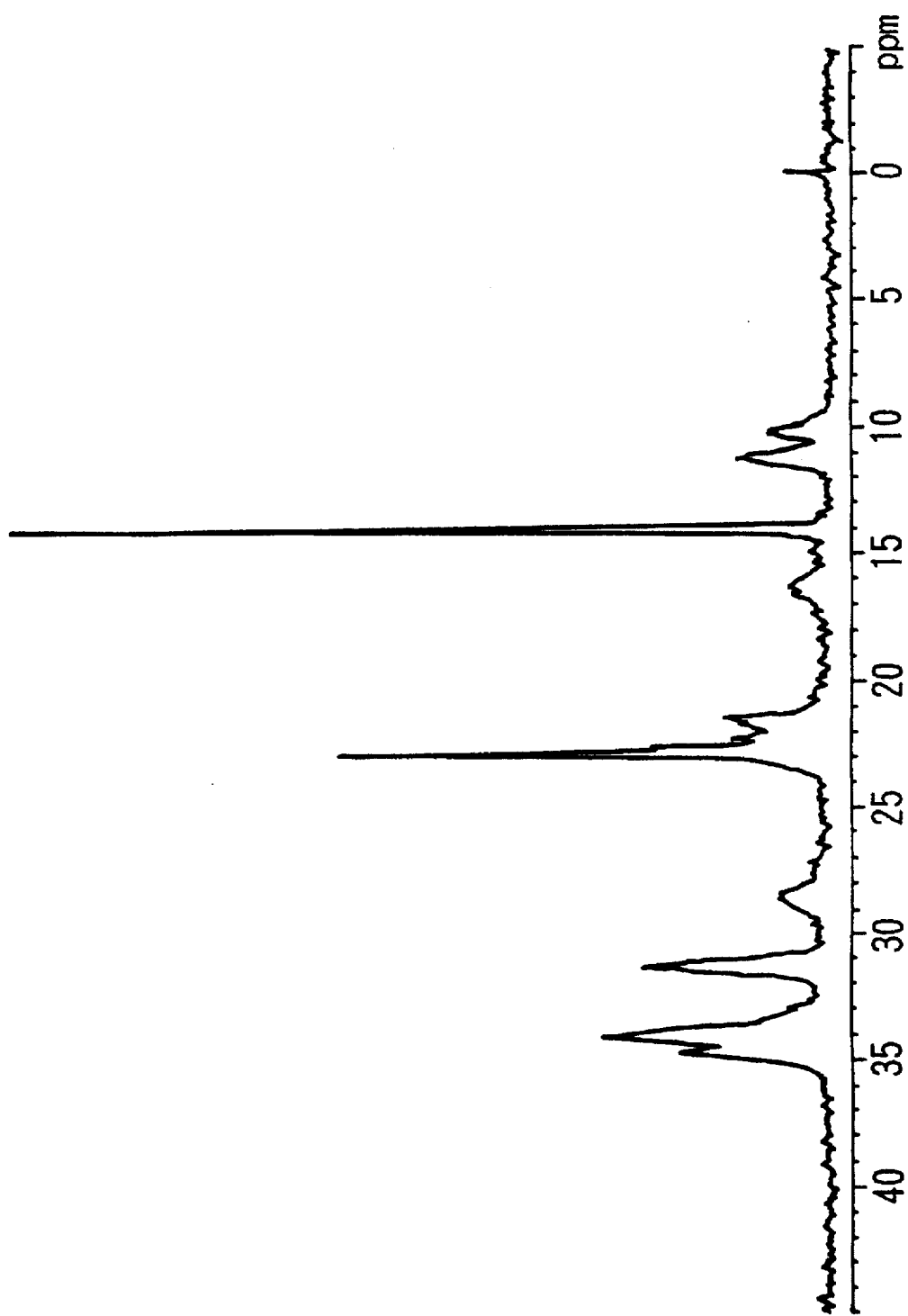
FIG. 16 is a drawing showing a spectrum of $^{13}$C-NMR (CDCl$_3$, tetramethylsilane as an internal standard, proton noise decoupling technique) of the first fraction of poly[n-hexyl-(S)-2-methylbutylsilane] (5160 of weight-average molecular weight and 1.38 of polydispersity) obtained in Example 6.

The $^{13}$C-NMR spectrum (CDCl$_3$, tetramethylsilane as an internal standard, proton noise decoupling technique) of the obtained first fraction, poly[n-hexyl-(S)-2-ethylbutylsilane], is shown in FIG. 16. Some peaks appeared at around 35, 34, 32, 29, 23, 22, 16, 14, 11, and 10 ppm.

Figure 17:
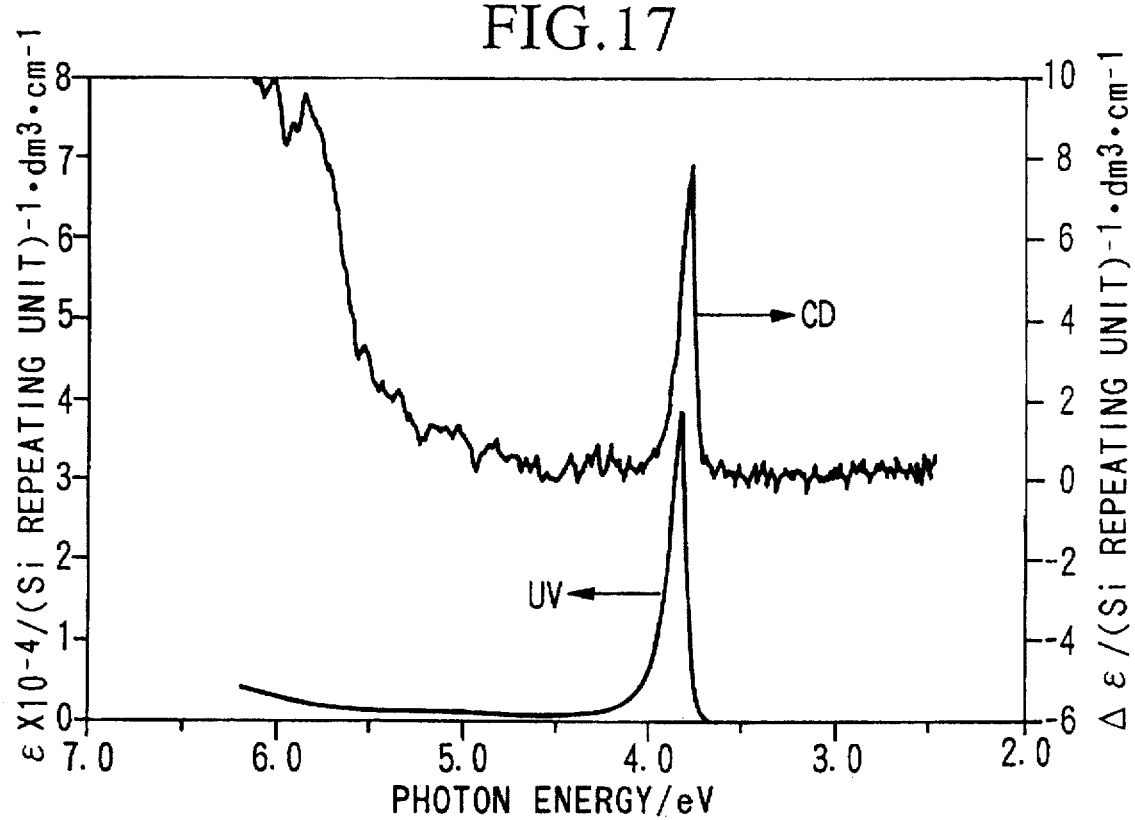
FIG. 17 is a drawing showing both an ultraviolet absorption spectrum and a circular dichroism spectrum (each in i-octane, 20° C.) of the first fraction of poly[n-hexyl-(S)-2-methylbutylsilane] (5160 of weight-average molecular weight and 1.38 of polydispersity) obtained in Example 6.
Figure 18:
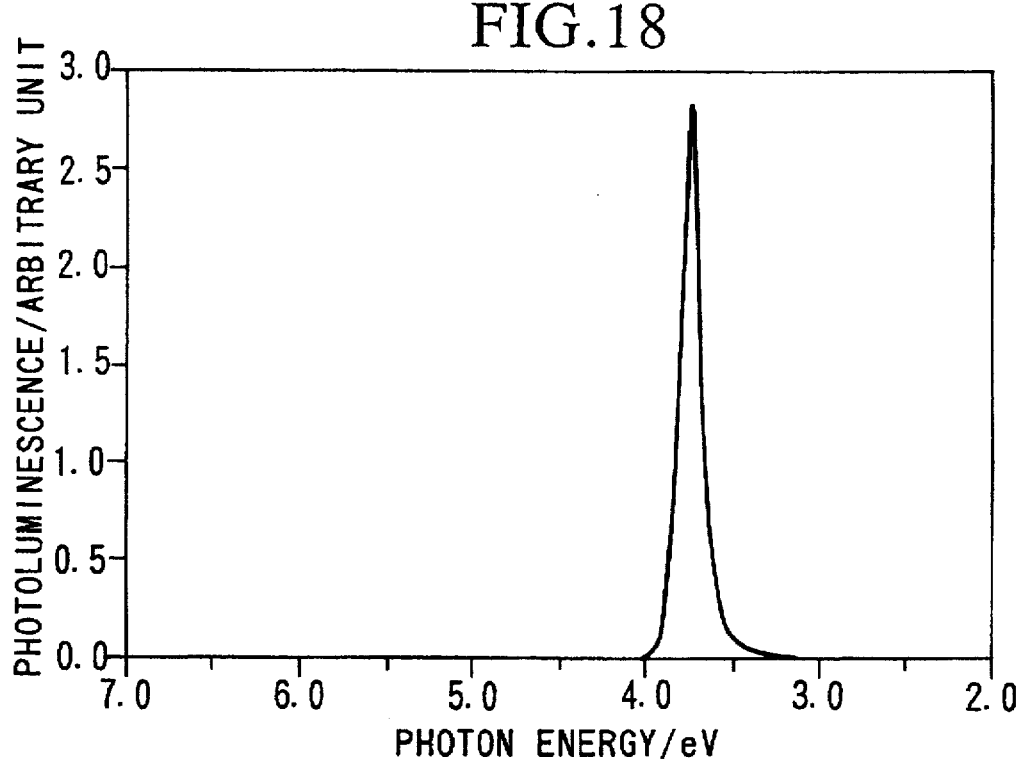
FIG. 18 is a drawing showing a photoluminescence spectrum (in i-octane, 20° C.) of the first fraction of poly[n-hexyl-(S)-2-methylbutylsilane] (5160 of weight-average molecular weight and 1.38 of polydispersity) obtained in Example 6.

The ultraviolet absorption spectrum and the circular dichroism spectrum of the obtained optically active chain-like organopolysilane (each in i-octane, 20° C.) are shown in FIG. 17, and the photoluminescence spectrum of the same (in i-octane, 20° C.) is shown in FIG. 18.

From these three spectra, it was revealed that the Cotton band at 3.83 eV possessed approximately a similar figure as the backbone absorption at 3.85 eV and the absorption maximum photon energy value identified with that of the backbone absorption, and that the profile of the photoluminescence spectrum at 3.78 eV displayed a mirror image relationship with the backbone absorption at 3.85 eV and Cotton band at 3.83 eV. For this reason, it was found that an optically active organopolysilane main-chain itself possessed only a fight-handed uniform helical structure.

The backbone absorption of the obtained poly[n-hexyl-(S)-2-methylbutylsilane] possessed the optical characteristics such that the absorption intensity and full width at half maximum were, respectively, approximately five times and one fifth, compared with that of the well-known optically inactive organopolysilane such as poly[methyl-n-propylsilane]. Furthermore, it was apparent that the obtained polysilane possessing one-handed helical structure could be extremely stable in a solution, since the backbone absorption intensity and the Cotton band intensity at −10° C. were approximately 110% based on those at 80° C. in i-octane. The obtained polysilane possessed approximately polymedal molecular weight distributions of the polymer, that was distinct from poly[n-butyl-(S)-2-methylbutylsilane], and often tended to possess two peaks. These characteristics which poly[n-hexyl-(S)-2-methylbutylsilane] possessed could be obtained in the case where the n-hexyl group of poly[n-hexyl-(S)-2-methylbutylsilane] was replaced with n-heptyl group, n-octyl group, n-nonyl group, n-decyl group, n-undecyl group, or n-dodecyl group.

The ultraviolet absorption spectra and the circular dichroism spectra (each in i-octane, 20° C.) of the first fractional precipitates of poly[n-heptyl-(S)-2-methylbutylsilane], poly[n-octyl-(S)-2-methylbutylsilane], poly[n-nonyl-(S)-2-methylbutylsilane], poly[n-decyl-(S)-2-methylbutylsilane], poly[n-undecyl-(S)-2-methylbutylsilane], and poly[n-dodecyl-(S)-2-methylbutylsilane], which were synthesized under the same polymerization condition as described in Example 6, are shown in FIG. 19 through FIG. 24, respectively.

Figure 19:
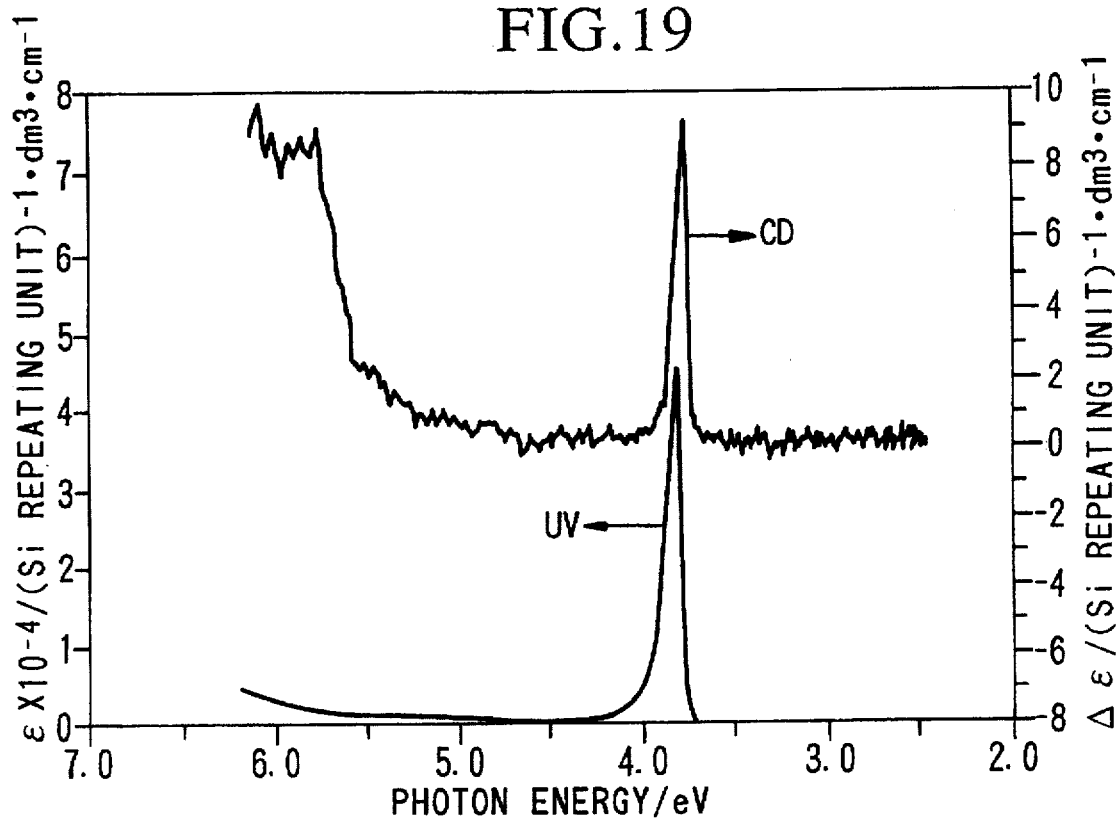
FIG. 19 is a drawing showing both an ultraviolet absorption spectrum and a circular dichroism spectrum (each in i-octane, 20° C.) of the first fractional precipitate of poly[n- heptyl-(S)-2-methylbutylsilane] (91270 of weight-average molecular weight and 1.42 of polydispersity) synthesized according to the process described in Example 6.

The first fractional precipitate of poly[n-heptyl-(S)-2-methylbutylsilane] possessed 91270 of weight-average molecular weight and 1.42 of polydispersity. The second fractional precipitate of poly[n-heptyl-(S)-2-methylbutylsilane] possessed 18180 of weight-average molecular weight and 2.14 of polydispersity. With regard to the second fractional precipitate, the peak of the ultraviolet absorption spectra was extremely similar to that of the circular dichroism spectra, as shown in FIG. 19.

The first fractional precipitate of poly[n-octyl-(S)-2-methylbutylsilane] possessed 50650 of weight-average molecular weight and 1.85 of polydispersity. The second fractional precipitate of poly[n-octyl-(S)-2-methylbutylsilane] possessed 21670 of weight-average molecular weight and 2.50 of polydispersity. With regard to the second fractional precipitate, the peak of the ultraviolet absorption spectra was extremely similar to that of the circular dichroism spectra, as shown in FIG. 20.

The first fractional precipitate of poly[n-decyl-(S)-2-methylbutylsilane] possessed 415300 of weight-average molecular weight and 5.6 of polydispersity. The second fractional precipitate of poly[n-decyl-(S)-2-methylbutylsilane] possessed 37840 of weight-average molecular weight and 1.88 of polydispersity. With regard to the second fractional precipitate, the peak of the ultraviolet absorption spectra was extremely similar to that of the circular dichroism spectra, as shown in FIG. 22.

The first fraction of poly[n-undecyl-(S)-2-methylbutylsilane]possessed 45600 of weight-average molecular weight and 2.08 of polydispersity. The second fractional precipitate of poly[n-undecyl-(S)-2-methylbutylsilane] possessed 5550 of weight-average molecular weight and 1.44 of polydispersity. With regard to the second fractional precipitate, the peak of the ultraviolet absorption spectra was extremely similar to that of the circular dichroism spectra, as shown in FIG. 23.

The first fractional precipitate of poly[n-dodecyl-(S)-2-methylbutylsilane] possessed 36400 of weight-average molecular weight and 2.08 of polydispersity. The second fractional precipitate of poly[n-dodecyl-(S)-2-methylbutylsilane] possessed 6360 of weight-average molecular weight and 1.25 of polydispersity. With regard to the second fractional precipitate, the peak of the ultraviolet absorption spectra was extremely similar to that of the circular dichroism spectra, as shown in FIG. 24.

Example 7

Synthesis of an optically active network-type of organopolysilane, using [(S)-2-methylbutyl]trichlorosilyne Sodium metal (30% dispersion, in toluene, 3.7 g), 15-crown-5 (0.05 g), and anhydrous toluene (50 mL) were put into a flask which had been dehydrated and deaerated, followed by charging of argon gas. [(S)-2-methylbutyl]trichlorosilane (3.05 g, 0.015 mol) was added to the mixture at the oil bath temperature of 60° C., and stirred for 15 minutes. The reaction mixture was filtered under pressure, and the filtrate was added to cooled ethyl alcohol which had been deaerated. The generated yellow precipitates were recovered using a centrifuge and then dried in vacuo at 60° C. The yield was 0.4 g. The GPC showed that the polymer was a mono-peak type of polymer possessing 4200 of weight average molecular weight and 1.8 of polydispersity.

The $^{29}$Si-NMR spectrum (CDCl$_3$, tetramethylsilane as an internal standard, gated proton decoupling technique) of the obtained poly[(S)-2-methylbutylsilyne], is shown in FIG. 25. One broad peak appeared at the range of around –20 ppm and –70 ppm. Such broad signal showed the characteristics in the network-type of organopolysilane obtained by the condensation reaction of n-alkyltrichlorosilane using an alkaline metal which had been reported. Therefore, it is conjectured that the structure of poly[(S)-2-methylbutylsilyne] synthesized by the sodium-mediated coupling reaction of [(S)-2-methylbutyl]trichlorosilane may microscopically possess silicon bonding condition wherein the magnetic environments are varied, i.e., there is a distribution of a bond length, a bond angle, or a torsion angle.

In addition, the main peak of poly[(S)-2-methylbutylsilyne] appeared at approximately –45 ppm through –50 ppm, while the main peak of a network-type of organopolysilane obtained by n-alkyltrichlorosilane, which had been reported hereto, appeared at approximately –60 ppm.

It was known that in a $^{29}$Si-NMR spectrum of a cyclic permethyloligosilane (silicon unit: 4, 5, 6), permethylcyclotetrasilane possesses a peak shifted downfield at around 15 ppm, compared with permethylcyclopentasilane or permethylcyclohexasilane. From this information, it is conjectured that poly[(S)-2-methylbutylsilyne] may be a so-called ladder-like polysilane which mainly possesses a condensed ring structure of 4-membered ring silicon skeleton.

The $^{13}$C-NMR spectrum (CDCl$_3$, tetramethylsilane as an internal standard, proton noise decoupling technique) of the obtained poly[(S)-2-methylbutylsilyne], is shown in FIG. 26. Some broad peaks appeared at around 34, 30, 23, and 12 ppm.

The ultraviolet absorption spectrum and the circular dichroism spectrum of the obtained poly[(S)-2-methylbutylsilyne] (each in i-octane, 20° C.) are shown in FIG. 27, and the photoluminescence spectrum of the same (in i-octane, 20° C.) is shown in FIG. 28.

A broad absorption showing no distinct peak, which is the characteristic of a network-like organopolysilane, appeared at 5 eV through 3 eV. On the other hand, in the circular dichroism spectrum, at least four positive or negative Cotton bands appeared at 2 eV through 6 eV.

Therefore, with regard to the obtained optically active network-like organopolysilane, it can be explained that both a right-handed helical (ladder) structure and a left-handed helical (ladder) structure, which are different from each other with respect to an energy eigenvalue, coexist in the same polymer backbone and silicon bonding electrons are not dispersed over the whole polymer chain but are localized as a segment.

Example 8

Synthesis of an optically active chain-like organopolysilane copolymer obtained by a copolymerization between an asymmetrically substituted optically active dichlorosilane and an asymmetrically substituted optically inactive dichlorosilane Sodium metal (30% dispersion, in toluene, 5.7 g) and anhydrous toluene (50 mL) were put into a flask which had been dehydrated and deaerated, followed by charging of argon gas. Mixed monomers of methylphenyldichlorosilane (6.0 g) and [(S)-2-methylbutyl]phenyldichlorosilane (0.75 g) (nominal molar feed ratio=90/10) was added to the mixture at the oil bath temperature of 70° C., and stirred for 1 hour. The reaction mixture was filtered under pressure, and the filtrate was subjected to a fractional precipitation using toluene and isopropylalcohol, thus separating into a high molecular weight component and a low molecular weight component. Each of the obtained white precipitates were recovered using a centrifuge and then dried in vacuo at 60° C. The yields of the first fractional precipitate and the second fractional precipitate were 0.1 g and 1.3 g, respectively. The GPC showed that the first fractional precipitate possessed 54000 of weight average molecular weight and 3.0 of polydispersity, while the second fractional precipitate possessed 5300 of weight average molecular weight and 2.0 of polydispersity.

The $^{29}$Si-NMR spectrum (CDCl$_3$, tetramethylsilane as an internal standard, gated proton decoupling technique) of the first fractional precipitate of the obtained poly[(methylphenylsilane)$_{90}$-co-{(S)-2-methylbutylphenylsilane}$_{10}$] is shown in FIG. 29. Plural peaks appeared at around –40 ppm.

The $^{13}$C-NMR spectrum (CDCl$_3$, tetramethylsilane as an internal standard, proton noise decoupling technique) of the first fractional precipitate of the obtained poly[(methylphenylsilane)$_{90}$-co-{(S)-2-methylbutylphenylsilane}$_{10}$] is shown in FIG. 30. Plural peaks based on the Si-methyl group of poly (methylphenylsilane) homopolymer appeared at around –3 ppm. In addition, plural peaks based on the (S)-2-methylbutyl group appeared at around 33, 22, 10, and 0 ppm.

From the results described above, it was found that the [(S)-2-methylbutyl]phenylsilane units were introduced into the main-chain of the obtained organopolysilane, and the ratio was approximately identified with the monomer feed ratio.

The ultraviolet absorption spectrum and the circular dichroism spectrum of the obtained poly[(methylphenylsilane)$_{90}$-co-{(S)-2-methylbutylphenylsilane}$_{10}$] (each in i-octane, 20° C.) are shown in FIG. 31, and the photoluminescence spectrum of the same (in i-octane, 20° C.) is shown in FIG. 32.

The comparison of those spectra showed that the lowest excited state of the backbone of poly[(methylphenylsilane)$_{90}$-co-{(S)-2-methylbutylphenylsilane}$_{10}$] was composed of a strong positive Cotton signal component at around 3.6 eV and a weak negative Cotton signal component at around 4.3 eV. For comparison, in a homopolymer of poly (methylphenylsilane), any Cotton signals were not observed.

The results obtained above could be explained by the following model: By virtue of introducing a small amount (approximately 10% by mole) of [(S)-2-methylbutyl] phenylsilane moiety into the poly(methylphenylsilane) skeleton, the backbone absorption becomes optically active. A right-handed helical structure and a left-handed helical structure, which are different from each other with respect to an excited energy eigenvalue, coexist in the same polymer backbone and the ratio of the right-handed helical structure to the left-handed helical structure is considerably high. This model corresponds to one in which silicon bonding electrons are not delocalized over the whole polymer chain but localized in both the right-handed helical segment and the left-handed helical segment, which are different from each other with respect to an excited energy eigenvalue.

Example 9

Synthesis of an optically active chain-like organopolysilane copolymer obtained by a copolymerization between a symmetrically substituted optically active dichlorosilane and a symmetrically substituted optically inactive dichlorosilane Sodium metal (30% dispersion, in toluene, 4.8 g), 15-crown-5 (0.12 g), and anhydrous toluene (50 mL) were put into a flask which had been dehydrated and deaerated, followed by charging of argon gas. Mixed monomers of di(n-butyl)dichlorosilane (4.7 g) and bis[(S)-2-methylbutyl] dichlorosilane (0.62 g) (charged mole ratio=90/10) was added to the mixture at the oil bath temperature of 100° C., and stirred for 3 hours. The reaction mixture was filtered under pressure, and the filtrate was subjected to a fractional precipitation using an deaerated and cooled isopropylalcohol. The obtained white precipitate was recovered using a centrifuge and then dried in vacuo at 60° C. The GPC showed that a first fractional precipitate possessed 517000 of weight average molecular weight and 1.8 of polydispersity, and a second fractional precipitate possessed 13000 of weight average molecular weight and 2.1 of polydispersity. The yields of the first fractional precipitate and the second fractional precipitate were 0.12 g and 0.78 g, respectively.

The $^{29}$Si-NMR spectrum (CDCl$_3$, tetramethylsilane as an internal standard, gated proton decoupling technique) of the first fractional precipitate of the obtained poly[(di-n-butylsilane)$_{90}$-co-[bis{(S)-2-methylbutyl}silane]$_{10}$] is shown in FIG. 33. Not only did one peak appear, which appeared in poly[di-n-butylsilane] homopolymer at around –23.0 ppm, but also two other peaks appeared at –22.5 ppm and –22.7 ppm. The intensity ratio of these peaks was approximately 70/20/10. For this reason, the peak at –22.5 ppm is assigned to a bis[(S)-2-methylbutyl]silane unit, the peak at –22.7 ppm is assigned to a di(n-butyl)silane unit neighboring to the bis[(S)-2-methylbutyl]silane unit.

The $^{13}$C-NMR spectrum (CDCl$_3$, tetramethylsilane as an internal standard, proton noise decoupling technique) of the first fractional precipitate of the obtained poly[(di-n-butylsilane)$_{90}$-co-[bis{(S)-2-methylbutyl}silane]$_{10}$] is shown in FIG. 34. Plural peaks based on the Si-butyl group of poly[di-n-butylsilane] homopolymer appeared at around 30, 27, 15, and 14 ppm. In addition, plural weak peaks, which may be based on the (S)-2-methylbutyl group, were observed at around 34, 29, 25, 23, 16, and 11 ppm.

From the results obtained above, it was found that the bis[(S)-2-methylbutyl]silane units were introduced into the main-chain of the obtained organopolysilane, and the ratio was approximately identified with the monomer feed ratio.

The ultraviolet absorption spectrum and the circular dichroism spectrum of the obtained poly[(di-n-butylsilane) $_{90}$-co-[bis{(S)-2-methylbutylsilane]$_{10}$] (each in i-octane, 20° C.) are shown in FIG. 35, and the photoluminescence spectrum of the same (in i-octane, 20° C.) is shown in FIG. 36.

The comparison of those spectra showed that the lowest excited state of the silicon backbone in the obtained chain-like organopolysilane copolymer at around 4.0 eV was composed of a strong positive Cotton signal peak at around 3.8 eV and a weak negative Cotton signal peak at around 4.2 eV. For comparison, in poly[di-n-butylsilane] homopolymer, such Cotton signals were not observed.

The results obtained above could be explained by the following model: By virtue of introducing a small amount (approximately 10% by mole) of bis[(S)-2-methylbutyl] silane moiety into the poly[di-n-butylsilane] skeleton, the backbone absorption becomes optically active. A right-handed helical structure and a left-handed helical structure, which are different from each other with respect to an excited energy eigenvalue, coexist in the same polymer backbone and the ratio of the right-handed helical structure to the left-handed helical structure is considerably high.

This model corresponds to one in which silicon bonding electrons are not dispersed over the whole polymer chain but are instead localized in both the right-handed helical segment and the left-handed helical segment, which are different from each other with respect to an excited energy eigenvalue.

As described above, by virtue of introducing a chiral organic substituent as a side-chain into a polymer backbone, it becomes possible to synthesize an organopolysilane exhibiting a circular dichroism property in the backbone absorption. Such optically active organopolysilane is anticipated for use not only as a novel type of enantio-recognitive material but also as a polymer standard material in one-dimensional semiconductor.quantum wire structure. In addition, chlorosilicons possessing chiral organo-substituents are expected to apply as CSP for GC or HPLC by coating the chlorosilanes directly to a porous silica (which can be pulverized or be spherical). Furthermore, by virtue of selecting an advantageous substituent in a side-chain, it is possible to provide an organopolysilane possessing a mono-helical structure, wherein a primary structure, a secondary structure, and a chain length are almost complete, and having optical properties such that the absorption intensity of the backbone is extremely strong and the width of the absorption is extremely narrow, compared with the conventional organopolysilanes, and possessing, in a given case, a mono disperse molecular weight. These organopolysilanes possessing a mono-helical structure can be provided as a polymer standard material since they are considerably useful as a basically model substance for researches of optical and electrical properties including quantum wires with ultimately fine structure, which will be actual in a nearly future or an ideal one-dimensional semiconductor wherein there is no the interchain interaction.

Example 10

Synthesis of n-hexyl(i-butyl)dichlorosilane.

Anhydrous diethyl ether (125 mL) was put into a reactor with magnesium (5.0 g, 0.21 mol) which had been dehydrated and deaerated, followed by charging of argon gas. A small amount of iodine was slowly added to the mixture. i-Butylbromide (25 g, 0.18 mol) was added dropwise to the slowly stirred mixture so that the reaction mixture was gradually refluxed. After the reaction was complete, the obtained Grignard reagent was transferred to a dropping funnel. The Grignard reagent was added dropwise to a solution being stirred containing n-hexyltrichlorosilane (64 g, 0.25 mol) in anhydrous diethyl ether (50 mL)/anhydrous tetrahydrofuran (50 mL) in another reactor which had been dehydrated and deaerated, followed by charging of argon gas, at 50° C.–60° C. The reaction mixture was then stirred overnight at room temperature. Hexane (500 mL) was added to the reaction mixture, and the resulting mixture was filtered under pressure, followed by fractional distillation of the filtrate to provide the desired product.
Main fraction:
  Boiling point 86° C.–88° C./3.2 mmHg
  Yield 23 g (53%).
  $^{29}$Si-NMR (CDCl$_3$, tetramethylsilane as an internal standard, gated proton decoupling technique) 32.64 ppm.
  $^{13}$C-NMR (CDCl$_3$, tetramethylsilane as an internal standard, WALTZ proton noise decoupling technique) 32.24, 31.40, 30.49, 25.65 (intensity: double), 24.25, 22.55, 22.46, 21.37, and 14.12 ppm.

Example 11

Synthesis of n-hexyl(3-methylbutyl)dichlorosilane.

Anhydrous tetrahydrofuran (125 mL) was put into a reactor with magnesium (5.0 g, 0.21 mol) which had been dehydrated and deaerated, followed by charging of argon gas. A small amount of iodine was slowly added to the mixture. 3-Methylbutylbromide (25 g, 0.17 mol) was added dropwise to the slowly stirred mixture so that the reaction mixture was gradually refluxed. After the reaction was complete, the obtained Grignard reagent was transferred to a dropping funnel. The Grignard reagent was added dropwise to a solution being stirred containing n-hexyltrichlorosilane (38 g, 0.17 mol) in anhydrous tetrahydrofuran (100 mL) in another reactor which had been dehydrated and deaerated, followed by charging of argon gas, at 60° C.–70° C. The reaction mixture was then stirred overnight at room temperature. Hexane (500 mL) was added to the reaction mixture, and the resulting mixture was filtered under pressure, followed by fractional distillation of the filtrate to provide the desired product.
Main fraction:
  Boiling point 80° C.–81° C./1.2 mmHg.
  Yield 25 g (59%).
  $^{29}$Si-NMR (CDCl$_3$, tetramethylsilane as an internal standard, gated proton decoupling technique) 34.01 ppm.
  $^{13}$C-NMR (CDCl$_3$, tetramethylsilane as an internal standard, WALTZ proton noise decoupling technique) 32.18, 31.37, 31.16, 30.19, 22.52, 22.38, 21.98 (intensity: double), 20.16, 18.03, and 14.09 ppm.

Example 12

Synthesis of n-hexyl(2-ethylbutyl)dichlorosilane.

Anhydrous diethyl ether (100 mL) was put into a reactor with magnesium (5.0 g, 0.21 mol) which had been dehydrated and deaerated, followed by charging of argon gas. A small amount of iodine was slowly added to the mixture. 2-Ethylbutylbromide (29.5 g, 0.18 mol) was added dropwise to the slowly stirred mixture so that the reaction mixture was gradually refluxed. After the reaction was complete, the obtained Grignard reagent was transferred to a dropping funnel. The Grignard reagent was added dropwise to a solution being stirred containing n-hexyltrichlorosilane (38 g, 0.17 mol) in anhydrous tetrahydrofuran (100 mL) in another reactor which had been dehydrated and deaerated, followed by charging of argon gas, at 60° C.–70° C. The reaction mixture was then stirred overnight at room temperature. Hexane (500 mL) was added to the reaction mixture, and the resulting mixture was filtered under pressure, followed by fractional distillation of the filtrate to provide the desired product.
Main fraction:
  Boiling point 82° C.–83° C./0.6 mmHg.
  Yield 25 g (52%).
  $^{29}$Si-NMR (CDCl$_3$, tetramethylsilane as an internal standard, gated proton decoupling technique) 33.61 ppm.
  $^{13}$C-NMR (CDCl$_3$, tetramethylsilane as an internal standard, WALTZ proton noise decoupling technique) 35.82, 32.09, 31.25, 27.61 (intensity: double), 24.67, 22.40, 22.34, 21.17, 14, and 10.46 (intensity: twice) ppm.

With regard to two kinds of n-butyldichlorosilanes containing i-butyl group and a 3-methylbutyl group, respectively, which were synthesized in the same manner as described above, the data of boiling point, chemical shifts of $^{29}$Si-NMR (CDCl$_3$, tetramethylsilane as an internal standard, gated proton decoupling technique) and $^{13}$C-NMR (CDCl$_3$, tetramethylsilane as an internal standard, WALTZ proton noise decoupling technique) are listed on Table 4. In the tables, "X2" and "X3" used in the data of $^{13}$C-NMR mean a two-fold increase and a three-fold increase in peak intensity, respectively. In the data of $^{13}$C-NMR, "X2" means that the peak intensity is double.

The yields of these dichlorosilanes are in the range of approximately 45% and 55%, based on the i-butyl group or 3-methylbutyl group.

TABLE 4

|  | n-C4, i-C4 | n-C4, 3-MeBu |
|---|---|---|
| bp (°C./mmHg) | 88–90/7 | 92–93/9.5 |
| $^{29}$Si (ppm) | 32.72 | 34.09 |
| $^{13}$C (ppm) | 13.61 | 13.66 |
|  | 21.04 | 18.05 |
|  | 24.21 | 20.01 |
|  | 24.58 | 22.02 (X2) |
|  | 25.56 | 24.59 |
|  | 25.61 (X2) | 25.59 |
|  | 30.42 | 30.22 |
|  |  | 31.17 |

Examples 13 to 15 described below show synthesis examples of organopolysilanes possessing a strong backbone absorption and a narrow width of the absorption, using n-alkyl(aralkyl branched alkyl)dichlorosilanes. The present invention reveals that optical properties are varied greatly by virtue of the aralkyl branched alkyl structure.

Example 13

Synthesis of poly[n-hexyl-i-butylsilane]

Sodium metal (30% dispersion, in toluene, 2.5 g), 15-crown-5 (0.05 g), and anhydrous toluene (50 mL) were put into a flask which had been dehydrated and deaerated, followed by charging of argon gas. n-Hexyl-i-butyl-dichlorosilane (4.8 g, 0.020 mol) was added to the mixture at the oil bath temperature of 100° C., and stirred for 5 hours. The reaction mixture was filtered under pressure, and ethyl alcohol was added to the filtrate. The generated white viscous precipitate was recovered using a centrifuge and then dried in vacuo at 60° C. Yield was 0.42 g and 15% based on n-hexyl(i-butyl)dichlorosilane. GPC on the basis of mono disperse polystyrene showed that the polymer was a mono-peak type of polymer possessing 18900 of weight-average molecular weight and 1.84 of polydispersity.

The $^{29}$Si-NMR spectrum (CDCl$_3$, tetramethylsilane as an internal standard, gated proton decoupling technique) of the obtained poly[n-hexyl-i-butylsilane] is shown in FIG. 37. One broad peak appeared at around −23 ppm.

The $^{13}$C-NMR spectrum (CDCl$_3$, tetramethylsilane as an internal standard, proton noise decoupling technique) of the obtained poly[n-hexyl-i-butylsilane] is shown in FIG. 38. Several peaks appeared at around 34, 31, 28, 26, 23, 16, and 14 ppm.

The ultraviolet absorption spectrum and the photoluminescence spectrum of poly[n-hexyl-i-butylsilane] (each in i-octane, 20° C.) is shown in FIG. 39.

From these two spectra, it was revealed that the lowest excited state of the main-chain at approximately 3.9 eV in poly[n-hexyl-i-butylsilane] was in a uniform helical state since the ultraviolet absorption spectrum and the photoluminescence spectrum displayed a mirror image relationship.

Example 14

Synthesis of poly[n-hexyl-3-methylbutylsilane]

Sodium metal (30% dispersion, in toluene, 3.5 g), 15-crown-5 (0.08 g), and anhydrous toluene (50 mL) were put into a flask which had been dehydrated and deaerated, followed by charging of argon gas. n-Hexyl(3-methylbutyl)dichlorosilane (5.1 g, 0.020 mol) was added to the mixture at the oil bath temperature of 100° C., and stirred for 3 hours. The reaction mixture was filtered under pressure, and ethyl alcohol was gradually added to the filtrate. The generated white precipitate was recovered using a centrifuge and then dried in vacuo at 60° C. Yield of a first fraction was 0.10 g and 2.3%, and yield of a second fraction was 0.81 g and 18.4%. According to GPC technique, the first fraction possessed 214400 of weight average molecular weight and 3.29 of polydispersity and the second fraction possessed 28400 of weight average molecular weight and 2.22 of polydispersity.

The $^{29}$Si-NMR spectrum (CDCl$_3$, tetramethylsilane as an internal standard, gated proton decoupling technique) of the obtained poly[n-hexyl-3-methylbutylsilane] is shown in FIG. 40. One broad peak appeared at around −25 ppm.

The $^{13}$C-NMR spectrum (CDCl$_3$, tetramethylsilane as an internal standard, proton noise decoupling technique) of the obtained poly[n-hexyl-3-methylbutylsilane] is shown in FIG. 41. Several peaks appeared at around 36, 34, 32, 28, 23, 22, 15, 14, and 12 ppm.

The ultraviolet absorption spectrum and the photoluminescence spectrum of poly[n-hexyl-3-methylbutylsilane] (each in i-octane, 20° C.) is shown in FIG. 42.

From these two spectra, it was revealed that the lowest excited state of the main-chain at approximately 3.9 eV in poly[n-hexyl-3-methylbutylsilane] was in a uniform helical state since the ultraviolet absorption spectrum and the photoluminescence spectrum displayed a mirror image relationship. As shown in FIG. 46, with regard to poly(methylpropylsilane), the ultraviolet absorption spectrum and the photoluminescence spectrum of the same did not display a mirror image relationship.

Example 15

Synthesis of poly[n-hexyl-2-ethylbutylsilane]

Sodium metal (30% dispersion, in toluene, 1.9 g), 15-crown-5 (0.05 g), and anhydrous toluene (50 mL) were put into a flask which had been dehydrated and deaerated, followed by charging of argon gas. n-Hexyl(2-ethylbutyl)dichlorosilane (2.05 g, 0.011 mol) was added to the mixture at the oil bath temperature of 120° C., and stirred for 4 hours. The reaction mixture was filtered under pressure, and ethyl alcohol was added to the filtrate. The generated white precipitate was recovered using a centrifuge and then dried in vacuo at 60° C. Yield was 0.45 g. According to GPC technique, the polymer was mono-peak type of polymer possessing 12800 of weight average molecular weight and 2.2 of polydispersity.

The $^{29}$Si-NMR spectrum (CDCl$_3$, tetramethylsilane as an internal standard, gated proton decoupling technique) of poly[n-hexyl-2-ethylbutylsilane]is shown in FIG. 43. One broad peak appeared at around −20.6 ppm.

The $^{13}$C-NMR spectrum (CDCl$_3$, tetramethylsilane as an internal standard, proton noise decoupling technique) of the obtained poly[n-hexyl-2-ethylbutylsilane] is shown in FIG. 44. Some peaks appeared at around 38, 34, 32, 28, 23, 20–16, 14, 11, and 10 ppm.

The ultraviolet absorption spectrum and the photoluminescence spectrum of poly[n-hexyl-2-ethylbutylsilane] (each in i-octane solution, 20° C.) is shown in FIG. 45.

From these two spectra, it was revealed that the lowest excited state of the main-chain at approximately 3.9 eV in poly[n-hexyl-2-ethylbutylsilane] was in a uniform helical state since the ultraviolet absorption spectrum and the photoluminescence spectrum displayed a mirror image relationship.

It is apparent that the optical characteristics (increasing of intensity and narrowing of width in the main-chain absorption, the mirror image property of the absorption spectrum and photoluminescence spectrum) of poly[n-hexyl-i-butylsilane], poly[n-hexyl-3-methylbutylsilane], and poly[n-hexyl-2-ethylbutylsilane] are appeared in the case where the n-hexyl group of poly[n-hexyl-i-butylsilane], poly[n-hexyl-3-methylbutylsilane], or poly[n-hexyl-2-ethylbutylsilane] mentioned above is replaced with ethyl group, n-propyl group, n-butyl group, n-pentyl group, n-heptyl group, n-octyl group, n-nonyl group, n-decyl group, n-undecyl group, or n-dodecyl group. Especially in the case of ethyl group, n-propyl group, n-butyl group, and n-pentyl group, there can be provided a mono disperse polymer possessing 3000–5000 of weight-average molecular weight and 1.1–1.3 of polydispersity.

Comparative Examples

For comparison, as an organopolysilane possessing the groups which do not have β-branched structures (a combination of n-alkyl group and n-alkyl group, or a combination of methyl group and n-alkyl group), the ultraviolet absorption spectra and the photoluminescence spectra of poly[methyl-n-propylsilane] (Comparative Example 1) and poly[di-n-hexylsilane] (Comparative Example 2) are shown in FIGS. 46 and 47.

The backbone absorption of poly[n-hexyl-i-butylsilane] at around 4.0 eV possessed, compared with those of poly[methyl-n-propylsilane] and poly[di-n-hexylsilane], 4.5 times and 3.5 times of the absorption intensity and approximately ⅕ and ¼ of the full width at half maximum, respectively.

The backbone absorption of poly[n-hexyl-3-methylbutylsilane] at around 4.0 eV possessed, compared with those of poly[methyl-n-propylsilane] and poly[di-n-hexylsilane], twice and 1.5 times of the absorption intensity and approximately ⅓ and ½ of the full width at half maximum, respectively.

In addition, the backbone absorption of poly[n-hexyl-2-ethylbutylsilane] at around 4.0 eV possessed, compared with those of poly[methyl-n-propylsilane] and approximately ⅙ and ⅕ of the full width at half maximum, respectively.

The absorption.photoluminescence spectrum profiles of poly[n-hexyl-i-butylsilane], poly[n-hexyl-3-methylbutylsilane], and poly[n-hexyl-2-ethylbutylsilane] were completely in an minor image relationship, compared with those of poly[methyl-n-propylsilane] or poly[di-n-hexylsilane]. For this reason, it is demonstrated that the photoluminescence occurs not from a partial segment in the backbone, but from the whole backbone. Therefore, the result suggests that by virtue of a conformation-fixation effect of a β-branched alkyl substituent, the whole backbone is rigid and in a single electronic excitation state.

As described above, by virtue of an organochlorosilane possessing alkyl group with a β-branched aralkyl structure as well as the sodium-mediated coupling reaction of the same, it becomes possible to synthesize an organopolysilane exhibiting a circular dichroism property in the backbone absorption. Such optically active organopolysilane has anticipated uses not only as a novel type of enantiorecognitive material, but also as a polymer standard material of a one-dimensional semiconductor.quantum wire structure. In addition, chlorosilanes possessing chiral organosubstituents are expected to apply as CSP for GC or HPLC by coating the chlorosilanes directly to the porous silica (which can be pulverized or be formed as granules). Furthermore, by virtue of selecting an advantageous substituent in a side-chain, it is possible to provide an organopolysilane possessing a mono-helical structure, wherein a primary structure, a secondary structure, and a chain length are almost complete, and having optical properties such that the absorption intensity of the backbone is extremely strong and the width of the absorption is extremely narrow, compared with the conventional organopolysilanes, and possessing, in a given case, a mono disperse molecular weight. These organopolysilanes possessing a mono-helical structure can be provided as a polymer standard material since they are considerably useful as a basic model substance for researches of optical and electrical properties including quantum wires with ultimately fine structure, which will be actualized in the near future, or will be an ideal one-dimensional semiconductor wherein there is no interchain interaction.

What is claimed is:

1. An organosilicon compound possessing a β-branched alkyl group and represented by Formula (II):

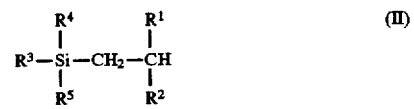

wherein $R^1$ represents a methyl group or an ethyl group; $R^2$ represents a C1–C18 alkyl group; $R^3$, $R^4$, and $R^5$, each independently represent Si, Cl, an alkyl group, an aryl group, or an aralkyl group, with the exception of those compounds in which, at the same time:

(a) $R^1$ and $R^2$ each represent a methyl group, and $R^3$, $R^4$, and $R^5$ each independently represent Cl;

(b) one of $R^1$ and $R^2$ represents a methyl group and the other represents an ethyl group, and two of $R^3$, $R^4$, and $R^5$ represent Cl and the third represents a methyl group; and (c) $R^1$ and $R^2$ each represent a methyl group, and two of $R^3$, $R^4$, and $R^5$ represent Cl and the third represents a methyl group.

2. An organosilicon compound as recited in claim 1, which is optically active, and wherein the β-branched alkyl group is chiral.

3. An organosilicon compound as recited in claim 2, wherein $R^1$ is a methyl group; $R^2$ is an ethyl group; $R^3$ represents an alkyl group, an aryl group, or an aralkyl group; $R^4$ and $R^5$ each represent Cl.

4. An organosilicon compound as recited in claim 2, wherein $R^1$ is a methyl group; $R^2$ is an ethyl group; $R^3$, $R^4$, and $R^5$ each represent Cl.

5. An organosilicon compound as recited in claim 1, which is not optically active, wherein the β-branched alkyl group is achiral, and wherein both $R^1$ and $R^2$ represent a methyl group or an ethyl group; $R^3$ represents an alkyl group, an aryl group, or an aralkyl group; and $R^4$ and $R^5$ each represent Cl.

6. An organosilicon compound possessing a β-branched alkyl group and represented by Formula (II):

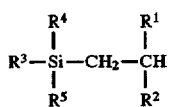

(II)

wherein $R^1$ represents a methyl group or an ethyl group; $R^2$ represents a C1–C18 alkyl group; $R^3$, $R^4$, and $R^5$, each independently represent Si, Cl, an alkyl group, an aryl group, or an aralkyl group, and further wherein said organosilicon compound is an organopolysilane.

7. An organopolysilane as recited in claim 6, said organopolysilane being derived from an optically active dichlorosilane represented by formula (II) wherein the β-branched alkyl is chiral, and having the Formula (III):

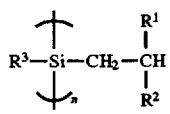

(III)

wherein $R^1$ is a methyl group; $R^2$ is an ethyl group; $R^3$ represents an alkyl group, an aryl group, or an aralkyl group; and n is an integer of 10 or more.

8. An organopolysilane as recited in claim 6, said organopolysilane being derived from an optically active trichlorosilane represented by formula (II) wherein the β-branched alkyl group is chiral, and having the Formula (IV):

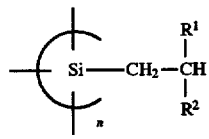

(IV)

wherein $R^1$ is a methyl group; $R^2$ is an ethyl group; and n is an integer of 10 or more.

9. An organopolysilane as recited in claim 6, said organopolysilane being derived from an optically inactive dichlorosilane represented by formula (II) wherein the β-branched alkyl group is achiral, and having the Formula (V):

(V)

wherein $R^1$ is a methyl group; $R^2$ is an ethyl group; $R^3$ represents Cl; and n is an integer of 10 or more.

10. An organosilicon compound as recited in claim 6, which is an optically active polysilane copolymer.

11. An optically active polysilane copolymer as recited in claim 10, said optically active polysilane copolymer being derived from an optically active silane compound of formula (II), wherein the β-branched alkyl group is chiral, and an optically inactive silane compound of formula (II), wherein the β-branched alkyl group is achiral, and having the Formula (VI):

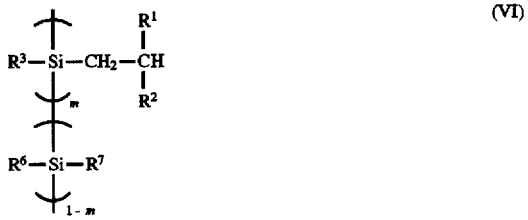

(VI)

wherein $R^1$ represents a methyl group or an ethyl group; $R^2$ represents a C1–C18 alkyl group; and $R^3$ represents Si, Cl, an alkyl group, an aryl group, or an aralkyl group; $R^6$ and $R^7$ each independently represent an alkyl group, an aryl group, or an aralkyl group; and $0.01 < m < 1$.

* * * * *

UNITED STATES PATENT AND TRADEMARK OFFICE
CERTIFICATE OF CORRECTION

PATENT NO. : 5,710,301
DATED : January 20, 1998
INVENTOR(S) : Michiya FUJIKI

It is certified that error appears in the above-indentified patent and that said Letters Patent is hereby corrected as shown below:

Title Page, item [75], in the Inventor, line 1, delete "1182-1-4-403, Hase"; and line 2, delete "Atsugi" should read --Atsugi-shi--.

Title Page, after item [75], insert item --[73] Assignee: Nippon Telegraph and Telephone Corporation, Tokyo, Japan--.

Title Page, after "Primary Examiner", insert --Attorney, Agent or Firm—Finnegan, Henderson, Farabow, Garrett and Dunner, L.L.P.--

UNITED STATES PATENT AND TRADEMARK OFFICE
CERTIFICATE OF CORRECTION

PATENT NO.  : 5,710,301
DATED       : January 20, 1998
INVENTOR(S) : Michiya FUJIKI It is certified that error appears in the above-indentified patent and that said Letters Patent is hereby corrected as shown below:

Title Page, Item [57], in the Abstract, lines 10-11, "semiconductor quantum" should read --semiconductor·quantum--.

Signed and Sealed this

Fifth Day of October, 1999

Q. TODD DICKINSON

*Attest:*

*Attesting Officer*    Acting Commissioner of Patents and Trademarks